US009192577B2

(12) United States Patent
Vandecruys et al.

(10) Patent No.: US 9,192,577 B2
(45) Date of Patent: Nov. 24, 2015

(54) PHARMACEUTICAL COMPOSITIONS COMPRISING A BASIC DRUG COMPOUND, A SURFACTANT, AND A PHYSIOLOGICALLY TOLERABLE WATER SOLUBLE ACID

(75) Inventors: Roger Petrus Gerebern Vandecruys, Westerlo (BE); Jozef Peeters, Beerse (BE); Marcus Eli Brewster, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 2275 days.

(21) Appl. No.: 10/536,542

(22) PCT Filed: Nov. 25, 2003

(86) PCT No.: PCT/EP03/50890
§ 371 (c)(1),
(2), (4) Date: May 26, 2005

(87) PCT Pub. No.: WO2004/050058
PCT Pub. Date: Jun. 17, 2004

(65) Prior Publication Data
US 2006/0078609 A1 Apr. 13, 2006

(30) Foreign Application Priority Data
Nov. 29, 2002 (WO) ................ PCT/EP02/13558

(51) Int. Cl.
| A61K 9/20 | (2006.01) |
| A61K 9/14 | (2006.01) |
| A61K 9/107 | (2006.01) |
| A61K 9/16 | (2006.01) |
| A61K 9/48 | (2006.01) |
| A61K 9/50 | (2006.01) |
| A61K 31/505 | (2006.01) |

(52) U.S. Cl.
CPC ............ *A61K 9/145* (2013.01); *A61K 9/1075* (2013.01); *A61K 9/146* (2013.01); *A61K 9/1617* (2013.01); *A61K 9/1635* (2013.01); *A61K 9/1652* (2013.01); *A61K 9/2009* (2013.01); *A61K 9/4858* (2013.01); *A61K 9/4866* (2013.01); *A61K 9/5084* (2013.01); *A61K 31/505* (2013.01)

(58) Field of Classification Search
CPC ................................... A61K 9/1075
USPC .......................... 424/464; 514/275
See application file for complete search history.

(56) References Cited

U.S. PATENT DOCUMENTS

| 4,596,705 | A | * | 6/1986 | Schepky et al. ........... 424/468 |
| 4,696,815 | A | | 9/1987 | Schepky et al. |
| 5,558,876 | A | | 9/1996 | Desai et al. |
| 5,593,693 | A | | 1/1997 | Gergely et al. |
| 6,416,793 | B1 | | 7/2002 | Zeligs et al. |
| 6,828,301 | B2 | * | 12/2004 | Chen et al. ........... 514/9 |
| 6,919,370 | B2 | * | 7/2005 | Chen ............... 514/449 |
| 2001/0029264 | A1 | | 10/2001 | McChesney-Harris |
| 2001/0049366 | A1 | | 12/2001 | Singh et al. |
| 2008/0160106 | A1 | * | 7/2008 | Fais et al. ........... 424/687 |

FOREIGN PATENT DOCUMENTS

| EP | 834507 | 4/1998 | |
| EP | 1350508 | 11/2005 | |
| JP | 5-255066 | 10/1993 | |
| JP | 9-202728 | 8/1997 | |
| WO | WO 95/07696 A | 3/1995 | |
| WO | WO 95/20384 A | 8/1995 | |
| WO | WO 95/23594 A1 | 9/1995 | |
| WO | WO 9530420 | 11/1995 | |
| WO | WO 97/02017 | * 1/1997 | ........... A61K 9/14 |
| WO | WO 97/02017 A1 | 1/1997 | |
| WO | WO 97/35587 A1 | 10/1997 | |
| WO | WO 98/08490 A1 | 3/1998 | |
| WO | WO 99/26607 A1 | 6/1999 | |
| WO | WO 99/45918 A1 | 9/1999 | |
| WO | WO 9950250 | 10/1999 | |
| WO | WO 00/59475 | 10/2000 | |
| WO | WO 01/22938 | * 4/2001 | ........... A61K 9/14 |
| WO | WO 01/22938 A1 | 4/2001 | |
| WO | WO 01/23362 A2 | 4/2001 | |
| WO | WO 01/30319 A1 | 5/2001 | |
| WO | 01/47495 | 7/2001 | |
| WO | 01/47500 | 7/2001 | |

OTHER PUBLICATIONS

Merriam-Webster's Collegiate Dictionary (Merriam-Webster Incorporated: Springfield, Massachusetts, 1993, pp. 311).*
CASODEX (Drug Information at http://www.rxlist.com/casodex-drug.htm (2009).*
Peeters, J. et al: "Development of an extended release oral dosage form using experimental design"; Proceedings—28th International Symposium on Controlled Release of Bioactive Materials and 4th Consumer & Diversified Products Conference, San Diego, CA, United States, Jun. 23-27, 2001 (vol. 1, 704-705 Publisher: Controlled Release Society, Jun. 23, 2001, XP001152635.
International Search Report for PCT/EP 03/50890 dated Jul. 5, 2004.
Yu, L. et al., "Vitamin E TPGS Increases Absorption Flux O Fan HIV Protease Inhibitor", Pharmaceutical Research, 1999, 16(12), 1812-1817.
Eastman Vitamin E TPGS, NF Grade, (2008).

* cited by examiner

*Primary Examiner* — Jake Vu
(74) *Attorney, Agent, or Firm* — Kiera K. Mathey

(57) ABSTRACT

The invention provides a novel pharmaceutical composition comprising a basic respectively acidic drug compound, a surfactant and a physiologically tolerable water-soluble acid respectively base characterized in that the acid respectively base:drug compound ratio is at least 1:1 by weight.

43 Claims, No Drawings

PHARMACEUTICAL COMPOSITIONS COMPRISING A BASIC DRUG COMPOUND, A SURFACTANT, AND A PHYSIOLOGICALLY TOLERABLE WATER SOLUBLE ACID

CROSS REFERENCE TO RELATED APPLICATIONS

This application is the national stage of Application No. PCT/EP2003/050890, filed Nov. 25, 2003, which application claims priority from PCT/EP02/13558 filed Nov. 29, 2002.

This invention relates to novel pharmaceutical compositions, in particular compositions and dosage forms providing improved drug release and uptake on administration into externally voiding body cavities (e.g. the gastro-intestinal tract) or on topical administration, especially for acid solubilized drug compounds.

Many drug compounds, while possessing desired therapeutic properties, are used inefficiently due to their poor water solubilities. Thus for example where such compounds are administered orally, only a small fraction of the drug is taken up into the blood during transit of the gastro-intestinal tract. As a result, to achieve adequate drug uptake it may be necessary to administer high doses of the drug compound, to prolong the period of drug administration or to make frequent administrations of the drug compound. Indeed, the poor solubility and hence poor bioavailability of a drug may cause an alternative drug, perhaps one with undesired side effects or one which requires invasive administration (e.g. by injection or infusion), to be used in place of the poorly soluble drug.

One approach to poor solubility is to derivatise the drug molecule to introduce water solubilizing groups, e.g. ionic groups such as carboxyl groups or non-ionic groups such as polyhydroxyalkyl groups, so as to produce a more soluble derivative. This approach however is not always successful as it may not be possible to maintain adequately high therapeutic efficacy and adequately low toxicity or other side effects. Thus one example of a poorly water soluble drug which has not been superseded by a solubilized derivative is the antifungal agent itraconazole.

Attempts have therefore been made to enhance the uptake of drugs such as itraconazole by increasing the surface area of the drug compound exposed to saliva or gastric fluid, and hence promote dissolution of the drug compound, by thinly coating the drug compound onto essentially inert carrier particles, e.g. sugar beads. This however has the drawback that the volume of solid composition required to administer a given quantity of the drug compound is quite high since the carrier contributes significantly to the overall administration volume. Since administration of large volume capsules or tablets, or of large quantities of smaller volume capsules or tablets, provides difficulties for the patient, the drawbacks of this approach are obvious.

Yet another approach has been to administer the drug compound in the form of a solution of the drug compound and a drug complexing agent such as a cyclodextrin. This approach has limitations also in that the formulation is constrained to those drugs which are able to form complexes with cyclodextrins, in that the dosage volume is constrained by the solubilizing power of the complexing agent, in that readily unitized solid dosage forms can not be used, and in that there is no gradual release of the drug compound for biological uptake.

The drug compound can also be formulated as a solid dispersion in cyclodextrins together with a physiologically tolerable water soluble acid and a physiologically tolerable water soluble organic polymer. Reference therefore is made to WO 98/55148. This approach has limitations in that the formulation is constrained to those drugs which are able to form complexes with cyclodextrins and in that the dosage volume is constrained by the solubilizing power of the complexing agent.

Another approach to increase drug release from the dosage form and hence to enhance the oral bioavailability of the drug is to administer the drug together with a suitable surfactant.

WO 97/35587 describes a liquid formulation comprising an HIV protease inhibitor and a water soluble tocopherol derivative, in particular Vitamin E-TPGS.

WO 98/08490 describes a solid dry coprecipitate composition comprising tocopherol polyethyleneglycol succinate, a lipophilic active ingredient and a dispersion adjuvant.

WO 99/26607 describes solid dispersions of a drug and Vitamin E TPGS.

WO 99/45918 describes compositions comprising a taxane, one or more surfactants and an acid. The acid is included in the formulation to improve the stability of the taxane.

WO 97/02017 describes solid dispersions comprising a poorly soluble active ingredient in a hydrophilic poloxamer polymer. The dispersion may further contain an acid. The acid is included in the solid dispersion in order to provide for a gradual availability of the acid to promote the solubilization of the active ingredient over the bulk of the release rate curve.

The compositions of the present invention are distinguishable from the prior art compositions in that they provide for a faster dissolution profile of the drug compound and/or in that they are able to provide for a higher solubility for the drug compound (creating a supersaturated condition). This results in an enhanced bioavailability for the drug compound; an improved biological uptake of the drug compound (an improved time profile for the drug content of the plasma of the patient, i.e. the pharmacokinetic profile defined by such parameters as AUC, $t_{max}$, $C_{max}$, etc. is improved). The incorporation of the drug compound in the compositions of the present invention is also independent on complex formation, which makes the present compositions suitable for the formulation of a broad range of drug compounds.

SUMMARY OF THE INVENTION

We have now found that the above described characteristics of the present compositions could be achieved by combining a basic respectively acidic drug compound with a surfactant and a significant amount of a water-soluble acid respectively base.

Thus viewed from one aspect the invention provides a pharmaceutical composition comprising a basic drug compound, a surfactant and a physiologically tolerable water-soluble acid characterized in that the acid:drug compound ratio is at least 1:1 by weight or comprising an acidic drug compound, a surfactant and a physiologically tolerable water-soluble base characterized in that the base:drug compound ratio is at least 1:1 by weight.

In other words, the present invention provides a pharmaceutical composition comprising a basic respectively acidic drug compound, a surfactant and a physiologically tolerable water-soluble acid respectively base characterized in that the acid respectively base:drug compound ratio is at least 1:1 by weight.

Viewed from a further aspect the invention provides the use of a basic respectively acidic drug compound, a surfactant and a physiologically tolerable water-soluble acid respectively base in an acid respectively base:drug ratio of at least 1:1 by weight for the manufacture of a pharmaceutical composition according to the invention for use in a method of prophylaxis, therapy or diagnosis of the human or non-human animal (e.g. mammalian, reptilian or avian) body.

Viewed from a still further aspect the invention provides a method of prophylaxis, therapy or diagnosis of the human or non-human animal (e.g. mammalian, reptilian or avian) body which comprises administering to said body a prophylactically, therapeutically or diagnostically effective dose of a pharmaceutical composition, the improvement comprising using as said composition a composition according to the present invention.

DETAILED DESCRIPTION OF THE INVENTION

While not wishing to be bound by theory it is thought that the advantageous drug compound dissolution profile for the compositions of the invention is achieved as a result of a combination of the effects of the components of the composition on exposure to water or aqueous body fluids.

In the case the composition comprises a basic drug compound and a physiologically tolerable water-soluble acid, the water and the acid provide upon exposure to water or aqueous body fluids for an acidic microenvironment in which the solubility of the basic drug compound is increased. The presence of the surfactant causes a further increase in the solubility of the drug compound thereby producing a supersaturated solution of the drug compound.

In case the composition comprises an acidic drug compound and a physiologically tolerable water-soluble base, the water and the base provide upon administration for an alkaline microenvironment in which the solubility of the acidic drug compound is increased. The surfactant, as described above, causes the production of a supersaturated solution of the drug compound.

The supersaturated solution which is created upon administration of the present compositions provides for an increased bioavailability of the drug compound.

Since the present compositions provide themselves for a microenvironment in which the solubility of the drug compound is increased, they can be orally administered at any time of the day independently of the food taken in by the individual to whom they are administered.

Preferred compositions are those compositions comprising a basic drug compound, a surfactant and a physiologically tolerable water-soluble acid characterized in that the acid:drug compound ratio is at least 1:1 by weight.

As for the surfactant in the compositions of the invention, there may be used any of the physiologically tolerable surfactants suitable for use in a pharmaceutical composition.

It is well-known in the art that a surfactant is an amphiphilic compound; it contains polar, hydrophilic moieties as well as non-polar, hydrophobic moieties.

The terms "hydrophilic" or "hydrophobic" are relative terms.

The relative hydrophilicity or hydrophobicity of a surfactant may be expressed by its hydrophilic-lipophilic balance value ("HLB value). Surfactants with a lower HLB value are catagorized as being "hydrophobic" surfactants whereas surfactants with a higher HLB value are catagorized as being "hydrophilic" surfactants. As a rule of thumb, surfactants having a HLB value greater than about 10 are generally considered as being hydrophilic surfactants; surfactants having a HLB value lower than about 10 are generally considered as being hydrophobic surfactants.

The present compositions preferably comprise a hydrophilic surfactant. It should be appreciated that the HLB value of a surfactant is only a rough guide to indicate the hydrophilicity/hydrophobicity of a surfactant. The HLB value of a particular surfactant may vary depending upon the method used to determine the HLB value; may vary depending on its commercial source; is subject to batch to batch variability. A person skilled in the art can readily identify hydrophilic surfactants suitable for use in the pharmaceutical compositions of the present invention.

The surfactant of the present invention can be an anionic, a cationic, a zwitterionic or a non-ionic surfactant, the latter being preferred. The surfactant of the present invention can also be a mixture of two or more surfactants.

The choice of surfactant may be directed by the particular drug compound to be used in the composition of the invention. Thus the surfactant with greater solubilizing capacity for the particular drug compound, with an enhanced capacity to provide for a supersaturated condition, may be preferred.

Suitable surfactants for use in the compositions of the present invention are listed below. It should be emphasized that said list of surfactants is only illustrative, representative and not exhaustive. Thus the invention is not limited to the surfactants listed below. In the present compositions, also mixtures of surfactants may be used.

Suitable surfactants which may be used in the present invention comprise:

a) Polyethylene glycol fatty acid monoesters comprising esters of lauric acid, oleic acid, stearic acid, ricinoic acid and the like with PEG 6, 7, 8, 9, 10, 12, 15, 20, 25, 30, 32, 40, 45, 50, 55, 100, 200, 300, 400, 600 and the like, for instance PEG-6 laurate or stearate, PEG-7 oleate or laurate, PEG-8 laurate or oleate or stearate, PEG-9 oleate or stearate, PEG-10 laurate or oleate or stearate, PEG-12 laurate or oleate or stearate or ricinoleate, PEG-15 stearate or oleate, PEG-20 laurate or oleate or stearate, PEG-25 stearate, PEG-32 laurate or oleate or stearate, PEG-30 stearate, PEG40 laurate or oleate or stearate, PEG45 stearate, PEG-50 stearate, PEG-55 stearate, PEG-100 oleate or stearate, PEG-200 oleate, PEG400 oleate, PEG-600 oleate; (the surfactants belonging to this group are for instance known as Cithrol, Algon, Kessco, Lauridac, Mapeg, Cremophor, Emulgante, Nikkol, Myrj, Crodet, Albunol, Lactomul)

b) Polyethylene glycol fatty acid diesters comprising diesters of lauric acid, stearic acid, palmic acid, oleic acid and the like with PEG-8, 10, 12, 20, 32, 400 and the like, for instance PEG-8 dilaurate or distearate, PEG-10 dipalmitate, PEG-12 dilaurate or distearate or dioleate, PEG-20 dilaurate or distearate or dioleate PEG-32 dilaurate or distearate or dioleate, PEG400 dioleate or distearate; (the surfactants belonging to this group are for instance known as Mapeg, Polyalso, Kessco, Cithrol)

c) Polyethylene glycol fatty acid mono- and diester mixtures such as for example PEG 4-150 mono and dilaurate, PEG 4-150 mono and dioleate, PEG 4-150 mono and distearate and the like; (the surfactants belonging to this group are for instance known as Kessco)

d) Polyethylene glycol glycerol fatty acid esters such as for instance PEG-20 glyceryl laurate or glyceryl stearate or glyceryl oleate, PEG-30 glyceryl laurate or glyceryl oleate, PEG-15 glyceryl laurate, PEG-40 glyceryl laurate and the like; (the surfactants belonging to this group are for instance known as Tagat, Glycerox L, Capmul), e) Alcohol-oil transesterification products comprising esters of alcohols or polyalcohols such as glycerol, propylene glycol, ethylene glycol, polyethylene glycol, sorbitol, pentaerythritol and the like with natural and/or hydrogenated oils or oil-soluble vitamins such as castor oil, hydrogenated castor oil, vitamin A, vitamin D, vitamin E, vitamin K, an edible vegetable oil e.g. corn oil, olive oil, peanut oil, palm kernel oil, apricot kernel oil, almond oil and the like, such as PEG-20 castor oil or hydrogenated castor oil or corn glycerides or almond glycerides, PEG-23 castor oil, PEG-25 hydrogenated castor oil or trioleate, PEG-35 castor oil, PEG-30 castor oil or hydrogenated castor oil, PEG-38 castor oil, PEG-40 castor oil or hydrogenated castor oil or palm kernel oil, PEG45 hydrogenated castor oil, PEG-50 castor oil or hydrogenated castor oil, PEG-56 castor oil, PEG-60 castor oil or hydrogenated castor oil or corn glycerides or almond glycerides, PEG-80 hydrogenated castor oil, PEG-100 castor oil or hydrogenated castor oil, PEG-200 castor oil, PEG-8 caprylic/capric glycerides, PEG-6 caprylic/capric glycerides, lauroyl macrogol-32 glyceride, stearoyl macrogol glyceride, tocopheryl PEG-1000 succinate (TPGS); (the surfactants belonging to this group are for instance known as Emalex, Cremophor, Emulgante, Eumulgin, Nikkol, Thornley, Simulsol, Cerex, Crovol, Labrasol, Softigen, Gelucire, Vitamin E TPGS), f) polyglycerized fatty acids comprising polyglycerol esters of fatty acids such as for instance polyglyceryl-10 laurate or oleate or stearate, polyglyceryl-10 mono and dioleate, polyglyceryl polyricinoleate and the like; (the surfactants belonging to this group are for instance known as Nikkol Decaglyn, Caprol or Polymuls)

g) Sterol derivatives comprising polyethylene glycol derivatives of sterol such as PEG-24 cholesterol ether, PEG-30 cholestanol, PEG-25 phyto sterol, PEG-30 soya sterol and the like; (the surfactants belonging to this group are for instance known as Solulan™ or Nikkol BPSH)

h) Polyethylene glycol sorbitan fatty acid esters such as for example PEG-10 sorbitan laurate, PEG-20 sorbitan monolaurate or sorbitan tristearate or sorbitan monooleate or sorbitan trioleate or sorbitan monoisostearate or sorbitan monopaliniate or sorbitan monostearate, PEG-4 sorbitan monolaurate, PEG-5 sorbitan monooleate, PEG-6 sorbitan monooleate or sorbitan monolaurate or sorbitan monostearate, PEG-8 sorbitan monostearate, PEG-30 sorbitan tetraoleate, PEG40 sorbitan oleate or sorbitan tetraoleate, PEG-60 sorbitan tetrastearate, PEG-80 sorbitan monolaurate, PEG sorbitol hexaoleate (Atlas G-1086) and the like; (the surfactants belonging to this group are for instance known as Liposorb, Tween, Dacol MSS, Nikkol, Emalex, Atlas)

i) Polyethylene glycol alkyl ethers such as for instance PEG-10 oleyl ether or cetyl ether or stearyl ether, PEG-20 oleyl ether or cetyl ether or stearyl ether, PEG-9 lauryl ether, PEG-23 lauryl ether (laureth-23), PEG-100 stearyl ether and the like; (the surfactants belonging to this group are for instance known as Volpo, Brij)

j) Sugar esters such as for instance sucrose distearate/monostearate, sucrose monostearate or monopalmitate or monolaurate and the like; (the surfactants belonging to this group are for instance known as Sucro ester, Crodesta, Saccharose monolaurate)

k) Polyethylene glycol alkyl phenols such as for instance PEG-10-100 nonyl phenol (Triton X series), PEG-15-100 ocyl phenol ether (Triton N series) and the like;

l) Polyoxyethylene-polyoxypropylene block copolymers (poloxamers) such as for instance poloxamer 108, poloxamer 188, poloxamer 237, poloxamer 288 and the like; (the surfactants belonging to this group are for instance known as Synperonic PE, Pluronic, Emkalyx, Lutrol™, Supronic, Monolan, Pluracare, Plurodac)

m) ionic surfactants including cationic, anionic and zwitterionic surfactans such as the fatty acid salts e.g. sodium oleate, sodium lauryl sulfate, sodium lauryl sarcosinate, sodium dioctyl sulfosuccinate, sodium myristate, sodium palmitate, sodium state, sodium ricinoleate and the like; such as bile salts e.g. sodium cholate, sodium taurocholate, sodium glycocholate and the like; such as phospholipids e.g. egg/soy lecithin, hydroxylated lecithin, lysophosphatidylcholine, phosphatidylcholine, phosphatidyl ethanolamine, phosphatidyl glycerol, phosphatidyl serine and the like; such as phosphoric acid esters e.g. diethanolammonium polyoxyethylene-10 oleyl ether phosphate, esterification products of fatty alcohols or fatty alcohol ethoxylates with phosphoric acid or anhydride; such as carboxylates e.g. succinylated monoglycerides, sodium stearyl fumarate, stearoyl propylene glycol hydrogen succinate, mono/diacetylated tartaric acid esters of mono- and diglycerides, citric acid esters of mono- and diglycerides, glyceryl-lacto esters of fatty acids, lactylic esters of fatty acids, calcium/sodium stearoyl-2-lactylate, calcium/sodium stearoyl lactylate, alginate salts, propylene glycol alginate, ether carboxylates and the like; such as sulfates and sulfonates e.g. ethoxylated alkyl sulfates, alkyl benzene sulfates, alpha-olefin sulfonates, acyl isethionates, acyl taurates, alkyl glyceryl ether sulfonates, octyl sulfosuccinate disodium, disodium undecyleneamido-MEA-sulfosuccinate and the like; such as cationic surfactants e.g. hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (lauryl betaine), ethoxylated amines (polyoxyethylene-15 coconut amine) and the like.

When in the above list of suitable surfactants, different possibilities are listed such as for example PEG-20 oleyl ether or cetyl ether or stearyl ether, this means that PEG-20 oleyl ether and PEG-20 cetyl ether and PEG-20 stearyl ether are intended. Thus for instance PEG-20 castor oil or hydrogenated castor oil or corn glycerides or almond glycerides has to be read as PEG-20 castor oil and PEG-20 hydrogenated castor oil and PEG-20 corn glycerides and PEG-20 almond glycerides.

In the compositions of the invention, the surfactant is preferably present at 1 to 70% by weight, more preferably 5 to 55%, most preferably 10 to 50% by weight (relative to the total weight of surfactant, acid and drug). The quantity of surfactant used however will generally be dependent on the quantity of drug and on the drug compound itself. The weight by weight ratio of surfactant to drug will preferably lie in the range 100:1 to 1:5, especially 50:1 to 1:2, more especially 10:1 to 1:1.

Preferred surfactants in the present compositions belong to the group of the polyethylene glycol sorbitan fatty acid esters, the group of the alcohol-oil transesterification products or the group of the polyoxyethylene-polyoxypropylene block copolymers. More preferably, the surfactants in the present compositions belong to the group of the polyethylene glycol sorbitan fatty acid esters or the group of the alcohol-oil transesterification products. Most preferred surfactants are the surfactants known as Tween, the surfactants known as Cremophor, and Vitamin E TPGS (α-tocopheryl polyethylene glycol succinate, also abbreviated as TPGS), especially Cremophor RH 40 and Vitamin E TPGS.

As an alternative embodiment of the compositions of the present invention, the surfactant may be replaced by a suitable wax, such as for example polyethylene glycol and the like.

The acid used in the compositions of the invention may be any of the water-soluble physiologically tolerable acids, in particular any of the inorganic or, more preferably, organic acids conventionally used in the preparation of acid salts of drug compounds, e.g. citric, fumaric, tartaric, maleic, malic, succinic, oxalic, malonic, benzoic, mandelic and ascorbic acids.

Tartaric acid and more especially citric acid are preferred since the salts they form with drug compounds usually have a reduced tendency to precipitate from aqueous solutions. In general however, any acid which is not so strong as to cause degradation of the surfactant and yet which is capable, on the addition of water, of generating a low pH environment, preferably lower than pH 4 and ideally about pH 2, may be used. The acid may be in liquid (e.g. solution) or solid form; however acids which are solid at ambient conditions in their anhydrous or hydrate forms will generally be preferred.

The base used in the compositions of the invention may be any of the water-soluble physiologically tolerable bases, in particular any of the inorganic or, organic bases conventionally used in the preparation of alkaline salts of drug compounds, e.g. the alkali and earth alkaline metal bases, e.g. lithium-, sodium-, potassium-, magnesium- or calcium hydroxide, hydrocarbonate or carbonate and the like, $NH_3$, benzathine, N-methyl-D-glucamine, hydrabamine, ethanolamine, diethanolamine, triethanolamine and the like, amino acids such as, for example, arginine, lysine and the like.

In the compositions of the invention, the acid is present at a acid:drug ratio of at least 1:1 by weight, preferably the weight by weight ratio of acid:drug lies in the range of from 1:1 to 100:1, more preferably from 1:1 to 50:1, even more preferably from 1:1 to 10:1 and most preferred from 3:1 to 10:1. The amount of acid used will be dependent upon the selected acid and drug compound, but in general an increase in the relative proportion of acid will result in an acceleration of drug dissolution on contact with water. The amount of acid used will normally be at least the amount necessary to form an acidic microenvironment upon contact with water, in particular an aqueous body fluid, in which the solubility of the drug compound is increased.

The acid forms a significant proportion of the present compositions that dissolve rapidly in body fluids.

Therefore the present invention also relates to a pharmaceutical composition comprising a basic drug compound, a surfactant and a physiologically tolerable water-soluble acid characterized in that the weight by weight percentage of acid lies in the range from 30 to 95%, preferably from 45 to 95%, more preferably from 50 to 90%, most preferred from 50 to 65%. Preferably the weight by weight percentage is relative to the weight of the basic drug compound, the surfactant and the physiologically tolerable water-soluble acid and optionally the polymer.

Alternatively, the present invention also relates to a pharmaceutical composition comprising a basic drug compound, a surfactant and a physiologically tolerable water-soluble acid characterized in that the acid:drug compound molar ratio is at least 3:1, preferably at least 5:1, more preferably at least 10:1.

The present invention also relates to a pharmaceutical composition comprising a basic drug compound, a surfactant and a physiologically tolerable water-soluble acid characterized in that the weight by weight percentage of acid lies in the range from 30 to 95% and characterized in that the acid:drug compound ratio is at least 1:1 by weight. Alternatively, the present invention also relates to a pharmaceutical composition comprising a basic drug compound, a surfactant and a physiologically tolerable water-soluble acid characterized in that the weight by weight percentage of acid lies in the range from 30 to 95% and characterized in that the acid:drug compound molar ratio is at least 3:1.

The quantities specified above for the acid also account for the base in those compositions of the present invention which comprise an acidic drug compound, a surfactant and a base.

While the benefits of the compositions of the invention are most pronounced where the drug compound is no more than sparingly soluble, the drug dissolution profiles achievable using the combination of drug, surfactant and acid (or base) are such that particularly improved drug uptake profiles may be achieved even where the drug compound is more soluble.

Hence, the drug compound used in the compositions of the invention may be any organic or inorganic material. The drug compound may exert a local physiological effect, as well as a systemic effect, either after penetrating the mucosa or—in the case of oral administration—after transport to the gastrointestinal tract with saliva.

Preferably, the drug compound is no more than sparingly soluble, i.e. which is sparingly soluble, slightly soluble, very slightly soluble, or practically insoluble in pure water at 21° C. (i.e. requiring from 30, from 100, from 1000 or from 10000 parts water to put 1 part by weight drug compound into solution). In particular, the drug is a basic drug compound. The term basic drug compound defines a drug compound with a pKa value above 7 or a drug compound which may be solubilized in acid/acidic medium. The term acidic drug compound defines a drug compound with a pKa under 7 or a drug compound which may be solubilized in base/basic (alkaline) medium.

Examples of poorly water-soluble compounds that may be used in the compositions of the invention include nifedipine,
itraconazole (described in EP-A-6711),
saperconazole (see U.S. Pat. No. 4,916,134),
(−)-[2S-[2α,4α(S*)]]-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one (Compound 40 in WO96/13499),
cisapride (described in EP-A-76530),
(B)—N-[4-[2-ethyl-1-(1H-1,2,4-triazol-1-yl)butyl]phenyl]-2-benzothiazolamine (described in WO-97/49704); methyl 6,11-dihydro-11-[1-[2-[4-(2-quinolinylmethoxy)phenyl]ethyl]-4-piperidinylidene]-5H-imidazo[2,1-b][3]benzazepine-3-carboxylate (described in WO-97/34897);
4-[[4-amino-6-[(2,6-dichlorophenyl)methyl]-1,3,5-triazin-2-yl]amino]benzonitrile (described in EP-0.834.507);
(B-cis)-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylethyl)-2-imidazolidinone;
(2S-cis)-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylethyl)-2-imidazolidinone;
3-[2-[3,4-dihydrobenzofaro[3,2-c]pyridin-2(1H)-yl]ethyl]-2-methyl-4H-pyrido-[1,2-a]pyrimidin-4-one;
N-[2-[4-(4-chlorophenyl)-1-piperazinyl]ethyl]-2-benzothiazolamine;
(B1)-N-[4-[2-(dimethylamino)-1-(1H-imidazol-1-yl)propyl]phenyl]-2-benzothiazolamine (described in WO-97/49704)
(B)-6-[amino(4-chlorophenyl)(1-methyl-1H-imidazol-5-yl)methyl]-4-(3-chlorophenyl)-1-methyl-2(1H)-quinolinone;
(B)—N-[4-[2-ethyl-1-(1H-1,2,4-triazol-1-yl)butyl]phenyl]-2-benzothiazolamine;
3-[6-(dimethylamino)-4-methyl-3-pyridinyl]-2,5-dimethyl-N,N-dipropylpyrazolo-[2,3-a]pyrimidin-7-amine monohydrochloride;
(S)-[1-[2-[3-[(2,3-dihydro-1H-inden-2-yl)oxy]-4-methoxyphenyl]propyl]-1H-imidazol-2-yl]cyanamide;

(+)-(B-trans)-4-[1-[3,5-bis(trifluoromethyl)benzoyl]-2-(phenylmethyl)-4-piperidinyl]-N-(2,6-dimethylphenyl)-1-piperazineacetamide (S)-hydroxybutanedioate (1:1);

(−)-[2S-[2α,4α(S*)]]-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one;

(+)-(trans)-4-[1-[3,5-bis(trifluoromethyl)benzoyl]-2-(phenylmethyl)-4-piperidinyl]-N-(2,6-dimethylphenyl)-1-piperazine acetamide;

the compounds described in WO 99/50256, WO 00/27828, WO 01/85699, WO 01/85700, WO 01/64674 and EP 0,834,507; said documents incorporated herein by reference;

compounds of formula (1) (reference therefore is made to PCT/EP02/08953)

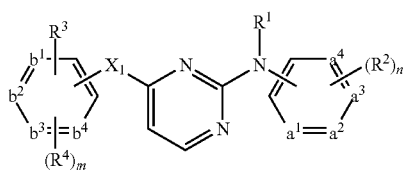
(I)

a N-oxide, a pharmaceutically acceptable addition salt, a quaternary amine or a stereochemically isomeric form thereof, wherein -a$^1$=a$^2$-a$^3$=a$^4$— represents a bivalent radical of formula —CH=CH—CH=CH— (a-1);

—N=CH—CH=CH— (a-2);

—N=CH—N=CH— (a-3);

—N=CH—CH=N— (a-4);

—N=N—CH=CH— (a-5);

-b$^1$=b$^2$-b$^3$=b$^4$— represents a bivalent radical of formula

—CH=CH—CH=CH— (b-1);

—N=CH—CH=CH— (b-2);

—N=CH—N=CH— (b-3);

—N=CH—CH=N— (b-4);

—N=N—CH=CH— (b-5);

n is 0, 1, 2, 3 or 4; and in case -a$^1$=a$^2$-a$^3$=a$^4$— is (a-1), then n may also be 5;

m is 1, 2, 3 and in case -b$^1$=b$^2$-b$^3$=b$^4$— is (b-1), then m may also be 4;

R$^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

each R$^2$ independently is hydroxy, halo, $C_{1-6}$alkyl optionally substituted with cyano or —C(=O)R$^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

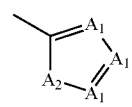
(c)

wherein each A$_1$ independently is N, CH or CR$^6$; and A$_2$ is NH, O, S or NR$^6$;

X$_1$ is —NR$^5$—, —NH—NH—, —N=N—, —O—, —C(=O)—, $C_{1-4}$alkanediyl, —CHOH—, —S—, —S(=O)$_p$—, —X$_2$—$C_{1-4}$alkanediyl- or —$C_{1-4}$alkanediyl-X$_2$—;

X$_2$ is —NR$^5$—, —NH—NH—, —N=N—, —O—, —C(=O)—, —CHOH—, —S—, —S(=O)$_p$—;

R$^3$ is NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; $C_{1-6}$alkyl substituted with one or more substituents each independently selected from cyano, NR$^9$R$^{10}$, —C(=O)—NR$^9$R$^{10}$, —C(=O)—$C_{1-6}$alkyl or R$^7$; $C_{1-6}$alkyl substituted with one or more substituents each independently selected from cyano, NR$^9$R$^{10}$, —C(=O)—NR$^9$R$^{10}$, —C(=O)—$C_{1-6}$alkyl or R$^7$ and wherein 2 hydrogen atoms bound at the same carbon atom are replaced by $C_{1-4}$alkanediyl; $C_{1-6}$alkyl substituted with hydroxy and a second substituent selected from cyano, NR$^9$R$^{10}$, —C(=O)—NR$^9$R$^{10}$, —C(=O)—$C_{1-6}$alkyl or R$^7$; $C_{1-6}$alkyloxy$C_{1-6}$alkyl optionally substituted with one or more substituents each independently selected from cyano, NR$^9$R$^{10}$, —C(=O)—NR$^9$R$^{10}$, —C(=O)—$C_{1-6}$alkyl or R$^7$; $C_{2-6}$alkenyl substituted with one or more substituents each independently selected from halo, cyano, NR$^9$R$^{10}$, —C(=O)—NR$^9$R$^{10}$, —C(=O)—$C_{1-6}$alkyl or R$^7$; $C_{2-6}$alkynyl substituted with one or more substituents each independently selected from halo, cyano, NR$^9$R$^{10}$, —C(=O)—NR$^9$R$^{10}$, —C(=O)—$C_{1-6}$alkyl or R$^7$; —C(=N—O—R$^8$)—$C_{1-4}$alkyl; R$^7$ or —X$_3$—R$^7$;

X$_3$ is —NR$^5$—, —NH—NH—, —N=N—, —O—, —C(=O)—, —S—, —S(=O)$_p$—, —X$_2$—$C_{1-4}$alkanediyl-, —$C_{1-4}$alkanediyl-X$_{2a}$—, —$C_{1-4}$alkanediyl-X$_{2b}$—$C_{1-4}$alkanediyl, —C(=N—OR$^8$)—$C_{1-4}$alkanediyl-;

with X$_{2a}$ being —NH—NH—, —N=N—, —O—, —C(=O)—, —S—, —S(=O)$_p$—; and with X$_{2b}$ being —NH—NH—, —N=N—, —C(=O)—, —S—, —S(=O)$_p$—;

R$^4$ is halo, hydroxy, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, $C_{1-6}$alkyloxycarbonyl, $C_{1-6}$alkylcarbonyl, formyl, amino, mono- or di($C_{1-4}$alkyl)amino or R$^7$;

R$^5$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl or $C_{1-6}$alkylcarbonyloxy; $C_{1-6}$alkyloxy$C_{1-6}$alkylcarbonyl substituted with $C_{1-6}$alkyloxycarbonyl;

R$^6$ is $C_{1-4}$alkyl, amino, mono- or di($C_{1-4}$alkyl)amino or polyhalo$C_{1-4}$alkyl;

R$^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$alkyl;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$);

$R^8$ is hydrogen, $C_{1-4}$alkyl, aryl or aryl$C_{1-4}$alkyl;

$R^9$ and $R^{10}$ each independently are hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(=N$R^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxyC, alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, —S(=O)$_p R^6$, —NH—S(=O)$_p R^6$, —C(=O)$R^6$, —NHC(=O)H, —C(=O)NHNH$_2$, —NHC(=O)$R^6$, —C(=NH)$R^6$, $R^7$; or $R^9$ and $R^{10}$ may be taken together to form a bivalent or trivalent radical of formula —CH$_2$—CH$_2$—CH$_2$—CH$_2$— (d-1)

—CH$_2$—CH$_2$—CH$_2$—CH$_2$—CH$_2$— (d-2)

—CH$_2$—CH$_2$—O—CH$_2$—CH$_2$— (d-3)

—CH$_2$—CH$_2$—S—CH$_2$—CH$_2$— (d4)

—CH$_2$—CH$_2$—N$R^{12}$—CH$_2$—CH$_2$— (d-5)

—CH$_2$—CH=CH—CH$_2$— (d-6)

=CH—CH=CH—CH=CH— (d-7)

$R^{11}$ is cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ is hydrogen or $C_{1-4}$alkyl;

$R^{13}$ and $R^{14}$ each independently are $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ is $C_{1-6}$alkyl substituted with cyano or aminocarbonyl;

$R^{16}$ is $C_{1-6}$alkyl optionally substituted with cyano or aminocarbonyl, or $R^7$;

p is 1 or 2;

aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$;

compounds as described in WO99/50250 incorporated herein as reference, namely compounds of formula (I-A)

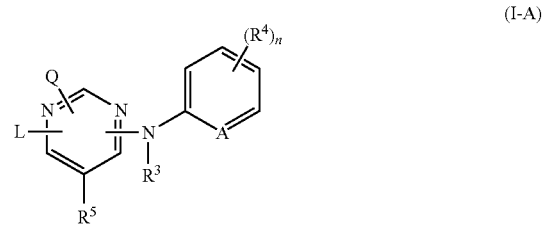

(I-A)

a N-oxide, a pharmaceutically acceptable addition salt or a stereochemically isomeric form thereof, wherein A is CH, $CR^4$ or N;

n is 0, 1, 2, 3 or 4;

Q is hydrogen or —$NR^1R^2$;

$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{1-12}$alkyl)amino$C_{1-4}$alkylidene;

$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and each $R^4$ independently is hydroxy, halo, $C_{1-6}$alkyl, $C_{1-6}$alkyloxy, cyano, aminocarbonyl, nitro, amino, trihalomethyl, trihalomethyloxy or $C_{1-6}$alkyl substituted with cyano or aminocarbonyl;

$R^5$ is hydrogen or $C_{1-4}$alkyl;

L is $C_{1-10}$alkyl, $C_{3-10}$alkenyl, $C_{3-10}$-alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl; or L is —$X^1$—$R^6$ or —$X^2$-Alk-$R^7$ wherein $R^6$ and $R^7$ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, aminocarbonyl, nitro, amino, trihalomethyloxy and trihalomethyl; and $X^1$ and $X^2$ are each independently —$NR^3$—, —NH—NH—, —N=N—, —O—, —S—, —S(=O)— or —S(=O)$_2$—;

Alk is $C_{1-4}$alkanediyl;

aryl is phenyl or phenyl substituted with one, two, three, four or five substituents each independently selected from halo, $C_{1-6}$alkyl, $C_{1-6}$alkyloxy, cyano, nitro and trifluoromethyl;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy;

compounds described in WO 00/27825 incorporated herein as reference, namely compounds of formula (I-B)

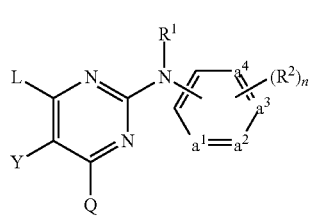

(I-B)

the N-oxides, the pharmaceutically acceptable addition salts, the quaternary amines and the stereochemically isomeric forms thereof, wherein -$a^1$=$a^2$-$a^3$=$a^4$— represents a bivalent radical of formula

 (a-1);

 (a-2);

 (a-3);

 (a4);

 (a-5);

n is 0, 1, 2, 3 or 4; and in case -$a^1$=$a^2$-$a^3$=$a^4$— is (a-1), then n may also be 5;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

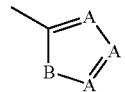

(c)

wherein each A independently is N, CH or CR$^6$;

B is NH, O, S or NR$^6$;

p is 1 or 2; and $R^6$ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or L is —X—$R^3$ wherein $R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$; and X is —$NR^1$—, —NH—NH—, —N=N—, —O—, —C(=O)—, —CHOH—, —S—, —S(=O)— or —S(=O)$_2$—;

Q represents hydrogen, $C_{1-6}$alkyl, halo, polyhalo$C_{1-6}$alkyl or —$NR^4R^5$; and $R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$, aryl and Het; or $R^4$ and $R^5$ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^6$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or aryl;

aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy;

Particular compounds of formula (1) are compounds 1, 25, 84, 133, 152, 179, 233, 239, 247, 248 (see Tables 3, 4 and 5), their N-oxides, pharmaceutically acceptable addition salts, quaternary amines and stereochemically isomeric forms thereof.

Most preferred compound of formula (I) is:
4-[[4-[[4-(2-cyanoethenyl)-2,6-dimethylphenyl]amino]-2-pyrimidinyl]amino]-benzonitrile;
a N-oxide, an addition salt, a quaternary amine or a stereochemically isomeric form thereof.

Particular compounds of formula (I-A) are:
4-[[4-amino-6-[(2,6-dichlorophenyl)methyl]-2-pyrimidinyl]amino]benzonitrile;
6-[(2,6-dichlorophenyl)methyl]-N2-(4-fluorophenyl)-2,4-pyrimidinediamine;
4-[[4-[(2,4-dichlorophenyl)methyl]-6-[(4-hydroxybutyl)amino]-2-pyrimidinyl]amino]-benzonitrile;
4-[[4-[(2,6-dichlorophenyl)methyl]-6-[(3-hydroxypropyl)amino]-2-pyrimidinyl]amino]-benzonitrile;
N-[2-[(4-cyanophenyl)amino]-6-[(2,6-dichlorophenyl)methyl]-4-pyrimidinyl]-acetamide;
N-[2-[(4-cyanophenyl)amino]-6-[(2,6-dichlorophenyl)methyl]-4-pyrimidinyl]-butanamide;
4-[[2-amino-6-(2,6-dichlorophenoxy)-4-pyrimidinyl]amino]benzonitrile;
4-[[4-[(2,6-dichlorophenyl)methyl]-6-[(2-hydroxy-2-phenylethyl)amino]-2-pyrimidinyl]amino]benzonitrile;
4-[[4-[(2,6-dichlorophenyl)methyl]-6-[[3-(2-oxo-1-pyrrolidinyl)propyl]amino]-2-pyrimidinyl]amino]benzonitrile;
4-[[4-[(2,6-dichlorophenyl)methyl]-6-[[2-(2-hydroxyethoxy)ethyl]amino]-2-pyrimidinyl]amino]benzonitrile;
4-[[4-[(2,6-dichlorophenyl)methyl]-6-[(2,3-dihydroxypropyl)amino]-2-pyrimidinyl]-amino]benzonitrile;
4-[[4-[(2,6-diclorophenyl)methyl]-6-(hydroxyamino)-2-pyrimidinyl]amino]-benzonitrile;
4-[[4-[(2-cyanoethyl)amino]-6-[(2,6-dichlorophenyl)methyl]-2-pyrimidinyl]amino]-benzonitrile;
4-[[4-[(2,6-dichlorophenyl)methyl]-6-[[2-(1-pyrrolidinyl)ethyl]amino]-2-pyrimidinyl]-amino]benzonitrile;
4-[[4-amino-6-[(2,6-dichlorophenyl)methyl]-5-methyl-2-pyrimidinyl]amino]-benzonitrile;
N2-(4-bromophenyl)-6-[(2,6-dichlorophenyl)methyl]-5-methyl-2,4-pyrimidinediamine;
4-[[4-[(2,4,6-trimethylphenyl)amino]-2-pyrimidinyl]amino]benzonitrile;
4-[[2-[(2,4,6-trimethylphenyl)amino]-4-pyrimidinyl]amino]benzonitrile;
4-[[4-[(2,6-dimethylphenyl)amino]-2-pyrimidinyl]amino]benzonitrile;
4-[[4-(2,4,6-trimethylphenoxy)-2-pyrimidinyl]amino]benzonitrile;
4-[[4-[(2,6-dichlorophenyl)thio]-2-pyrimidinyl]amino]benzonitrile;
4-[[4-[[2,6-dibromo-4-(1-methylethyl)phenyl]amino]-2-pyrimidinyl]amino]-benzonitrile;
4-[[4-[[2,6-dichloro-4-(trifluoromethyl)phenyl]amino]-2-pyrimidinyl]amino]-benzonitrile;
4-[[4-[(2,4-dichloro-6-methylphenyl)amino]-2-pyrimidinyl]amino]benzonitrile;
4-[[2-[(cyanophenyl)amino]-4-pyrimidinyl]amino]-3,5-dimethylbenzonitrile;
4-[[4-[(2,4-dibromo-6-fluorophenyl)amino]-2-pyrimidinyl]amino]benzonitrile;
4-[[4-amino-6-[(2,6-dichlorophenyl)methyl]-5-methyl-2-pyrimidinyl]amino]-benzeneacetonitrile;
4-[[4-[methyl(2,4,6-trimethylphenyl)amino]-2-pyrimidinyl]amino]benzonitrile;
4-[[4-[(2,4,6-trichlorophenyl)amino]-2-pyrimidinyl]amino]benzonitrile;
4-[[4-[(2,4,6-trimethylphenyl)thio]-2-pyrimidinyl]amino]benzonitrile;
4-[[4-(2,4,6-trimethylphenyl)amino-2-pyrimidinyl]amino]benzonitrile;
4-[[4-amino-6-[(2,4,6-trimethylphenyl)amino]-2-pyrimidinyl]amino]benzonitrile;
4-[[2-amino-6-[(2,4,6-trimethylphenyl)amino]-4-pyrimidinyl]amino]benzonitrile;
4-[[4-(2-bromo-4-chloro-6-methylphenoxy)-2-pyrimidinyl]amino]benzonitrile;
4-[[4-[(4-chloro-2,6-dimethylphenyl)amino]-2-pyrimidinyl]amino]benzonitrile;
3,5-dichloro-4-[[2-[(4-cyanophenyl)amino]-4-pyrimidinyl]amino]benzonitrile;
4-[[4-[[2,6-dichloro-4-(trifluoromethoxy)phenyl]amino]-2-pyrimidinyl]amino]-benzonitrile;
4-[[4-[(2,4-dibromo-3,6-dichlorophenyl)amino]-2-pyrimidinyl]amino]benzonitrile;
4-[[4-[(2,6-dibromo-4-propylphenyl)amino]-2-pyrimidinyl]amino]benzonitrile;
4-[[4-[(2,4,6-trimethylphenyl)amino]-2-pyrimidinyl]amino]benzamide;
4-[[4-[(4-(1,1-dimethylethyl)-2,6-dimethylphenyl)amino]-2-pyrimidinyl]amino]-benzonitrile;
4-[[2-[(4-cyanophenyl)amino]-4-pyrimidinyl]oxy]-3,5-dimethylbenzonitrile;
4-[[4-[(4-chloro-2,6-dimethylphenyl)amino]-5-methyl-2-pyrimidinyl]amino]-benzonitrile;
4-[[2-[(4-cyanophenyl)amino]-5-methyl-4-pyrimidinyl]amino-3,5-dimethylbenzonitrile;
4-[[4-[[4-(1,1-dimethylethyl)-2,6-dimethylphenyl]amino]-5-methyl-2-pyrimidinyl]-amino]benzonitrile;
4-[[4-[(4-bromo-2,6-dimethylphenyl)amino]-5-methyl-2-pyrimidinyl]amino]-benzonitrile;
4-[[5-methyl-4-[(2,4,6-trimethylphenyl)thio]-2-pyrimidinyl]amino]benzonitrile;
4-[[4-[(2,6-dibromo-4-propylphenyl)amino]-5-methyl-2-pyrimidinyl]amino]-benzonitrile;
4-[[4-[(2,4,6-trimethylphenyl)amino]-2-pyrimidinyl]amino]benzamide, N3-oxide;
N2-(4-chlorophenyl)-N4-(2,4,6-trimethylphenyl)-2,4-pyrimidinediamine;
4-[[4-[[2,6-dibromo-4-(1-methylethyl)phenyl]amino]-5-methyl-2-pyrimidinyl]amino]-benzonitrile;
4-[[2-[(4-cyanophenyl)amino]-5-methyl-4-pyrimidinyl]amino-3,5-dimethylbenzonitrile;

4-[[4-[(phenylmethyl)amino]-2-pyrimidinyl]amino]benzonitrile;

a N-oxide, a pharmaceutically acceptable addition salt or a stereochemically isomeric form thereof.

Most preferred compounds of formula (I-A) are:

4-[[2-[(cyanophenyl)amino]-4-pyrimidinyl]amino]-3,5-dimethylbenzonitrile; or

4-[[4-[(2,4,6-trimethylphenyl)amino]-2-pyrimidinyl]amino]benzonitrile;

a N-oxide, a pharmaceutically acceptable addition salt or a stereochemically isomeric form thereof.

Particular compounds of formula (I-B) are:

4-[[4-amino-5-chloro-6-[(2,4,6-trimethylphenyl)amino]-2-pyrimidinyl]amino]-benzonitrile;

4-[[5-chloro-4-[(2,4,6-trimethylphenyl)amino]-2-pyrimidinyl]amino]benzonitrile;

4-[[5-bromo-4-(4-cyano-2,6-dimethylphenoxy)-2-pyrimidinyl]amino]benzonitrile;

4-[[4-amino-5-chloro-6-[(4-cyano-2,6-dimethylphenyl)amino]-2-pyrimidinyl]amino]-benzonitrile;

4-[[5-bromo-6-[(4-cyano-2,6-dimethylphenyl)amino]-2-pyrimidinyl]amino]-benzonitrile;

4-[[4-amino-5-chloro-6-(4-cyano-2,6-dimethylphenyloxy)-2-pyrimidinyl]amino]-benzonitrile; or 4-[[4-amino-5-bromo-6-(4-cyano-2,6-dimethylphenyloxy)-2-pyrimidinyl]amino]-benzonitrile;

a N-oxide, an addition salt, a quaternary amine or a stereochemically isomeric form thereof.

Most preferred compound of formula (I-B) is:

4-[[4-amino-5-bromo-6-(4-cyano-2,6-dimethylphenyloxy)-2-pyrimidinyl]amino]-benzonitrile;

a N-oxide, an addition salt, a quaternary amine or a stereochemically isomeric form thereof.

Other suitable drug compounds in the compositions of the present invention are analgesic and anti-inflammatory drugs (NSAIDs, fentanyl, indomethacin, ibuprofen, ketoprofen, nabumetone, paracetamol, piroxicam, tramadol, COX-2 inhibitors such as celecoxib and rofecoxib);

anti-arrhythmic drugs (procainamide, quinidine, verapamil);

antibacterial and antiprotozoal agents (amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, norfloxacin, ofloxacin, oxacillin, phenoxymethylpenicillin potassium, pyrimethamine-sulfadoxime, streptomycin);

anti-coagulants (warfarin);

antidepressants (amitriptyline, amoxapine, butriptyline, clomipramine, desipramine, dothiepin, doxepin, fluoxetine, reboxetine, aminiptine, selegiline, gepirone, imipramine, lithium carbonate, mianserin, milnacipran, nortriptyline, paroxetine, sertraline; 3-[2-[3,4-dihydrobenzofuro[3,2-c]pyridin-2(1H)-yl]ethyl]-2-methyl-4H-pyrido[1,2-a]pyrimidin-4-one);

anti-diabetic drugs (glibenclamide, metformin, RWJ-394718, RWJ-394720, RWJ-666589, RWJ-37082), anti-epileptic drugs (carbamazepine, clonazepam, ethosuximide, gabapentin, lamotrigine, levetiracetam, phenobarbitone, phenytoin, primidone, tiagabine, topiramate, valpromide, vigabatrin);

antifungal agents (amphotericin, clotrimazole, econazole, fluconazole, flucytosine, griseofulvin, itraconazole, ketoconazole, miconazole nitrate, nystatin, terbinafine, voriconazole, echinocandins);

antihistamines (astemizole, cinnarizine, cyproheptadine, decarboethoxyloratadine, fexofenadine, flunarizine, levocabastine, loratadine, norastemizole, oxatomide, promethazine, terfenadine, cetirizine);

anti-hypertensive drugs (captopril, enalapril, ketanserin, lisinopril, minoxidil, prazosin, ramipril, reserpine, terazosin);

anti-muscarinic agents (atropine sulphate, hyoscine);

antineoplastic agents and antimetabolites (platinum compounds, such as cisplatin, carboplatin; taxanes, such as paclitaxel, docetaxel; tecans, such as camptothecin, irinotecan, topotecan; vinca alkaloids, such as vinblastine, vindecine, vincristine, vinorelbine; nucleoside derivatives and folic acid antagonists such as 5-fluorouracil, capecitabine, gemcitabine, mercaptopurine, thioguanine, cladribine, methotrexate; alkylating agents, such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics, such as daunorubicin, doxorubicin, idarubicin, epirubicin, bleomycin, dactinomycin, mitomycin; HER 2 antibody, such as trastuzumab; podophyllotoxin derivatives, such as etoposide, teniposide; farnesyl transferase inhibitors, e.g. zarnestra; anthrachinon derivatives, such as mitoxantron); imatinib; bortezomib;

anti-migraine drugs (alniditan, naratriptan, sumatriptan, almotriptan);

anti-Parkinsonian drugs (bromocryptine mesylate, levodopa, selegiline, rasagiline);

antipsychotic, hypnotic and sedating agents (alprazolam, amisulpride, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem, bromperidol, fluperidol, haloperidol, quetiapine, aripiprazole);

anti-stroke agents (lubeluzole, lubeluzole oxide, riluzole, aptiganel, eliprodil, remacemide);

antitussive (dextromethorphan, laevodropropizine);

antivirals (acyclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea, darunavir);

beta-adrenoceptor blocking agents (atenolol, carvedilol, metoprolol, nebivolol, propanolol);

cardiac inotropic agents (amrinone, digitoxin, digoxin, milrinone), corticosteroids (beclomethasone dipropionate, betamethasone, budesonide, dexamethasone, hydrocortisone, methylprednisolone, prednisolone, prednisone, triamcinolone);

disinfectants (chlorhexidine);

diuretics (acetazolamide, frusemide, hydrochlorothiazide, isosorbide);

enzymes;

essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme);

gastro-intestinal agents (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, sulphasalazine, esomeprazole);

haemostatics (aminocaproic acid);

lipid regulating agents (atorvastatin, lovastatin, pravastatin, probucol, simvastatin, rosuvastatin);

local anaesthetics (benzocaine, lignocaine), opioid analgesics (buprenorphine, codeine, dextromoramide, dihydrocodeine, hydrocodone, oxycodone, morphine);

parasympathomimetics and anti-dementia drugs (leteprinim, eptastigmine, galantamine, metrifonate, milameline, neostigmine, physostigmine, tacrine, donepezil, rivastigmine, sabcomeline, talsaclidine, xanomeline, memantine, lazabemide);

peptides and proteins (antibodies, becaplermin, cyclosporine, erythropoietin, immunoglobulins, insuline, growth factors, botulinum toxin, infliximab);

sex hormones (oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone, quingestanol acetate);

stimulating agents (sildenafil, tadalafil, apomorphine, vardenafil);

vasodilators (amlodipine, buflomedil, amyl nitrite, diltiazem, dipyridamole, glyceryl trinitrate, isosorbide dinitrate, lidoflazine, molsidomine, nicardipine, nifedipine, oxypentifylline, pentaerythritol tetranitrate);

their N-oxides, their pharmaceutically acceptable acid or base addition salts or their stereochemically isomeric forms.

Other examples include the following:

| 8-Methoxypsoralen | lithium salts | phytomenadione |
| Allopurinol | magnesium salts | propylthiouracil |
| alpha-Tocopherol | menadione | |
| iron salts | methylthiouracil | |

Drug compounds suitable for use in the compositions of the invention include drugs of all types conventionally administered topically (e.g. in a gel patch) or into an externally voiding body duct, e.g. orally, nasally, aurally, rectally or vaginally. Such drugs include in particular antifungals, calcium channel blockers, antibacterials, antihypertensives, antivirals, analgesics, apolipoprotein B synthesis inhibitors, and drugs which modify transit of gastro-intestinal tract contents (e.g. antidiarrhoea agents or motility promoters).

The invention is particularly applicable to anti-HIV agents, in particular non-nucleoside reverse transcriptase inhibitors, more in particular non-nucleoside reverse transcriptase inhibiting pyrimidine derivatives.

The compositions of the invention may conveniently contain the drug compound at 0.001 to 50% by weight, preferably 0.1 to 35%, more preferably 0.5 to 30%, especially 8 to 25% and most especially 10 to 15% by weight (relative to the total weight of acid (base), surfactant and drug compound). The quantity of drug will of course depend upon the desired dissolution profile, the intrinsic solubility of the drug compound and the drug dosage required where the drug is to be delivered in dosage units (e.g. capsules, coated tablets, etc).

In the compounds of formula (I), (I-A) or (I-B), $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

For therapeutic use, salts of the drug compounds are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the drug compounds are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxy-propanoic, 2-oxopropanoic, oxalic, malonic, succinic, maleic, fumaric, maleic, tartaric, 2-hydroxy-1,2,3-propanetricarboxylic, methanesulfonic, ethanesulfonic, benzene-sulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The drug compounds containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the drug compounds are able to form. Examples of such forms are e.g. hydrates, alcoholates and the like.

The term "quaternary amine" as used hereinbefore defines the quaternary ammonium salts which the drug compounds are able to form by reaction between a basic nitrogen of a drug compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms are meant to comprise the drug compounds wherein one or several tertiary nitrogen atoms are oxidized to the so-called N-oxide.

It will be appreciated that some of the drug compounds and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the drug compounds, and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the drug compounds are obviously intended to be embraced within the scope of this invention.

Some of the drug compounds may also exist in their tautomeric form. Such forms although not explicitly indicated in the above formula are intended to be included within the scope of the present invention.

The compounds of formula (I) can be prepared by reacting an intermediate of formula (II) wherein $W_1$ is a suitable leaving group such as, for example, halo, triflate, tosylate, methylsulfonyl and the like, with an intermediate of formula (III). This reaction can be performed at elevated temperature.

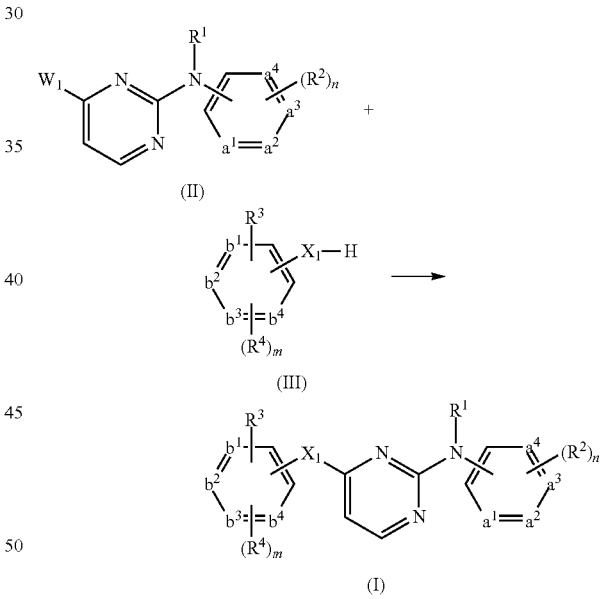

Alternatively, the above reaction can be performed in the presence of a suitable solvent. Suitable solvents are for example acetonitrile, an alcohol, such as for example ethanol, 2-propanol, 2-propanol-HCl; N,N-dimethylformamide; N,N-dimethylacetamide,1-methyl-2-pyrrolidinone; 1,4-dioxane, propyleneglycol monomethylether. Preferably the solvent is 2-propanol, 6 N HCl in 2-propanol or acetonitrile, especially acetonitrile. Optionally, sodium hydride may be present.

In this and the following preparations, the reaction products may be isolated from the reaction medium and, if necessary, further purified according to methodologies generally known in the art such as, for example, extraction, crystallization, distillation, trituration and chromatography.

Compounds of formula (I) wherein $R^3$ is $R^7$ representing a monocyclic, bicyclic or tricyclic aromatic ring system, said $R^3$ being represented by $R^{7'}$ and said compounds being represented by formula (I-a), can be prepared by reacting an intermediate of formula (II) wherein $W_2$ represents a suitable leaving group such as, for example, halo, hydroxy, triflate, tosylate, thiomethyl, methylsulfonyl, trifluoromethylsulfonyl and the like, with an intermediate of formula (V) wherein $R^a$ represents a boronate or a tri($C_{1-4}$alkyl)stannane, such as tributylstannane, in the presence of a suitable catalyst, such as for example palladium tetrakis(triphenylphosphine), a suitable salt, such as for example disodium carbonate, dipotassium carbonate, and $Cs_2CO_3$, and a suitable solvent, such as for example dioxane, dimethyl ether, toluene or an alcohol/water mixture, e.g. MeOH/$H_2O$. $R^a$ may also represent halo, such as for example bromo, in which case the reaction is performed in the presence of 4,4,4',4',5,5,5',5'-octamethyl-2,2'-bi-1,3,2-dioxaborolane.

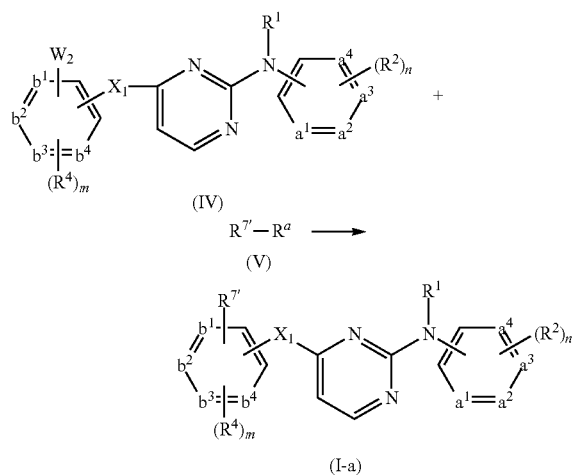

Compounds of formula (I) wherein $R^3$ is $R^7$ representing a monocyclic, bicyclic or tricyclic saturated ring system, said $R^3$ being represented by $R^{7''}$ and said compounds being represented by formula (I-b), can be prepared by reacting an intermediate of formula (IV) with an intermediate of formula (VI).

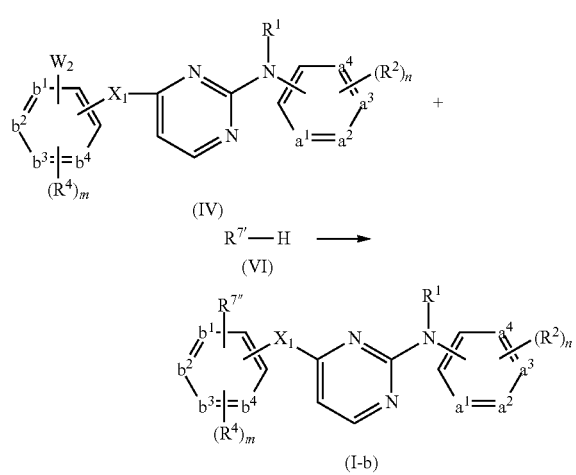

Compounds of formula (I) wherein $R^3$ represents $C_{1-6}$alkyl substituted with cyano, said $R^3$ being represented by $C_{1-6}$alkyl-CN and said compounds being represented by formula (I-c), can be prepared by reacting an intermediate of formula (VII) wherein $W_3$ represents a suitable leaving group, such as for example, halo, e.g. chloro, with a suitable cyanide salt, such as for example sodium cyanide or potassium cyanide, in the presence of a suitable solvent, such as for example N,N-dimethylformamide or dimethylsulfoxide.

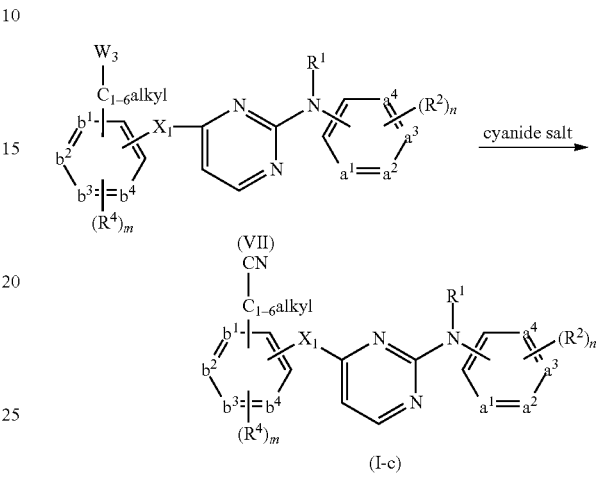

Compounds of formula (I) wherein $R^3$ represents $C_{1-6}$alkyl substituted with $R^7$; $NR^9R^{10}$ or $C_{1-6}$alkyloxy optionally substituted with CN, $R^7$ or $NR^9R^{10}$, said $R^3$ being represented by $C_{1-6}$alkyl-Q wherein Q represents $R^7$; $NR^9R^{10}$ or $C_{1-6}$alkyloxy optionally substituted with CN, $R^7$ or $NR^9R^{10}$, and said compounds being represented by formula (I-d), can be prepared by reacting an intermediate of formula (VII) with an intermediate of formula (VIII), optionally in the presence of a suitable salt, such as for example dipotassium carbonate, potassium cyanide, potassium iodide, and a suitable solvent, such as for example acetonitrile.

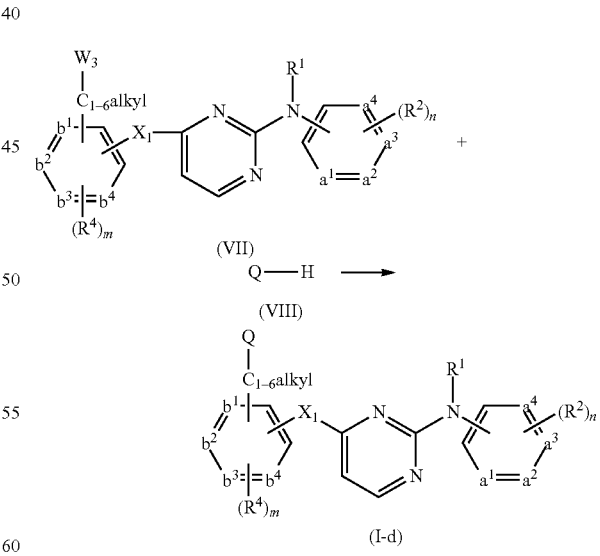

Compounds of formula (I) wherein $R^3$ represents $-C(=N-O-R^8)-C_{1-4}$alkyl, said compounds being represented by formula (I-e), can be prepared by reacting an intermediate of formula (IX) with an intermediate of formula (X) in the presence of a suitable solvent, such as an alcohol, e.g. ethanol.

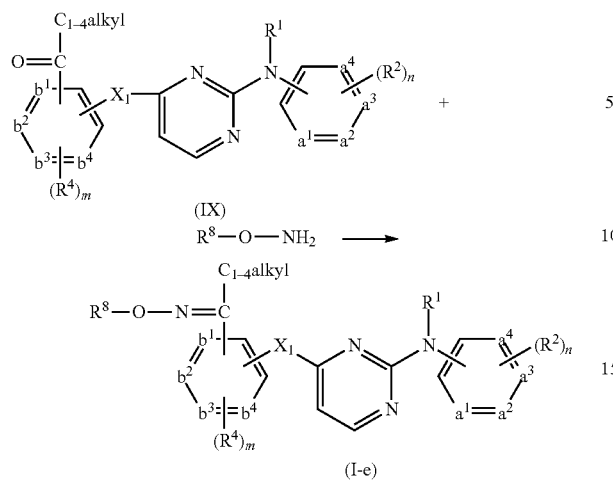

(IX)

$R^8$—O—$NH_2$ ⟶

(I-e)

Compounds of formula (I) wherein $R^3$ represents $CR^{c'}$=$CR^c$—CN wherein $R^c$ represents hydrogen or $C_{1-4}$alkyl and $R^{c'}$ represents hydrogen, $C_{1-4}$alkyl or $R^7$, provided that $CR^{c'}$=$CR^c$ is limited to $C_{2-6}$alkenyl, said compounds being represented by formula (I-f), can be prepared by reacting an intermediate of formula (XI) with a Wittig or Horner-Emmons reagent of formula (XII), wherein $R^b$— represents for example $(Phenyl)_3P^+$—$Cl^-$ or $(CH_3CH_2$—$O)_2P$ (=O)—, which can be considered as a suitable precursor of a phosphorus ylide, in the presence of a suitable salt, such as for example potassium tert.-butoxide, and a suitable solvent, such as for example tetrahydrofuran.

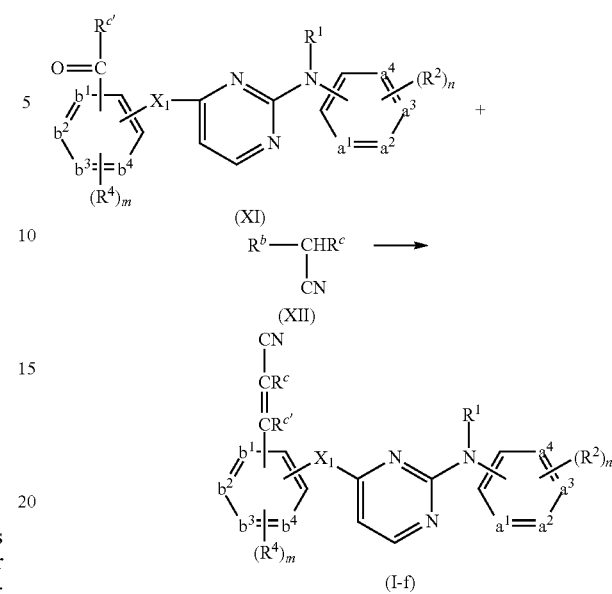

(XI)

$R^b$—$CHR^c$
|
CN (XII)

(I-f)

Compounds of formula (I-f-1) and (I-f-2) as depicted below can be prepared by reacting an intermediate of formula (XXXIX) or an appropriate addition salt thereof, wherein $W_5$ represents a suitable leaving group, with acrylonitrile or acrylamide in the presence of a suitable palladium catalyst, a suitable base and a suitable solvent.

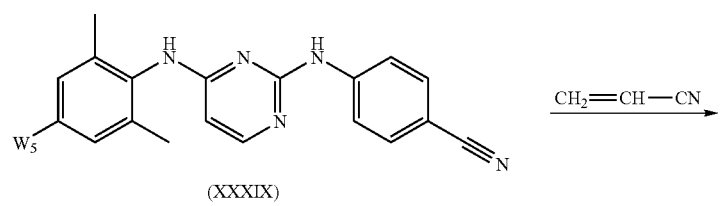

(XXXIX)

$CH_2$=CH—CN ⟶

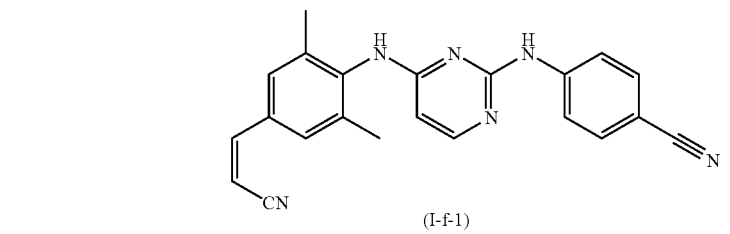

(I-f-1)

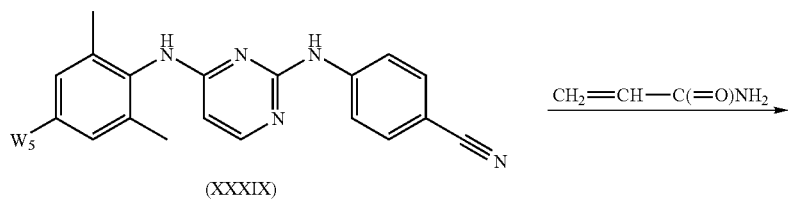

(XXXIX)

$CH_2$=CH—C(=O)$NH_2$ ⟶

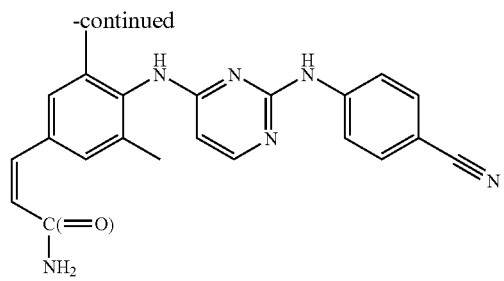

(I-f-2)

Suitable leaving groups in the above reaction are for example halo, triflate, tosylate, mesylate and the like. Preferably, $W_5$ is halo, more particularly iodo or bromo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, bis(dibenzylidene acetone) palladium, palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases in the above reaction are for example sodium acetate, potassium acetate, N,N-diethylethanamine, sodium hydrogencarbonate, sodium hydroxide and the like.

Suitable solvents in the above reaction are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

Compounds of formula (I) wherein $R^3$ represents $CR^c$=$CR^{c''}$—CN with $R^c$ being as defined hereinabove and $R^{c''}$ representing $NR^9R^{10}$, —C(=O)—$NR^9R^{10}$, —C(=O)—$C_{1-6}$alkyl or $R^7$, said compounds being represented by formula (I-g), can be prepared by reacting an intermediate of formula (XI-a) with an intermediate of formula (XIII) in the presence of a suitable solvent, such as for example an alcohol and an alcoholate, e.g. methanol and sodium ethanolate.

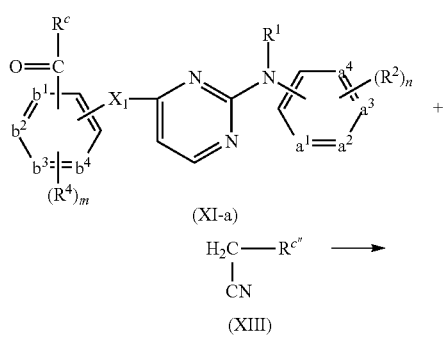

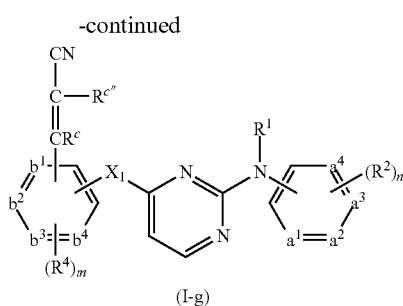

(I-g)

Compounds of formula (I) wherein $R^3$ represents CH=C(CN)—$CH_2$—CN, said compounds being represented by formula (I-h), can be prepared by reacting an intermediate of formula (XI-b) with 2-butenedinitrile in the presence of tributylphosphine and a suitable solvent, such as for example tetrahydrofuran.

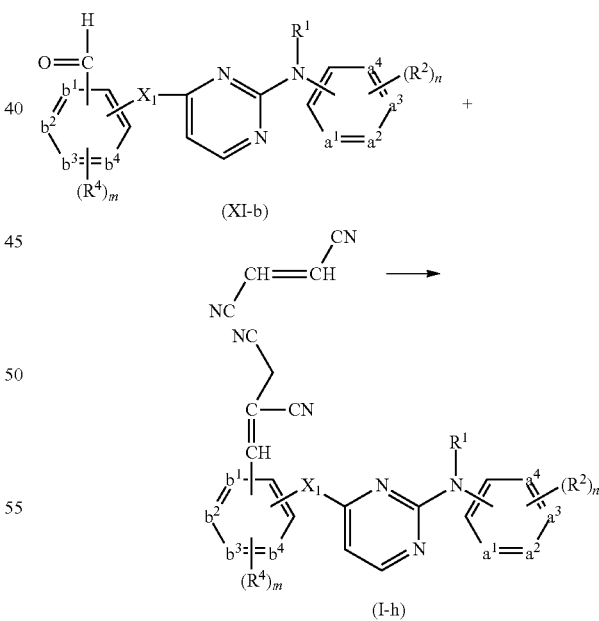

(I-h)

Compounds of formula (I) wherein $R^3$ represents CH=C$(CN)_2$, said compounds being represented by formula (I-h'), can be prepared by reacting an intermediate of formula (XI-b) with propanedinitrile in the presence of a suitable base, such as for example piperidine, and a suitable solvent, such as for example an alcohol, e.g. ethanol and the like.

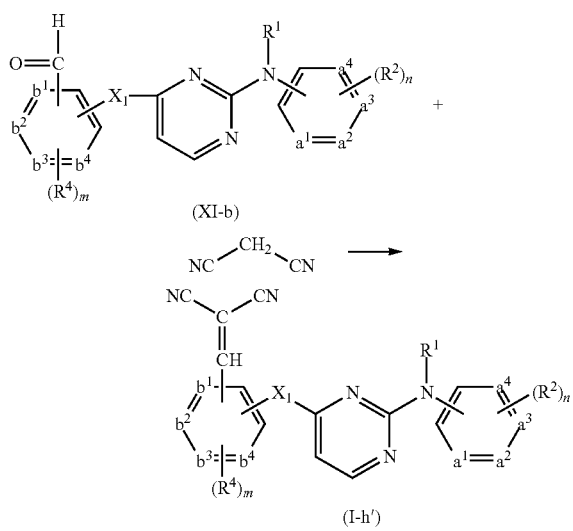

Compounds of formula (I) wherein R³ represents —CHOH—CH₂—CN, said compounds being represented by formula (I-i), can be prepared by reacting an intermediate of formula (XI-b) with CH₃—CN in the presence of a suitable proton-abstracting agent, such as for example butyl lithium, in the presence of a suitable substrate for the proton-abstracting agent, for example N-(1-methylethyl)-2-propanamine, and in the presence of a suitable solvent, such as for example tetrahydrofuran.

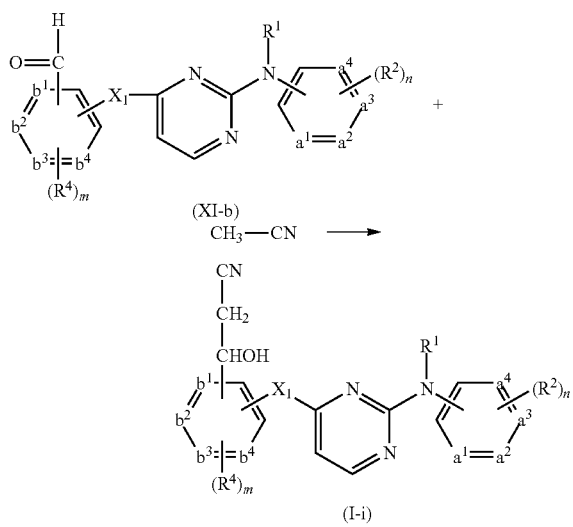

Compounds of formula (I) wherein R³ represents CR$^{c'}$=CR$^c$-halo wherein R$^c$ represents hydrogen or C$_{1-4}$alkyl and R$^{c'}$ represents hydrogen, C$_{1-4}$alkyl or R⁷, provided that CR$^{c'}$=CR$^c$ is limited to C$_{2-6}$alkenyl, said compounds being represented by formula (I-j), can be prepared by reacting an intermediate of formula (XI) with a Wittig or Horner-Emmons reagent of formula (XII'), wherein R$^b$— represents for example (Phenyl)₃P⁺—Cl⁻ or (CH₃CH₂—O)₂P(=O)—, which can be considered as a suitable precursor of a phosphorus ylide, in the presence of nBuLi, and a suitable solvent, such as for example tetrahydrofuran.

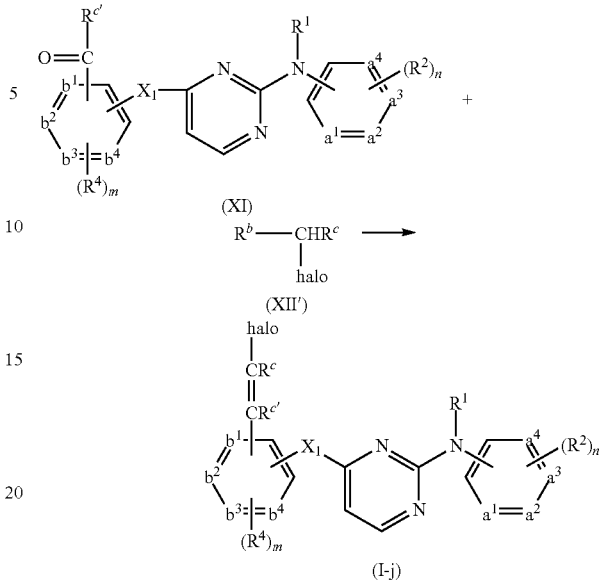

Compounds of formula (I) wherein R³ represents CR$^c$=CR$^{c''}$-halo with R$^c$ being as defined hereinabove and R$^{c'''}$ representing CN, NR⁹R¹⁰, —C(=O)—NR⁹R¹⁰, —C(=O)—C$_{1-6}$alkyl or R⁷, said compounds being represented by formula (I-k), can be prepared by reacting an intermediate of formula (XI-a) with an intermediate of formula (XIII-a) in the presence of a Horner-Emmons reagent such as for example (CH₃CH₂—O)₂P(=O)—Cl, nBuLi, 1,1,1-trimethyl-N-(trimethylsilyl)-silanamine, and a suitable solvent, such as for example tetrahydrofuran.

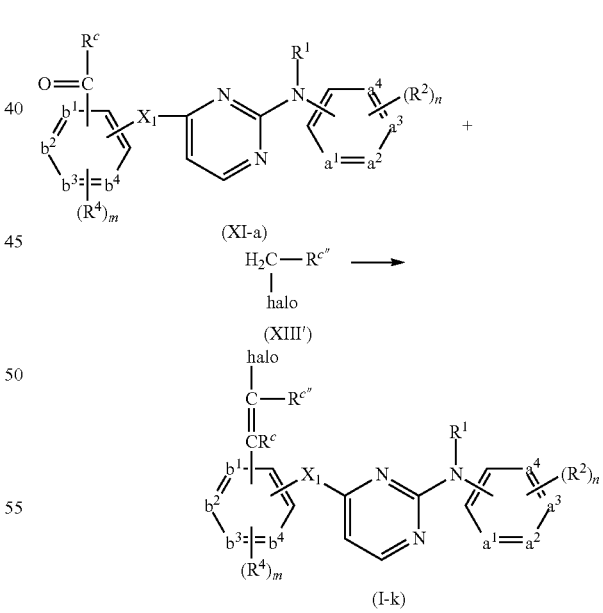

Compounds of formula (I) wherein R³ represents CH=C(Br)₂, said compounds being represented by formula (I-l), can be prepared by reacting an intermediate of formula (XVIII) with CBr₄, in the presence of a suitable catalyst salt, such as for example (CuCl)₂, and in the presence of a suitable base, such as for example NH₃, and a suitable solvent, such as for example dimethylsulfoxide.

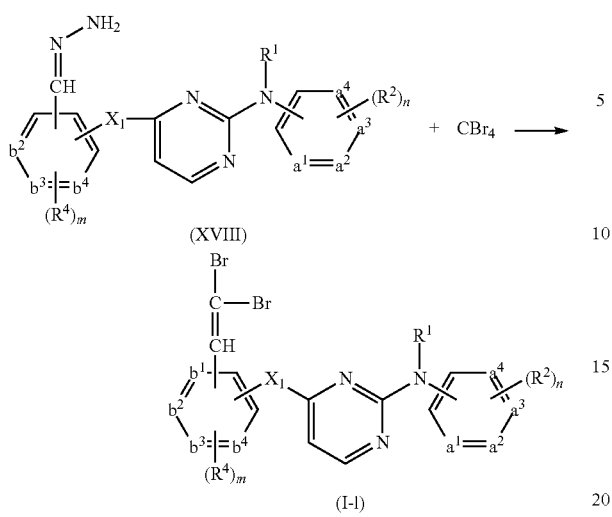

(XVIII)

(I-l)

Compounds of formula (I-m) can be prepared by reacting an intermediate of formula (XIV) with Cl$_2$C=S in the presence of a suitable solvent, such as for example dioxane.

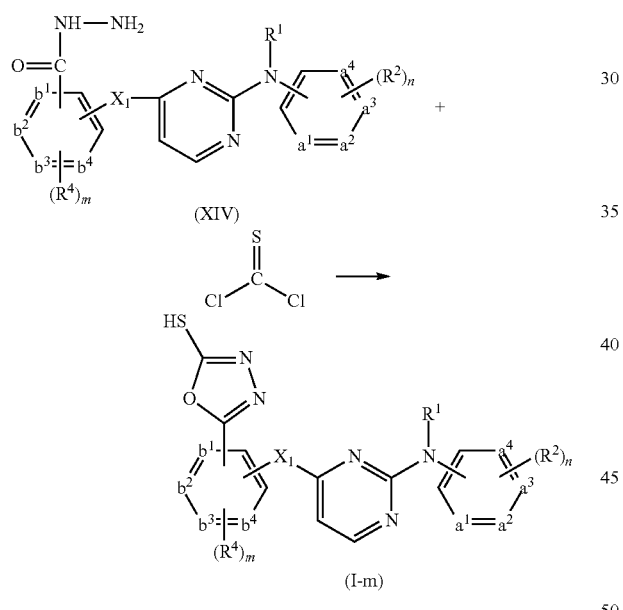

(XIV)

(I-m)

Compounds of formula (I-n) can be prepared by reacting an intermediate of formula (XV) with an intermediate of formula (XVI) in the presence of a suitable solvent, such as for example an alcohol or an alcoholate, e.g. ethanol or sodium methanolate.

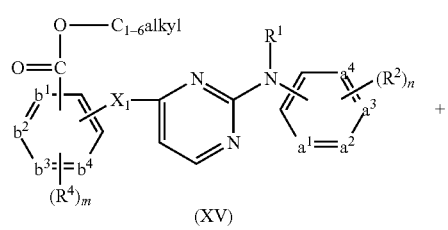

(XV)

(XVI)

(I-n)

Compounds of formula (I) wherein R$^3$ represents C$_{2-6}$alkenyl substituted with C(=O)NR$^9$R$^{10}$ and optionally further substituted with cyano, said compounds being represented by formula (I-o) wherein C$_{2-6}$alkenyl' represents C$_{2-6}$alkenyl optionally substituted with cyano, can be prepared by reacting an intermediate of formula (XXIX) with an intermediate of formula (XXX) in the presence of hydroxybenzotriazole and ethyldimethylaminopropyl carbodiimide and a suitable solvent, such as for example methylene chloride or tetrahydrofuran, and optionally in the presence of a suitable base, such as for example N,N-diethylethanamine, NH$_4$OH and the like.

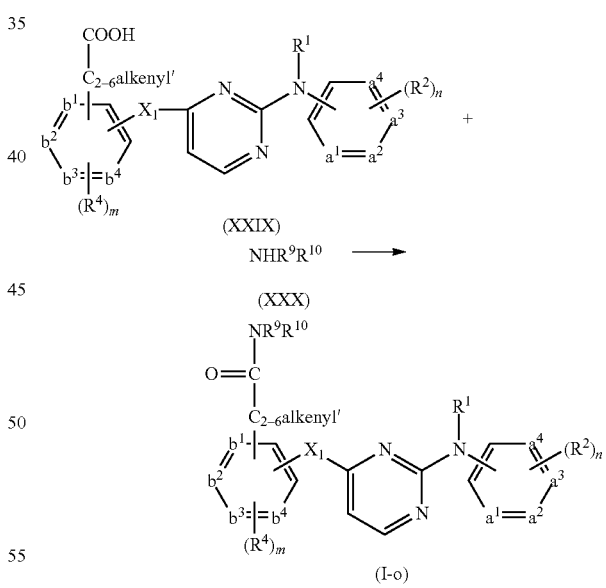

(XXIX)

NHR$^9$R$^{10}$ (XXX)

(I-o)

Compounds of formula (I) wherein R$^3$ represents —(=O)NR$^{13}$R$^{14}$ or —(=O)NHR$^{13}$, said compounds being represented by formula (I-p-1) and (I-p-2) can be prepared by reacting an intermediate of formula (XXXI) with an intermediate of formula (XXXII-1) or (XXXII-2) in the presence of hydroxybenzotriazole and ethyldimethylaminopropyl carbodiimide and a suitable solvent, such as for example methylene chloride or tetrahydrofuran, and optionally in the presence of a suitable base, such as for example N,N-diethylethanamine.

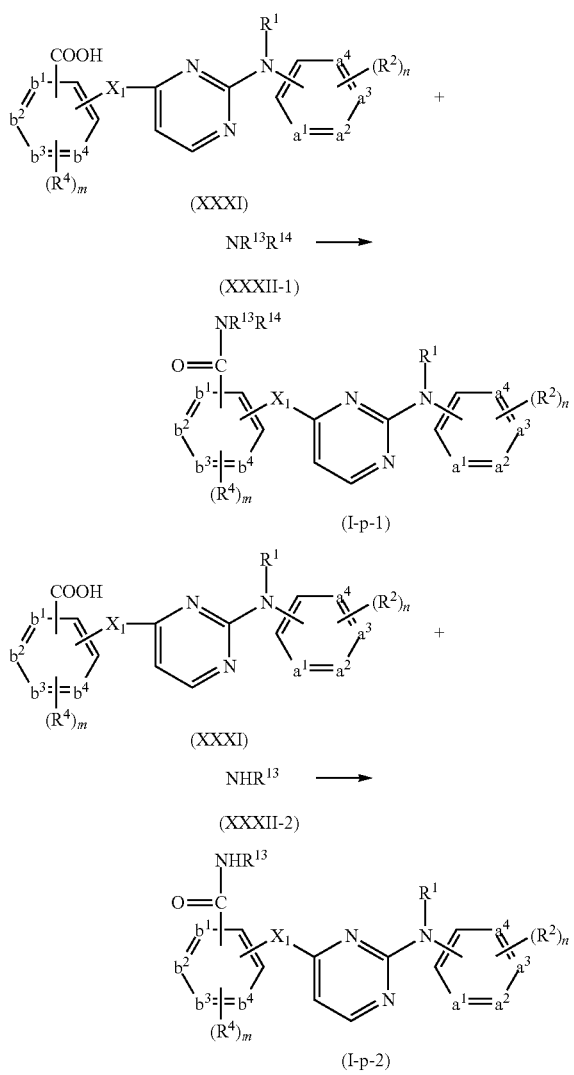

(XXXI)

NR¹³R¹⁴

(XXXII-1)

(I-p-1)

(XXXI)

NHR¹³

(XXXII-2)

(I-p-2)

Compounds of formula (I) wherein $R^3$ represents CH=N—NH—C(=O)—$R^{16}$, said compounds being represented by formula (I-q), can be prepared by reacting an intermediate of formula (XI-b) with an intermediate of formula (XXXIII) in the presence of a suitable solvent, such as for example methylene chloride and an alcohol, e.g. methanol, ethanol and the like.

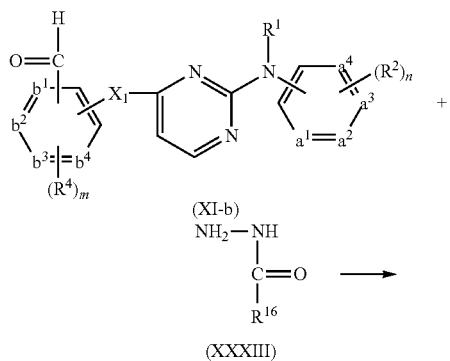

(XI-b)

(XXXIII)

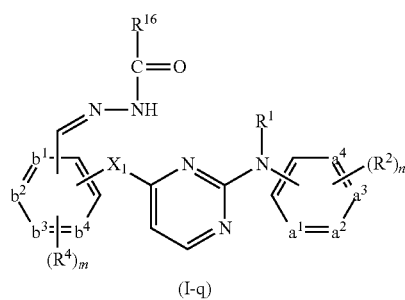

(I-q)

Compounds of formula (I) wherein $R^3$ represents $N(CH_3)_2$, said compounds being represented by formula (I-r), can be prepared by reductive methylation of an intermediate of formula (XXXIV) with formaldehyde in the presence of a suitable catalyst, such as for example a suitable acid, i.e. acetic acid and the like, palladium on charcoal, Raney Nickel, and in the presence of a suitable reductive agent, such as for example sodium cyanoborohydride or $H_2$, and a suitable solvent, such as for example acetonitrile.

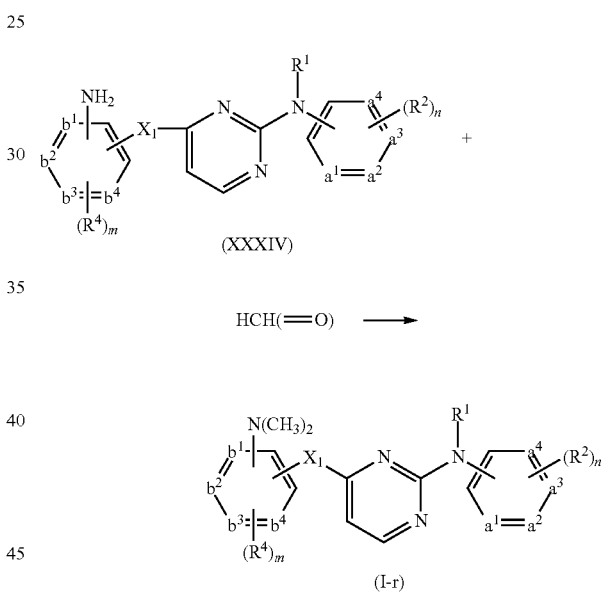

(XXXIV)

HCH(=O) →

(I-r)

Compounds of formula (I) wherein $R^3$ represents pyrrolyl, said compounds being represented by formula (I-s), can be prepared by reacting an intermediate of formula (XXXIV) with 2,5-dimethoxytetrahydrofuran in the presence of a suitable acid, such as for example acetic acid.

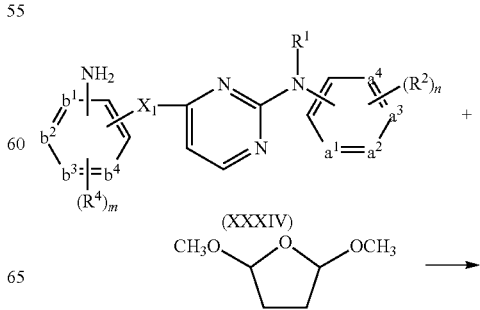

(XXXIV)

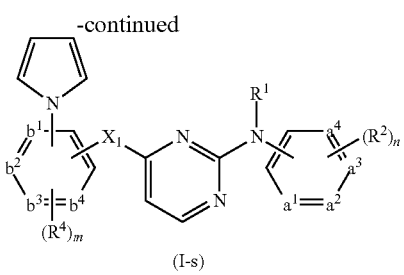

(I-s)

Compounds of formula (I) wherein R³ represents CH=CH—R⁷, said compounds being represented by formula (I-t), can be prepared by reacting an intermediate of formula (XXXV) (Ph indicates phenyl) with an intermediate of formula (XXXVI) in the presence of nBuLi and a suitable solvent, such as for example tetrahydrofuran.

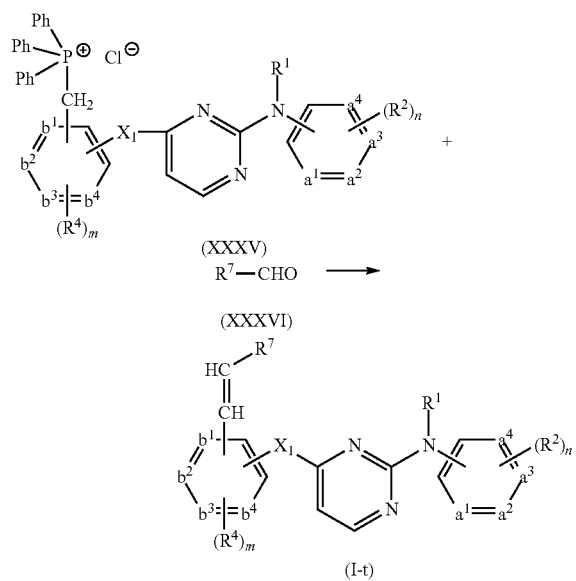

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the stating material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, a compound of formula (I) wherein R³ comprises cyano, can be converted into a compound of formula (I) wherein R³ comprises aminocarbonyl, by reaction with HCOOH, in the presence of a suitable acid, such as hydrochloric acid. A compound of formula (I) wherein R³ comprises cyano, can also further be converted into a compound of formula (I) wherein R³ comprises tetrazolyl, by reaction with sodium azide in the presence of ammonium chloride and N,N-dimethylacetamide.

Compounds of formula (I) wherein R³ comprises aminocarbonyl can be converted into a compound of formula (I) wherein R³ comprises cyano, in the presence of a suitable dehydrating agent. The dehydration can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, TsCl, $P_2O_5$, $(Ph_3PO_3SCF_3)$ $O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, ClCOCOCl, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiAe2)_4$, $LiAlH_4$ and the like. All the reagents listed in said publication are incorporated herein as reference.

Compounds of formula (I) wherein R³ comprises $C_{2-6}$alkenyl can be converted into a compound of formula (I) wherein R³ comprises $C_{1-6}$alkyl by reduction in the presence of a suitable reducing agent, such as for example $H_2$, in the presence of a suitable catalyst, such as for example palladium on charcoal, and in the presence of a suitable solvent, such as for example an alcohol, e.g. methanol.

Compounds of formula (I) wherein R³ represents CH(OH)—R¹⁶, can be converted into a compound of formula (I) wherein R³ represents C(=O)—R¹⁶ by reaction with Jones's reagent in the presence of a suitable solvent, such as for example 2-propanone.

Compound of formula (I) wherein R³ represents C(=O)—$CH_2$—R¹⁶ᵃ, wherein R¹⁶ᵃ represents cyano or aminocarbonyl, can be converted into a compound of formula (I) wherein R³ represents C(Cl)=CH—R¹⁶ᵃ by reaction with $POCl_3$.

Compounds of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with formyl can be converted into compounds of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with CH(=N—O—R⁸) by reaction with $NH_2OR^8$ in the presence of a suitable base, such as for example sodium hydroxide and a suitable solvent, such as for example an alcohol, e.g. ethanol and the like. Compounds of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with CH(=N—O—R⁸) can be converted into a compound of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with CN by reaction with a carbodiimide in the presence of a suitable solvent, such as for example tetrahydrofuran.

Compounds of formula (I) wherein R⁴ represents nitro, can be converted into a compound of formula (I) wherein R⁴ is amino, in the presence of a suitable reducing agent, such as for example H$_2$, in the presence of a suitable catalyst, such as for example Raney Nickel, and in the presence of a suitable solvent, such as for example an alcohol, e.g. methanol.

Compounds of formula (I) wherein R$^1$ is hydrogen, can be converted into a compound of formula (I) wherein R$^1$ is C$_{1-6}$alkyl, by reaction with a suitable alkylating agent, such as for example iodo-C$_{1-6}$alkyl, in the presence of a suitable base, such as for example sodium hydride, and a suitable solvent, such as for example tetrahydrofuran.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures or some of the compounds of formula (I) or the described intermediates may be prepared according to the procedures described in WO 99/50250 and WO 00/27825.

Intermediates of formula (II) can be prepared by reacting an intermediate of formula (XVII) with a leaving group introducing agent of formula (XIX) wherein W$_1$ represents the leaving group and R represents the remaining of the leaving group introducing agent, such as for example POCl$_3$.

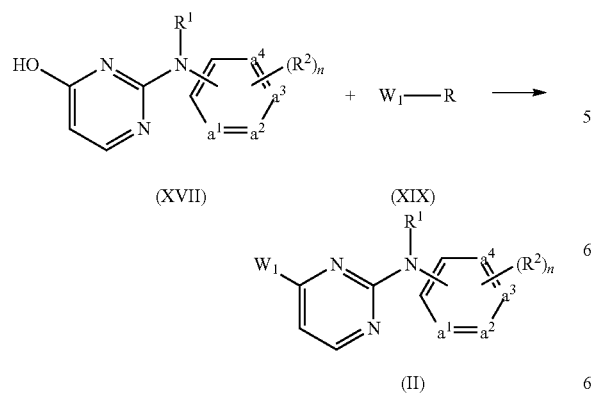

Intermediates of formula (III) wherein X$_1$ represents NH, said intermediates being represented by formula (III-a), can be prepared from an intermediate of formula (XX) in the presence of ZnCl$_2$ and in the presence of a suitable solvent, such as for example an alcohol, for example ethanol.

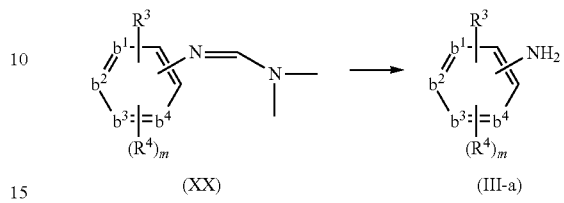

Intermediates of formula (III'-a) as depicted below can be prepared from an intermediate of formula (XX) wherein R$^3$ represents C$_{2-6}$alkenyl substituted with CN, said intermediate being represented by formula (XX-a), in the presence of ZnCl$_2$ and in the presence of a suitable C$_{1-4}$alkyl-OH, such as for example ethanol.

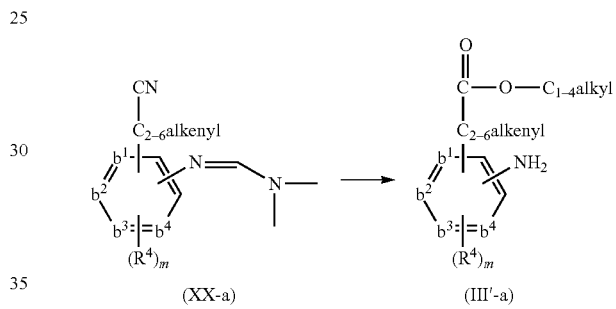

Intermediates of formula (III-b-1) and (III-b-2) as depicted below can be prepared by reacting an intermediate of formula (XII) or an appropriate acid addition salt thereof, wherein W$_6$ represents a suitable leaving group, with acrylonitrile or acrylamide in the presence of a suitable palladium catalyst, a suitable base and a suitable solvent.

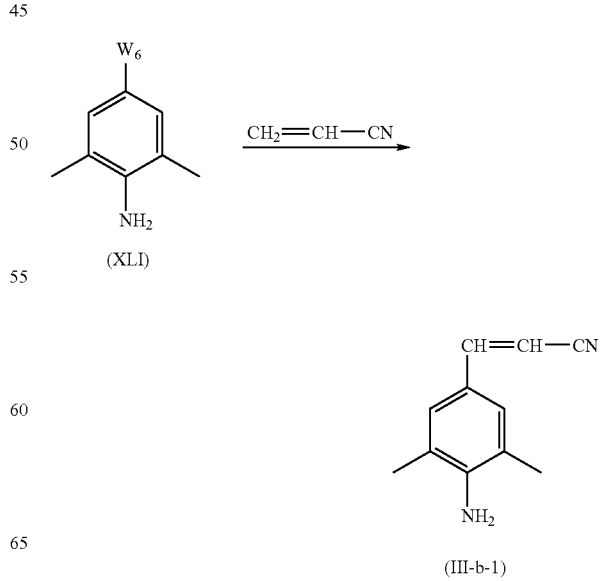

-continued

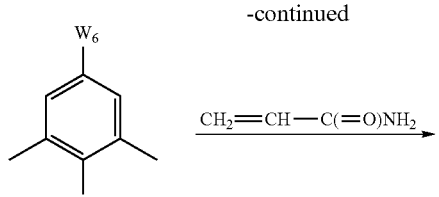

(XLI)

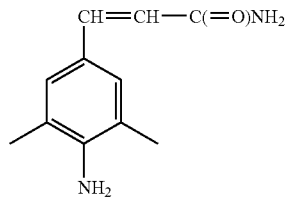

(III-b-2)

Suitable leaving groups in the above reaction are for example halo, triflate, tosylate, mesylate and the like. Preferably, $W_6$ is halo, more preferably iodo or bromo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, bis(dibenzylidene acetone) palladium, palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases in the above reaction are for example sodium acetate, potassium acetate, N,N-diethylethanamine, sodium hydrogencarbonate, sodium hydroxide and the like.

Suitable solvents in the above reaction are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

Intermediates of formula (III-b-2) can be converted into an intermediate of formula (III-b-1) in the presence of a suitable dehydrating agent. The dehydration can be performed according to methodologies well-known to the person skilled in the art, such as the ones disclosed in "Comprehensive Organic Transformations. A guide to functional group preparations" by Richard C. Larock, John Wiley & Sons, Inc, 1999, p. 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, TsCl, $P_2O_5$, $(Ph_3PO_3SCF_3)O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, $ClCOCOCl$, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiMe_2)_4$, $LiAlH_4$ and the like. All the reagents listed in said publication are incorporated herein as reference.

Intermediates of formula (XX) wherein $R^3$ represents $CR^{c'}=CR^c$—CN with $R^c$ and $R^{c'}$ as described hereinabove, said intermediates being represented by formula (XX-b), can be prepared from an intermediate of formula (XXI) by the reaction described above for the preparation of a compound of formula (I-f).

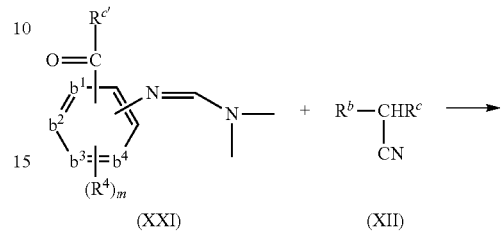

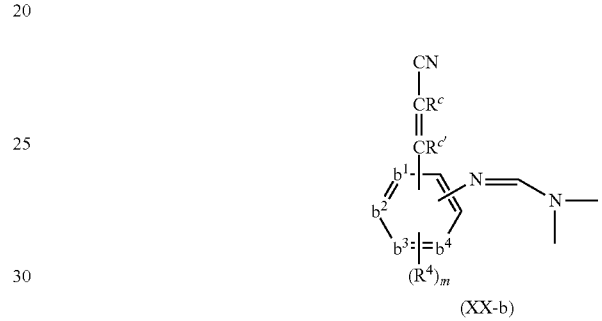

(XX-b)

Intermediates of formula (XXI) can be prepared by oxidation of an intermediate of formula (XXII) in the presence of a suitable oxidizing agent, such as for example $KMnO_4$, in the presence of a suitable solvent, such as for example methylene chloride and tris[2-(2-methoxyethoxy)ethyl]amine.

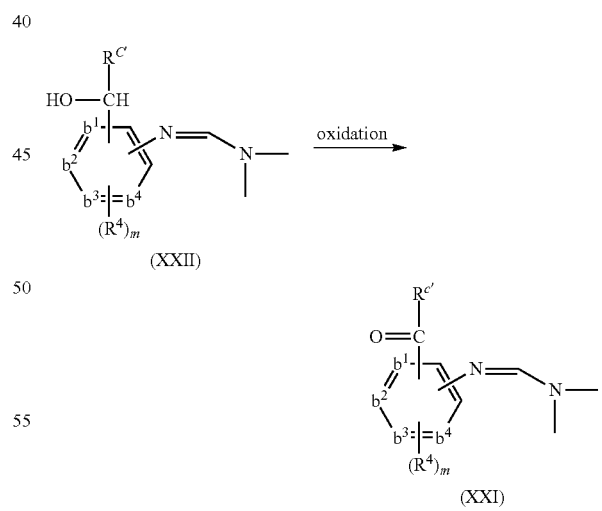

Intermediates of formula (XXI) wherein $R^{c'}$ is H, said intermediates being represented by formula (XXI-a), can also be prepared by reacting an intermediate of formula (XXIII) wherein $W_4$ represents a suitable leaving group, such as halo, e.g. bromo, with N,N-dimethylformamide in the presence of nBuLi and in the presence of a suitable solvent, such as for example tetrahydrofuran.

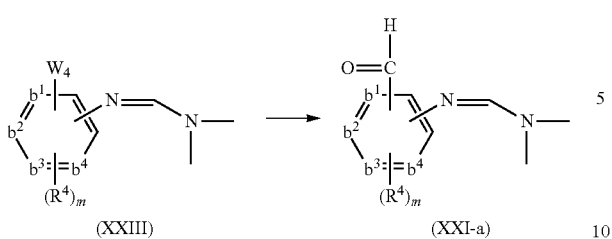

Intermediates of formula (XXI) wherein $R^{c'}$ represents $C_{1-4}$alkyl, said intermediates being represented by formula (XXII-a), can be prepared by reacting an intermediate of formula (XXIII) with an intermediate of formula (XXIV) in the presence of nBuLi and in the presence of a suitable solvent, such as for example tetrahydrofuran.

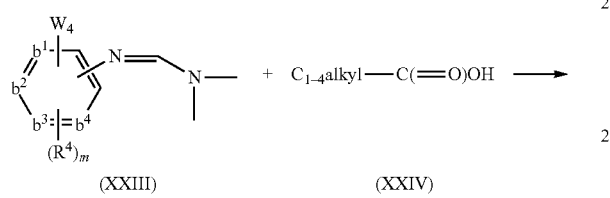

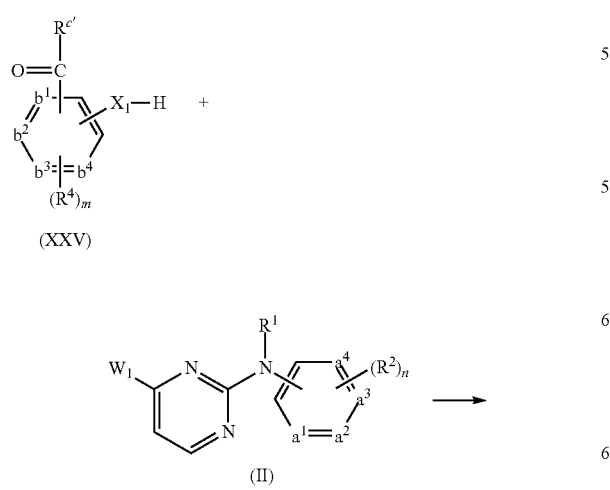

Intermediates of formula (XI) can be prepared by reacting an intermediate of formula (XXV) with an intermediate of formula (II), optionally in the presence of a suitable base, such as for example 1-methyl-pyrrolidin-2-one, or a suitable acid, such as for example hydrochloric acid.

Intermediates of formula (XV) can be prepared by reacting an intermediate of formula (XXVI) with an intermediate of formula (II) in the presence of a suitable base, such as for example 1-methyl-pyrrolidin-2-one and sodium hydride and a suitable solvent, such as for example dioxane.

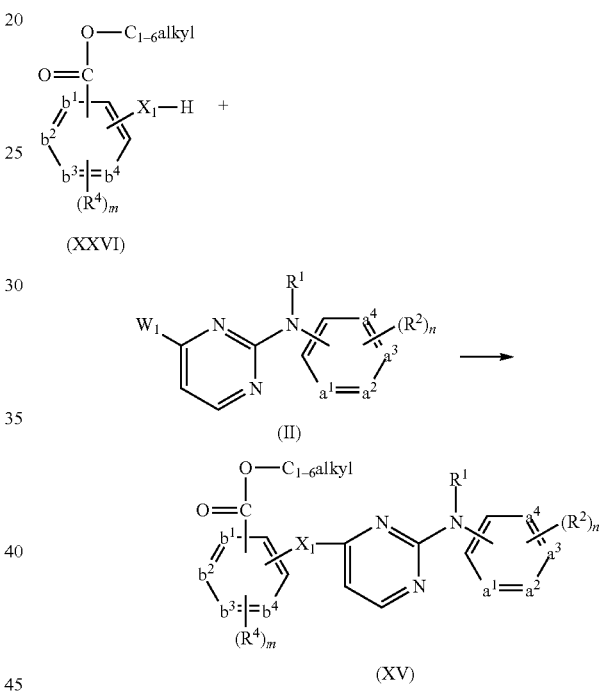

Intermediates of formula (VII) can be prepared by reacting an intermediate of formula (XXVII) with a leaving group introducing agent of formula (XIX'), such as for example $SOCl_2$, in the presence of a suitable solvent, such as for example methylene chloride.

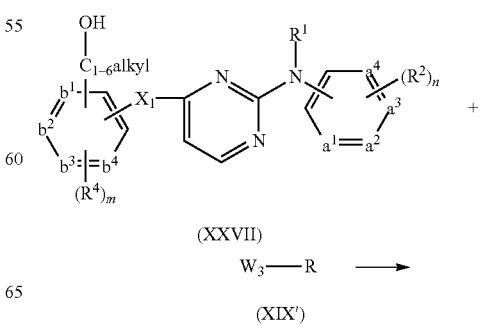

-continued

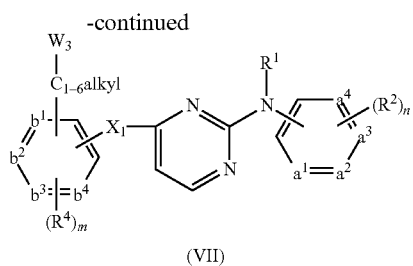

(VII)

Intermediates of formula (XXVII) wherein $C_{1-6}$alkyl represents $CH_2$, said intermediates being represented by formula (XXVII-a), can be prepared by reducing an intermediate of formula (XV) or formula (XXXI) with a suitable reducing agent, such as for example $LiAlH_4$, in the presence of a suitable solvent, such as for example tetrahydrofuran.

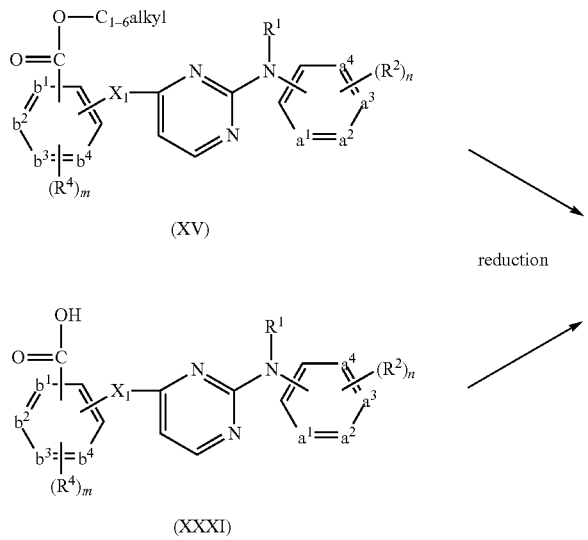

Intermediates of formula (XXVII-a) can be converted to an intermediate of formula (XXXI) by reaction with Jones reagent in the presence of a suitable solvent, such as for example acetone.

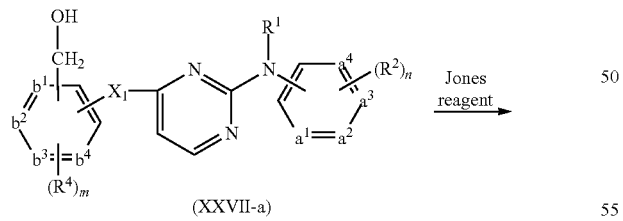

Intermediates of formula (XI-b) can be prepared by oxidizing an intermediate of formula (XXVII-a) in the presence of a suitable oxidizing agent, such as for example $MnO_2$, and a suitable solvent, such as for example methylene chloride, N,N-dimethylformamide.

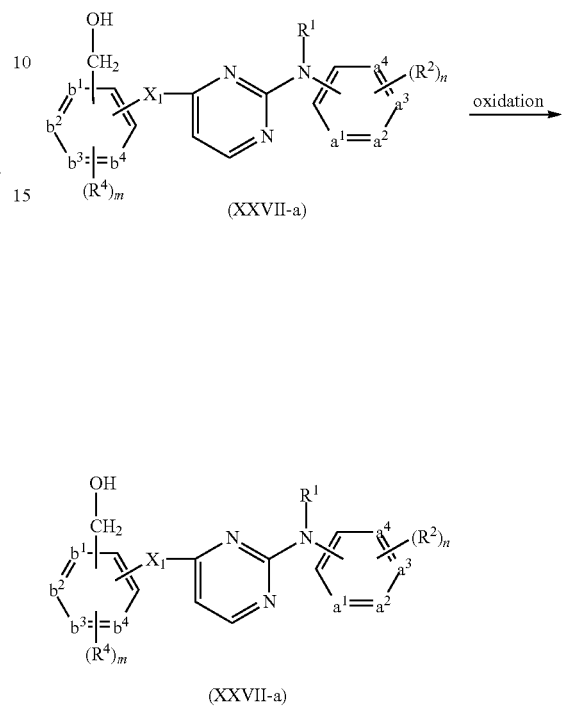

-continued

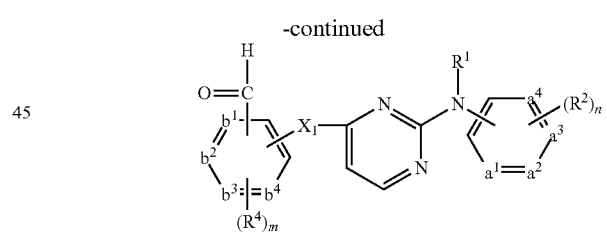

Intermediates of formula (XIV) can be prepared by reacting an intermediate of formula (XV) with $H_2N$—$NH_2$ in the presence of a suitable solvent, such as for example an alcohol, e.g. ethanol and the like.

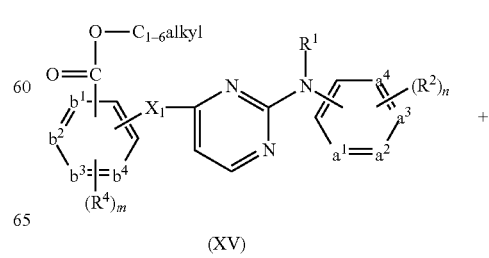

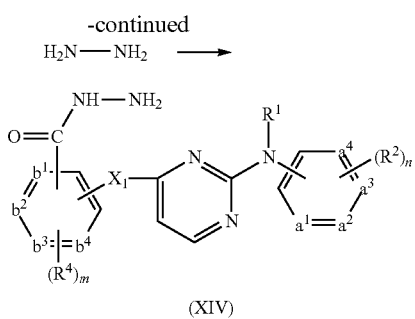

(XIV)

Intermediates of formula (I) and (XI-a) can be reduced to an intermediate of formula (XXVII'-a) and (XXVII'-b) in the presence of a suitable reducing agent, such as for example NaBH$_4$, LiAlH$_4$ or BuLi and a suitable solvent, such as for example tetrahydrofuran or an alcohol, e.g. methanol, ethanol and the like.

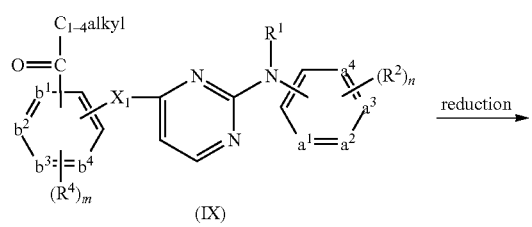

(IX)

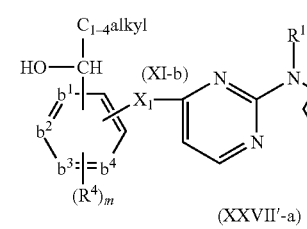

(XXVII'-a)

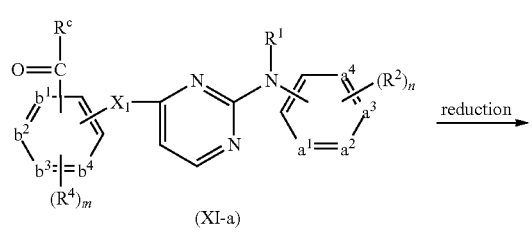

(XI-a)

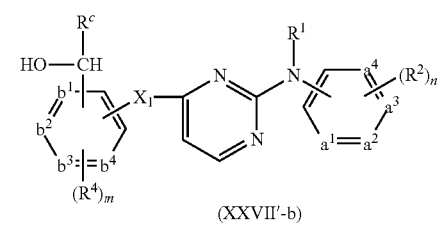

(XXVII'-b)

An intermediate of formula (XI-b) can be converted into an intermediate of formula (XXVII'-a) by reaction with C$_{1-4}$alkyl-Iodide in the presence of Mg and a suitable solvent, such as for example diethylether and tetrahydrofuran.

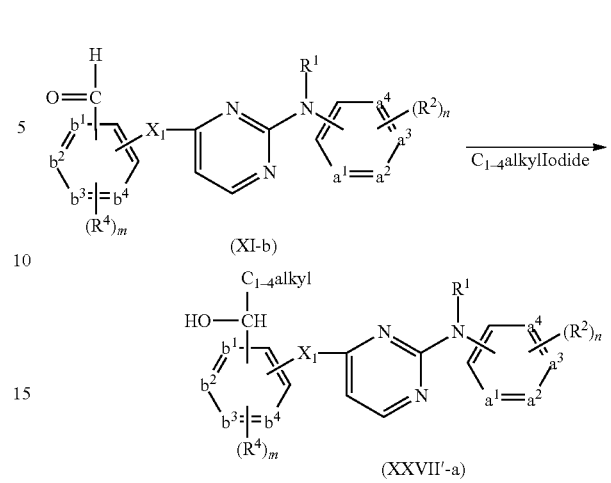

(XI-b)

(XXVII'-a)

Intermediates of formula (XVIII) can be prepared by reacting an intermediate of formula (XI-b) with H$_2$N—NH$_2$ in the presence of a suitable solvent, such as for example an alcohol, e.g. ethanol and the like.

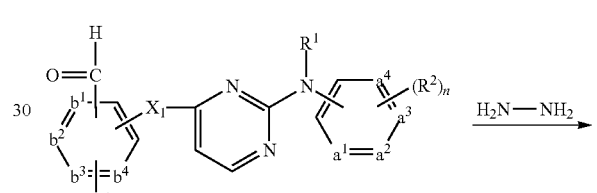

(XI-b)

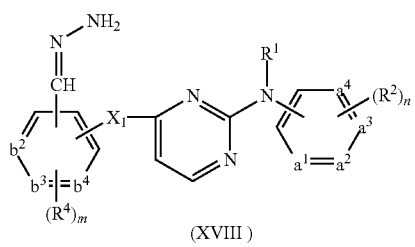

(XVIII)

Intermediates of formula (XXIX) or (XXXI) can be prepared by hydrolizing an intermediate of formula (XXXVII) wherein C$_{2-6}$alkenyl' represents C$_{2-6}$alkenyl optionally substituted cyano, or an intermediate of formula (XV) in the presence of a suitable aqueous acid solution, such as for example hydrochloric acid 2N and the like, and in the presence of a suitable solvent, such as for example an alcohol, e.g. isopropanol and the like.

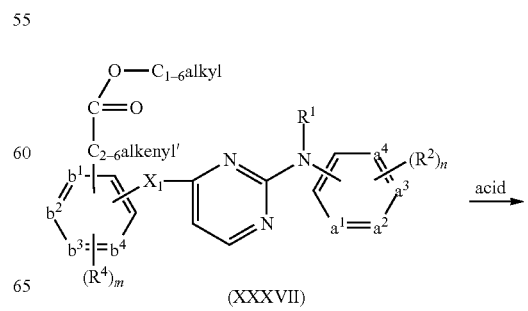

(XXXVII)

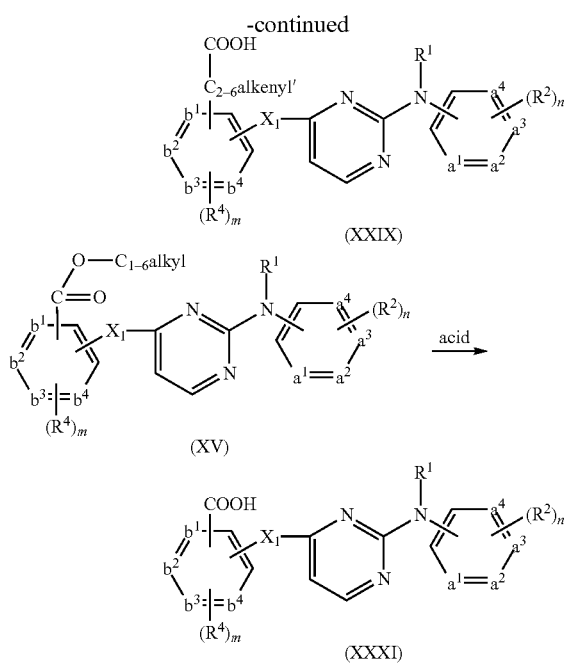

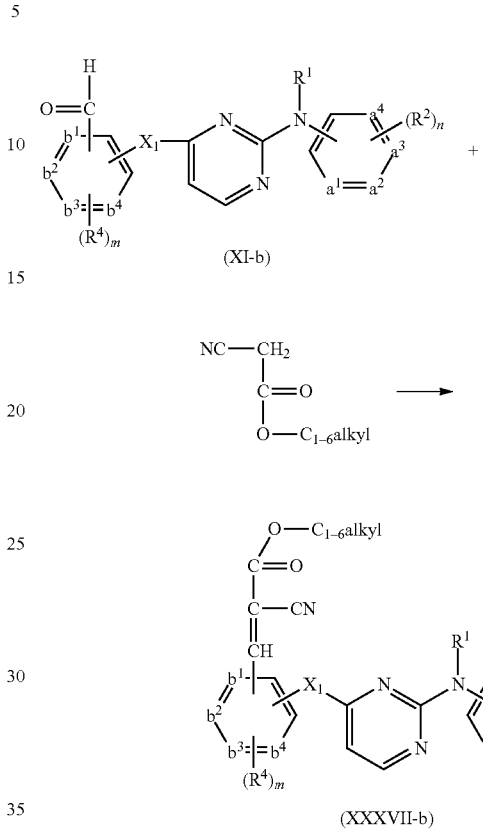

Intermediates of formula (XXXVII) wherein $C_{2-6}$alkenyl is CH=CH, said intermediates being represented by formula (XXXVII-a), can be prepared by reacting an intermediate of formula (XI-b) with a Wittig or Horner-Emmons reagent of formula (XII″), wherein $R^b$ represents for example $(Phenyl)_3{}^+$—$Cl^-$ or $(^{CH_3}CH_2$—$O)_2P(=O)$—, which can be considered as a suitable precursor of a phosphorus ylide, in the presence of a suitable solvent, such as for example tetrahydrofuran.

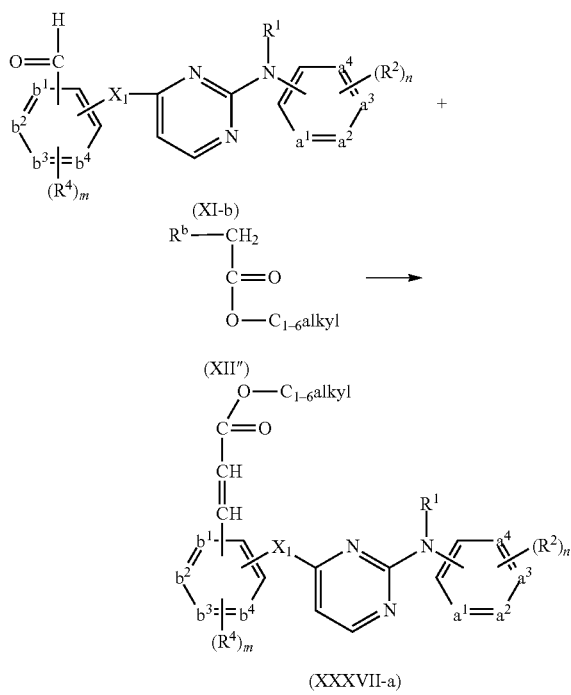

Intermediates of formula (XXXVII) wherein $C_{2-6}$alkenyl' is —CH=C(CN)—, said intermediates being represented by formula (XXXVII-b), can be prepared by reacting an intermediate of formula (XI-b) with NC—$CH_2$—C(=O)O—$C_{1-6}$alkyl, in the presence of a suitable base, such as for example piperidine, and a suitable solvent, such as for example an alcohol, e.g. ethanol.

Intermediates of formula (XXXIV) can be prepared by reducing an intermediate of formula (XXXVIII) in the presence $H_2$ and a suitable catalyst, such as for example palladium on charcoal or Raney Nickel, and in the presence of a suitable solvent, such as for example an alcohol, e.g. methanol and the like.

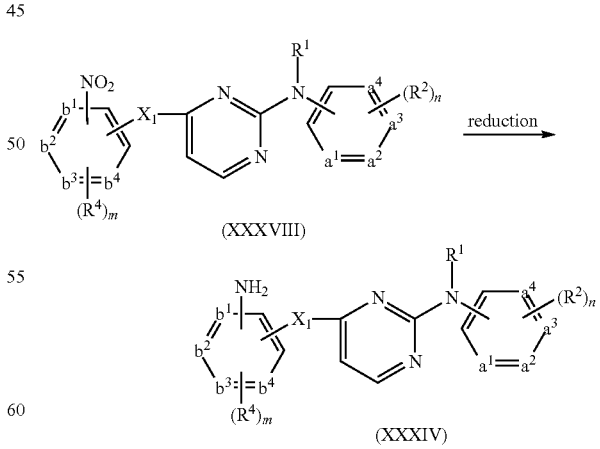

Intermediates of formula (XXXV) can be prepared by reacting an intermediate of formula (XII-a) in the presence of triphenylphosphine and a suitable catalyst, such as for example acetonitrile.

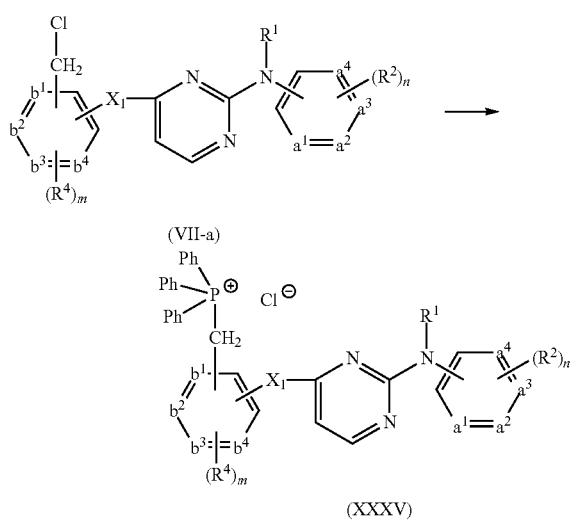

(VII-a)

(XXXV)

Intermediates of formula (XXXIX) can be prepared by reacting an intermediate of formula (XL) with an intermediate of formula (II-a) wherein $W_5$ $W_1$ are as defined hereinbefore.

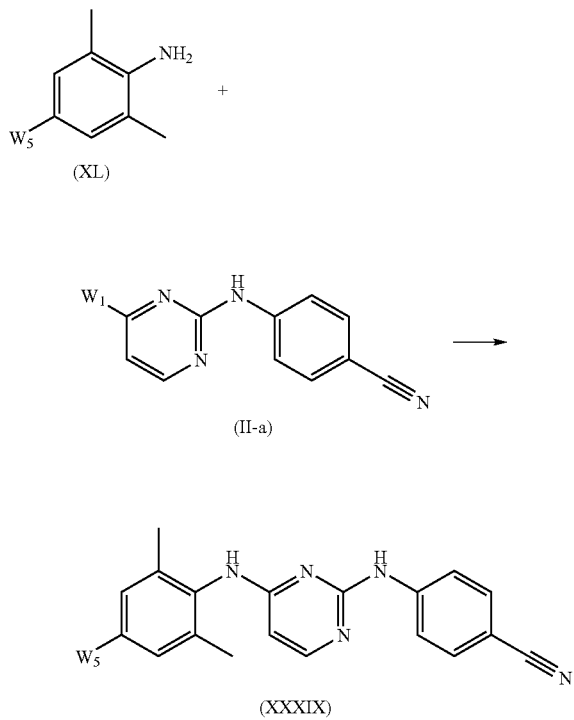

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$-alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The compounds of formula (I) or any subgroup thereof show antiretroviral properties (reverse transcriptase inhibiting properties), in particular against Human Immunodeficiency Virus (HIV), which is the aetiological agent of Acquired Immune Deficiency Syndrome (AIDS) in humans.

The compounds of formula (I) or any subgroup thereof also show activity against (multi) drug resistant HIV strains, in particular (multi) drug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The following examples are intended to illustrate the compounds of formula (I).

Hereinafter, "DMF" is defined as N,N-dimethylformamide, "DIPE" is defined as diisopropyl ether, "THF" is defined as tetrahydrofurane, "DMA" is defined as N,N-dimethylacetamide, "DMSO" is defined as dimethylsulfoxide, "DME" is defined as dimethyl ether, "EtOAc" is defined as ethylacetate, "EDCI" is defined as N'-(ethylcarbonimidoyl)-N,N-dimethyl-1,3-propanediamine.

A. Preparation of the Intermediate Compounds

Example A1 a) The Preparation of Intermediate 1

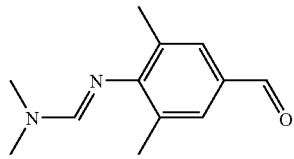

nBuLi (0.012 mol) was added dropwise at −70° C. to a mixture of N'-(4-bromo-2,6-dimethylphenyl)-N,N-dimethylmethanimidamide (0.0078 mol) in THF (20 ml) under $N_2$ flow. The mixture was stirred at −30° C. for 30 minutes, then cooled to −70° C. A mixture of DMF (0.078 mol) in THF (30 ml) was added dropwise. The mixture was stirred at −70° C. for 2 hours, then brought to 0° C., poured out into $H_2O$ and extracted with ethyl acetate. The organic layer was separated, dried ($MgSO_4$), filtered and the solvent was evaporated. Yield: 1.8 g of intermediate 1.

b) The Preparation of Intermediate 2

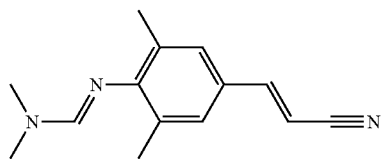 [SMILES: Cc1cc(/C=C/C#N)cc(C)c1/N=C/N(C)C]

A mixture of diethyl(cyanomethyl)phosphonate (0.0037 mol) in THF (10 ml) was cooled to 5° C. under $N_2$ flow. Potassium tert.-butoxide (0.0037 mol) was added portionwise. The mixture was stirred at 5° C. for 30 minutes, then stirred at room temperature for 30 minutes. A mixture of intermediate 1 (0.0024 mol) in THF (10 ml) was added. The mixture was stirred at room temperature for 1 hour, then poured out into $H_2O$ and extracted with $CH_2Cl_2$. The organic layer was separated, dried ($MgSO_4$), filtered and the solvent was evaporated. Yield: 0.82 g (100%) of intermediate 2.

c) The preparation of intermediate 3 and Intermediate 22

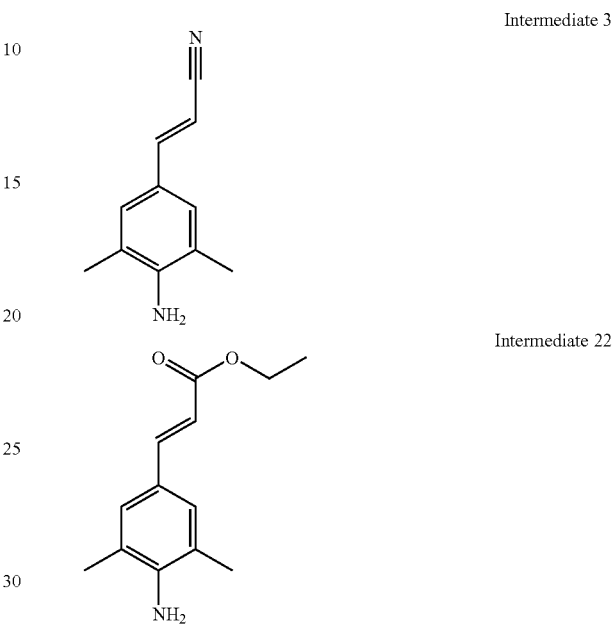

A mixture of intermediate 2 (0.059 mol) and $ZnCl_2$ (0.299 mol) in ethanol (150 ml) was stirred and refluxed for 24 hours, then poured out into $K_2CO_3$ solution (10% in water) and extracted with $CH_2Cl_2$. The organic layer was separated, dried ($MgSO_4$), filtered and the solvent was evaporated. The residue (9 g) was crystallized from DIPE. The precipitate was filtered off and dried. Yield: 0.8 g (6%) of intermediate 22. The filtrate was concentrated and recrystallized from DIPE to obtain 6 g of intermediate 3.

Alternatively, intermediate 3 was also prepared as follows:
To a solution of 159 g of 4-iodo-2,6-dimethyl-benzenamine was added 63.8 g of sodium acetate. The reaction mixture was kept under nitrogen atmosphere. 7 g of moistered palladium on charcoal (Pd/C 10%) and 64.4 ml of acrylonitrile was added. The reaction mixture was heated to 130° C. and stirred overnight. After cooling to room temperature, 0.5 l of toluene and 0.5 l of N,N-dimethylacetamide was added. The reaction mixture was filtered over Dicalite and the filter was washed with 0.5 l of toluene. Water (6 l) was added to the mixture which was stirred for 30 minutes. The layers were separated. To the aqueous layer, 1 l of toluene was added and the mixture was stirred for 30 minutes. The layers were separated again. The separated organic layers were collected and the solvent was evaporated, yielding 123 g of intermediate 3.

Intermediate 3 was converted into its hydrochloric acid salt as follows:
To a mixture of 123 g of intermediate 3 in 630 ml of ethanol was added 1,25 l of diisopropyl ether. The reaction mixture was kept under nitrogen atmosphere. The mixture was heated to 60° C. and stirred for 30 minutes. 120 ml of a 6 N solution of hydrochloric acid in 2-propanol was added and the mixture was stirred for 30 minutes. After cooling to room temperature, the reaction mixture was filtered and the residue was washed with 100 ml of 2-propanol. The resulting residue was dried under reduced pressure at 50° C. Yield: 103 g (77%) of the hydrochloric acid salt (1:1) of intermediate 3.

Intermediate 3 (E) was prepared as follows:

x) Preparation of Intermediate 3a (E)

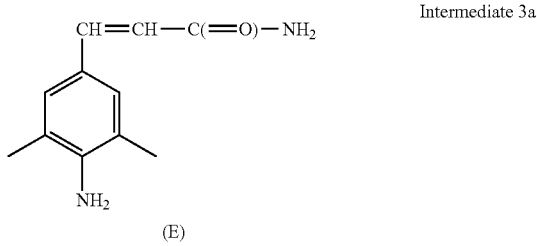

Intermediate 3a (E)

In 10 ml acetonitrile, dry, was dissolved 2.00 g (10.0 mol) of 4-bromo-2,6-dimethylaniline, 1.07 g (1.5 eq) of acrylamide, 224 mg (0.1 eq) of Pd(OAc)$_2$, 609 mg (0.2 eq) of tris(2-methylphenyl)phosphine and 1.52 g of N,N-diethylethanamine. The mixture was purged with N$_2$ for 20 minutes and stirred overnight at 70° C. The mixture was diluted with 150 ml of methylene chloride, washed with saturated aqueous NaHCO$_3$ solution, dried (sat. NaCl, Na$_2$SO$_4$) and filtered. The solvent was evaporated 10 and the residue was stirred in diisopropyl ether followed by filtration. Yield: 1.51 g (79.5%) of intermediate 3a (E).

y) Preparation of Intermediate 3 (E)

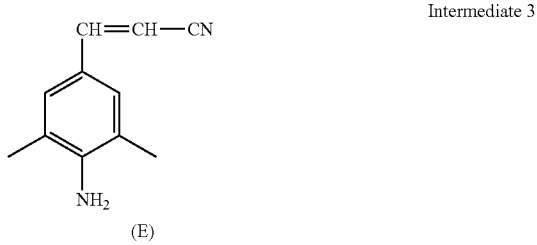

Intermediate 3

(E)

POCl$_3$ (3 ml) was cooled to 0° C. and 500 mg (2.63 mmol) of intermediate 3a (E) was added. After 30 minutes, the cooling bath was removed and the mixture was stirred overnight at 20° C. The mixture was added dropwise to 150 ml of diisopropyl ether while stirring vigorously. The precipitate was filtered and washed with diisopropyl ether. The residue was added to 100 ml ethyl acetate/100 ml of saturated aqueous NaHCO$_3$ solution and stirred. The ethyl acetate layer was separated, dried (sat. NaCl, Na$_2$SO$_4$) and filtered. The solvent was evaporated. Yield: 380 mg (84%) of intermediate 3 (E).

d) The Preparation of Intermediate 4

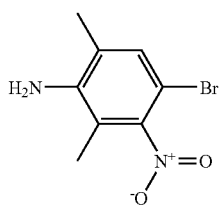

A mixture of 4-bromo-2,6-dimethylbenzenamine (0.024 mol) in H$_2$SO$_4$ (30 ml) was stirred at −5° C. KNO$_3$ (0.024 mol) was added slowly. The mixture was stirred at −5° C. for 30 minutes, poured out into H$_2$O and extracted with ethyl acetate. The organic layer was washed with H$_2$O, separated, dried (MgSO$_4$), filtered and the solvent was evaporated. The residue (0.058 g, 95%) was purified by column chromatography over silica gel (eluent: cyclohexane/ethyl acetate; 70/30; 15-40 μm). The pure fractions were collected and the solvent was evaporated. Yield: 4.1 g of intermediate 4.

Example A1A

The preparation of intermediate 28

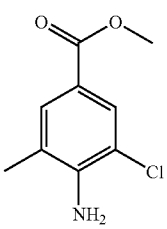

1-chloro-pyrrolidine-2,5-dione (0.032 mol) was added at 60° C. to a mixture of 4-amino-3-methyl-benzoic acid ethyl ester [CAS 40800-65-5] (0.029 mol) in CH$_3$CN (50 ml). The mixture was stirred and refluxed slowly. K$_2$CO$_3$ 10% was added. The mixture was extracted with CH$_2$Cl$_2$. The organic layer was evaporated. The residue (6.6 g) was purified by column chromatography over silica gel (eluent: cyclohexane/EtOAc 85/15; 15-40 μm). The pure fractions were collected and the solvent was evaporated. Yield: 5.2 g of intermediate 28 (84%).

Example A2

A mixture of 4-[(1,4-dihydro-4-oxo-2-pyrimidinyl)amino]benzonitrile (0.12 mol) in POCl$_3$ (90 ml) was stirred and refluxed under Argon for 20 minutes. The reaction mixture was slowly poured onto 750 ml ice/water, and the solid was separated by filtration. The solid was suspended in 500 ml water, and the pH of the suspension was adjusted to neutral by adding a 20% NaOH solution. The solid was again separated by filtration, suspended in 200 ml 2-propanone, and 1000 ml CH$_2$Cl$_2$ was added. The mixture was heated until all solid had dissolved. After cooling to room temperature, the aqueous layer was separated, and the organic layer was dried. During removal of the drying agent by filtration, a white solid formed in the filtrate. Further cooling of the filtrate in the freezer, followed by filtration, yielded 21.38 g (77.2%) of [4-[(4-chloro-2-pyrimidinyl)amino]benzonitrile (interm. 5).

Example A3 a) The Preparation of Intermediate 6

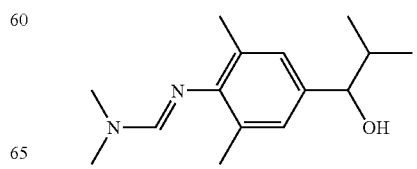

nBuLi (0.024 mol) was added dropwise at −70° C. to a mixture of N'-(4-bromo-2,6-dimethylphenyl)-N,N-dimethylmethanimidamide (0.0157 mol) in THF (50 ml) under $N_2$ flow. The mixture was stirred at −30° C. for 30 minutes, then cooled to −70° C. A solution of 2-methylpropanal (0.055 mol) in THF (50 ml) was added. The mixture was stirred at −70° C. for 2 hours, then brought to 0° C., poured out into $H_2O$ and extracted with $CH_2Cl_2$. The organic layer was separated, dried ($MgSO_4$), filtered and the solvent was evaporated. The residue (6.7 g) was purified by column chromatography over silica gel (eluent: $CH_2Cl_2/CH_3OH/NH_4OH$ 95/5l0.5; 15-40 μm). Two fractions were collected and the solvent was evaporated. Fraction 1: yield: 1.5 g of intermediate 6 (38%).

b) The Preparation of Intermediate 7

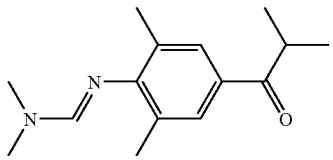 [SMILES: Cc1cc(C(=O)C(C)C)cc(C)c1/N=C/N(C)C]

Tris[2-(2-methoxyethoxy)ethyl]amine (0.0193 mol) was added at room temperature to a solution of intermediate 6 (0.0048 mol) in $CH_2Cl_2$ (20 ml). $KMnO_4$ (0.0193 mol) was added portionwise. The mixture was stirred at room temperature overnight, then filtered over celite and washed with $CH_2Cl_2$. The organic layer was washed with $K_2CO_3$ 10%, separated, dried ($MgSO_4$), filtered and the solvent was evaporated. Yield: 1.2 g (100%) of intermediate 7.

c) The Preparation of Intermediate 8

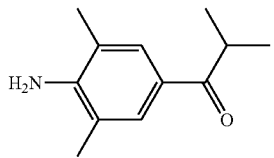

A mixture of intermediate 7 (0.0043 mol) and $ZnCl_2$ (0.017 mol) in ethanol (20 ml) was stirred and refluxed overnight, poured out into $H_2O$ and extracted with $CH_2Cl_2/CH_3OH$. The organic layer was separated, dried ($MgSO_4$), filtered and the solvent was evaporated. Yield: 0.94 g (82%) of intermediate 8.

d-1) The preparation of intermediate 9

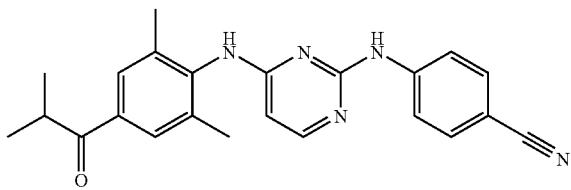 [SMILES: Cc1cc(C(=O)C(C)C)cc(C)c1Nc1ccnc(Nc2ccc(C#N)cc2)n1]

A mixture of intermediate 8 (0.0049 mol) and intermediate 5 (0.0025 mol) was stirred at 150° C. for 2 hours and taken up in $K_2CO_3$ 10%/$CH_2Cl_2$/$CH_3OH$. The organic layer was separated, dried ($MgSO_4$) and the solvent was evaporated. The residue (1.3 g) was crystallized from DIPE. The precipitate was filtered off and dried. The mother layer was purified by column chromatography over silica gel (eluent: $CH_2Cl_2/CH_3OH$ 98.5/1.5; 15-40 μm). The pure fractions were collected and the solvent was evaporated. Yield: 0.21 g of intermediate 9.

d-2) The preparation of intermediate 29

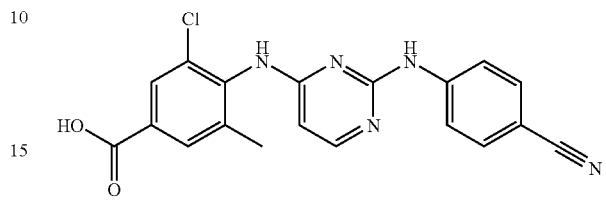

A mixture of intermediate 28 (0.023 mol) and intermediate 5 (prepared according to A2) (0.025 mol) in HCl 3N (10 ml) was stirred at 105° C. then brought to room temperature and filtered. The precipitate was washed with DIPE and dried. Yield: 8.4 g of intermediate 29 (96%)

d-3) The preparation of intermediate 30

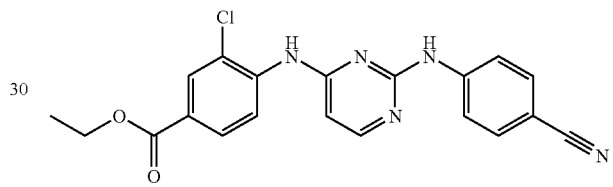

A mixture of 4-amino-3-chloro benzoic acid ethyl ester [CAS 82765-44-4] (0.02 mol) and intermediate 5 (prepared according to A2) (0.0243 mol) in 1-methyl-pyrrolidin-2-one (40 ml) was stirred at 180° C. for 2 hours, then poured out into $H_2O$ and extracted three times with EtOac (80 ml). The organic layer was separated, dried ($MgSO_4$), filtered and the solvent was evaporated. The residue (10 g) was purified by column chromatography over silica gel (eluent: $CH_2Cl_2$ 100; 15-30 μm). Two fractions were collected and the solvent was evaporated. Yield: 1.7 g F1 and 1 g F2. F2 was taken up in diethyl ether. The precipitate was filtered off and dried. Yield: 0.95 g of intermediate 30 (12%).

e-1) The preparation of intermediate 17

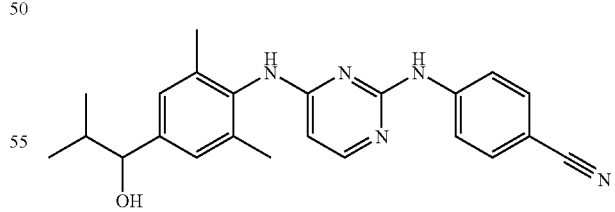

$NaBH_4$ (0.0001 mol) was added portionwise at 5° C. to a mixture of intermediate 9 (0.0001 mol) in ethanol (7 ml) under $N_2$ flow. The mixture was stirred at 5° C. for 1 hour, poured out on ice and extracted with $CH_2Cl_2$. The organic layer was separated, dried ($MgSO_4$), filtered, and the solvent was evaporated. The residue (0.1 g) was crystallized from DIPE. The precipitate was filtered off and dried. Yield: 0.044 g of intermediate 17.

e-2) The preparation of intermediate 32

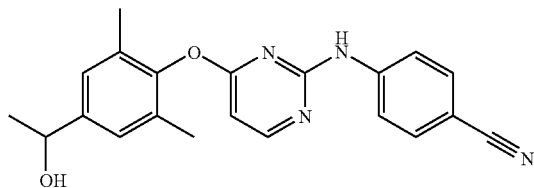 [SMILES: Cc1cc(C(C)O)cc(C)c1Oc1ccnc(Nc2ccc(C#N)cc2)n1]

BuLi 1.6 M (0.009 mol) was added at −78° C. to a mixture of (intermediate 31)

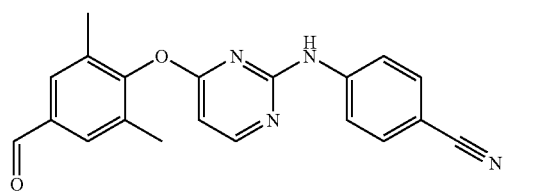

(prepared according to A4a) (0.0029 mol) in THF (25 ml) under $N_2$ flow. The mixture was stirred at −78° C. for 10 minutes, then brought to room temperature and stirred for 3 hours. $H_2O$ was added. The mixture was extracted with $CH_2Cl_2$. The organic layer was separated, dried ($MgSO_4$), filtered, and the solvent was evaporated. The residue (1.28 g) was purified by column chromatography over silica gel (eluent: $CH_2Cl_2/CH_3OH/NH_4OH$ 98/2/0.1; 15-40 μm). Three fractions were collected and the solvent was evaporated. Yield: 0.189 g of fraction 1, 0.14 g of fraction 2 and 0.5 g of fraction 3 (48%). Fraction 3 was purified by column chromatography over kromasil (eluent: $CH_2Cl/EtOAc$ 80/20; 10 μm). Two fractions (F1, F2) were collected and the solvent was evaporated. Yield: 0.25 g F1 (24%) and 0.1 g of F2. F1 was crystallized from diethyl ether. The precipitate was filtered off and dried. Yield: 0.21 g of intermediate 32 (20%).

e-3) The preparation of intermediate 34

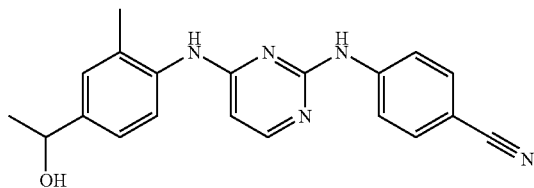 [SMILES: Cc1cc(C(C)O)ccc1Nc1ccnc(Nc2ccc(C#N)cc2)n1]

A solution of methylmagnesium iodide (1.0M solution in diethylether) (0.6 ml) was added to a solution of

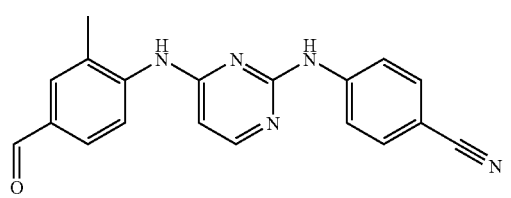 [SMILES: Cc1cc(C=O)ccc1Nc1ccnc(Nc2ccc(C#N)cc2)n1]

intermediate 33 (prepared according to A5.a) (0.0006 mol) in THF (3 ml). The mixture was stirred for 2 hours. $H_2O$ was added. The mixture was filtered over celite. $H_2O$ was added. The mixture was extracted with EtOAc. The organic layer was separated, dried ($MgSO_4$), filtered, and the solvent was evaporated. The residue (0.05 g) was purified by column chromatography over silica gel (eluent: $CH_2Cl_2/CH_3OH$ 96/4; 15-40 μm). The pure fractions were collected and the solvent was evaporated. Yield: 0.015 g of intermediate 34 (7.2%).

Example A4 a) The Preparation of Intermediate 10

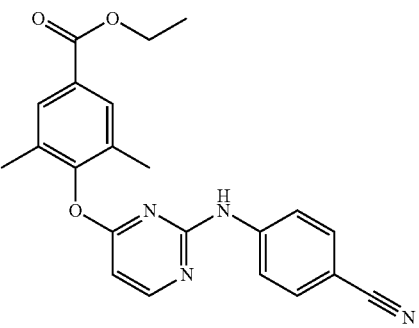 [SMILES: CCOC(=O)c1cc(C)c(Oc2ccnc(Nc3ccc(C#N)cc3)n2)c(C)c1]

A mixture of ethyl 3,5-dimethyl-4-hydroxy benzoate (0.0025 mol) in 1,4-dioxane (2.5 mil) was stirred at room temperature under $N_2$ flow. Sodium hydride (0.0033 mol) was added. The mixture was stirred for 2 minutes. Intermediate 5 (0.0028 mol) was added. The mixture was stirred for 10 minutes. 1-methyl-2-pyrrolidinone (2.5 ml) was added. The mixture was stirred at 150° C. for 12 hours, poured out into $H_2O$ and extracted with $CH_2Cl_2/CH_3OH$. The organic layer was separated, dried ($MgSO_4$), filtered and the solvent was evaporated. The residue (1.7 g) was purified by column chromatography over silica gel (eluent: $CH_2Cl_2/CH_3OH$ 92/8; 15-40 μm). The pure fractions were collected and the solvent was evaporated. Yield: 0.7 g of intermediate 10 (70%).

b-1) The preparation of intermediate 11

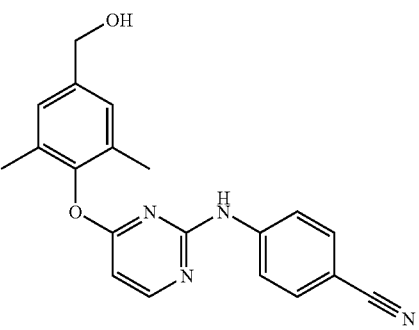 [SMILES: Cc1cc(CO)cc(C)c1Oc1ccnc(Nc2ccc(C#N)cc2)n1]

A solution of intermediate 10 (0.0005 mol) in THF (5 ml) was added dropwise at 0° C. to a suspension of $LiAlH_4$ (0.001 mol) in THF (5 ml) under $N_2$ flow. The mixture was stirred at 0° C. for 1 hour and poured out into $H_2O$ (0.5 ml). $CH_2Cl_2$ was added. The organic layer was separated, dried ($MgSO_4$), filtered, and the solvent was evaporated. The residue was purified by column chromatography over kromasil (eluent: $CH_2Cl_2$ 100 to $CH_2Cl_2/CH_3OH$ 99/1; 5 μm). The pure fractions were collected and the solvent was evaporated. The residue (0.1 g) was crystallized from diethyl ether. The precipitate was filtered off and dried. Yield: 0.043 g of intermediate 11 (24%).

b-2) The preparation of intermediate 37

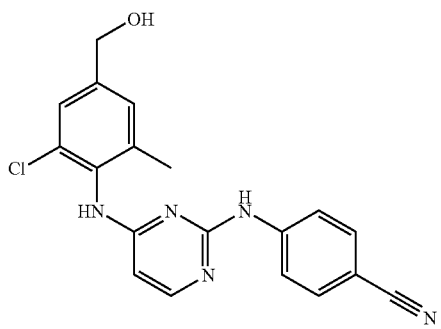 [SMILES: Cc1cc(CO)cc(Cl)c1Nc1ccnc(Nc2ccc(C#N)cc2)n1]

LiAlH$_4$ (0.0196 mol, 0.75 g) was added portionwise at 5° C. to a mixture of intermediate 29 (prepared according to A3d-2) (0.0098 mol) in THF (100 ml) under N$_2$ flow. The mixture was stirred at room temperature overnight, poured out into EtOAc, then into H$_2$O and filtered over celite. The organic layer was separated, dried (MgSO$_4$), filtered, and the solvent was evaporated. Yield: 3.4 g. This fraction was purified by column chromatography over kromasil (eluent: CH$_2$Cl$_2$/CH$_3$OH/NH$_4$OH 97/3/0.1; 15-40 µm). The pure fractions were collected and the solvent was evaporated. Yield 1 g (27%). This fraction was crystallized from DIPE/CH$_3$CN. The precipitate was filtered off and dried. Yield: 0.03 g of intermediate 37.

c) The Preparation of Intermediate 12

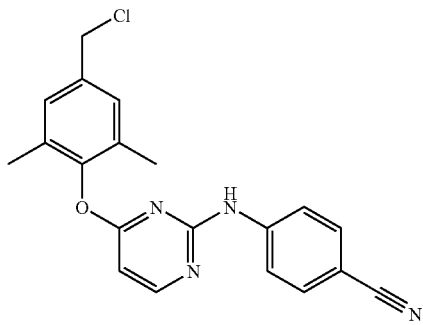 [SMILES: Cc1cc(CCl)cc(C)c1Oc1ccnc(Nc2ccc(C#N)cc2)n1]

A mixture of intermediate 11 (0.0043 mol) in CH$_2$Cl$_2$ (50 ml) was stirred at 0° C. SOCl$_2$ (0.0206 mol) was added dropwise. The mixture was poured out into ice water/K$_2$CO$_3$. The mixture was stirred at room temperature for 5 minutes. The organic layer was separated, dried (MgSO$_4$), filtered, and the solvent was evaporated. Yield: 1.5 g of intermediate 12 (98%).

d) The Preparation of Intermediate 55

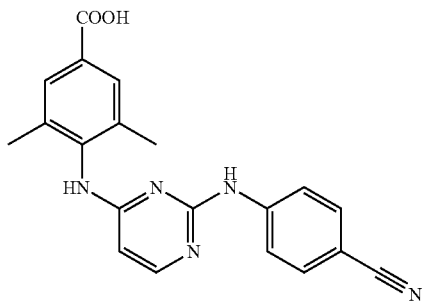 [SMILES: Cc1cc(C(=O)O)cc(C)c1Nc1ccnc(Nc2ccc(C#N)cc2)n1]

Jones's reagent (0.0084 mol) was added to a mixture of intermediate 19 (see Table 1) (prepared according to A4b-1) (0.0028 mol) in acetone (50 ml). The mixture was stirred at room temperature for 2 hours then poured out into H$_2$O and basified with NaHCO$_3$. The precipitate was filtered off and dried. Yield: 1.39 g. The residue (0.1 g) was purified by column chromatography over silica gel (eluent: CH$_2$Cl$_2$/CH$_3$OH/NH$_4$OH 85/15/1 then CH$_3$OH 100). The pure fraction was crystallized from isopropanol/DIPE. Yield: 0.071 g of intermediate 55.

Example A5 a) The Preparation of Intermediate 13

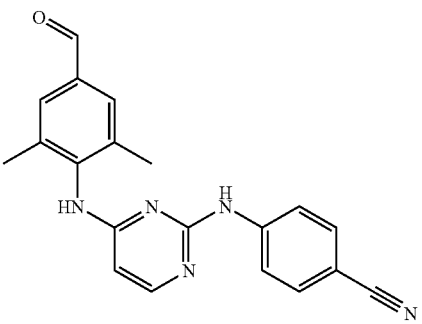 [SMILES: Cc1cc(C=O)cc(C)c1Nc1ccnc(Nc2ccc(C#N)cc2)n1]

A mixture of intermediate 19 (see Table 1) (prepared according to A4.b-1) (0.0037 mol) and MnO$_2$ (0.0185 mol) in CH$_2$Cl$_2$ (100 ml) was stirred at room temperature overnight, then filtered over celite. The filtrate was evaporated. Yield: 1.3 g of intermediate 13.

b) The Preparation of Intermediate 21

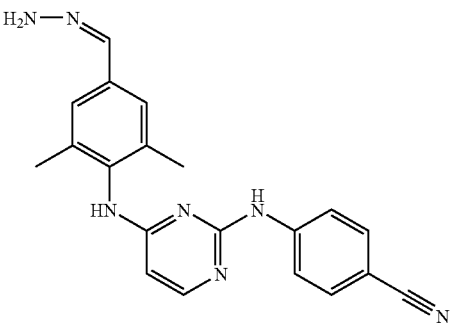 [SMILES: Cc1cc(/C=N\N)cc(C)c1Nc1ccnc(Nc2ccc(C#N)cc2)n1]

A mixture of intermediate 13 (prepared according to A5.a) (0.0029 mol) and H$_2$N—NH$_2$, H$_2$O (0.0058 mol) in EtOH (10 ml) was stirred at room temperature overnight. The solvent was evaporated till dryness. Yield: 0.53 g of intermediate 21.

Example A6

The preparation of intermediate 14

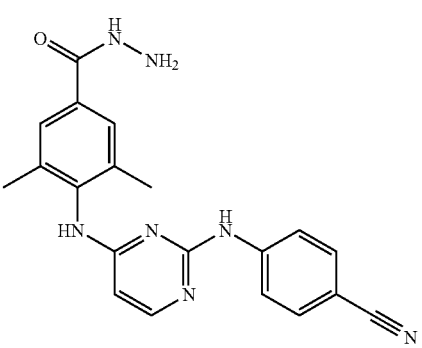 [SMILES: Cc1cc(C(=O)NN)cc(C)c1Nc1ccnc(Nc2ccc(C#N)cc2)n1]

Hydrazine (0.0077 mol) was added to a mixture of

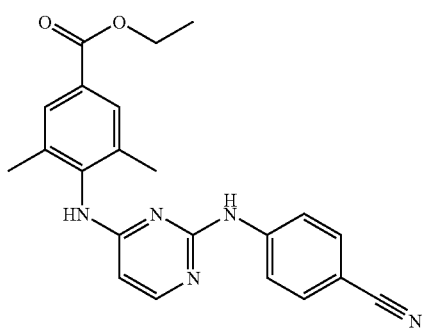

(prepared according to A3.d-1) (0.0005 mol) in EtOH (10 ml). The mixture was stirred and refluxed overnight. Hydrazine (0.028 mol) was added. The mixture was stirred and refluxed overnight. Yield: 0.28 g of intermediate 14.

Example A7 a) The Preparation of Intermediate 23

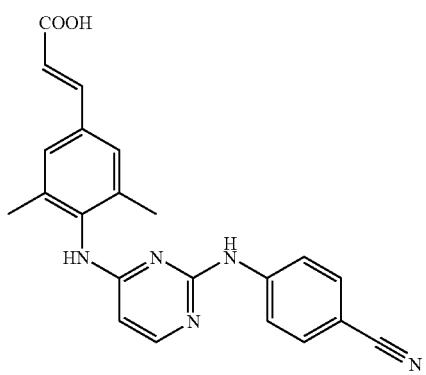 [SMILES: Cc1cc(/C=C/C(=O)O)cc(C)c1Nc1ccnc(Nc2ccc(C#N)cc2)n1]

A mixture of intermediate 35

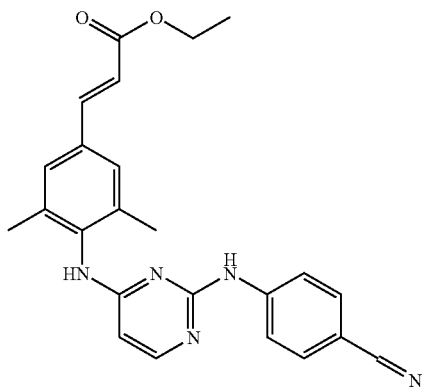 [SMILES: CCOC(=O)/C=C/c1cc(C)c(Nc2ccnc(Nc3ccc(C=N)cc3)n2)c(C)c1]

(prepared according to A3.d-1) (0.0056 mol) in HCl 3N (60 ml) and iPrOH (15 ml) was stirred and refluxed overnight. The precipitate was filtered, washed with H$_2$O, taken up in DIPE and dried. Yield: 2.3 g of intermediate 23 (100%).

b) The Preparation of Intermediate 56

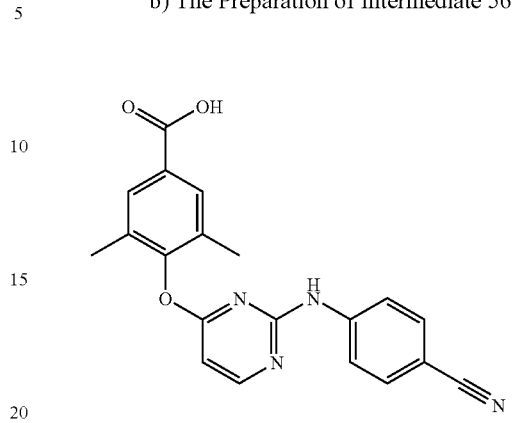

A mixture of intermediate 10 (prepared according to A4.a) (0.0012 mol) in HCl 3N (26 ml) and iPrOH (4 ml) was stirred and refluxed for 12 hours. The solvent was evaporated till dryness. The residue was taken up in (CH$_3$)$_2$CO. The solvent was evaporated. The residue was taken up in diethyl ether. The precipitate was filtered off and dried. Yield: 0.4 g (78.5%). This fraction was stirred at 60° C. for 20 minutes. Yield: 0.19 g. This fraction was crystallized from H$_2$O/2-propanone. The precipitate was filtered off and dried. Yield: 0.12 g of intermediate 56 (26%).

Example A8 a) The Preparation of Intermediate 24

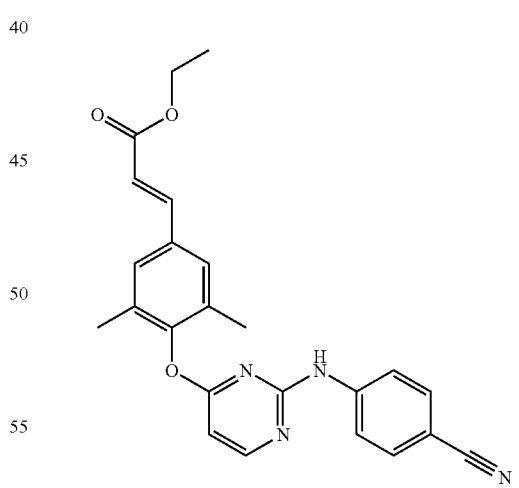

A mixture of intermediate 31 (prepared according to A4.a) (0.0005 mol) and (triphenylphosphoranylidene)acetic acid ethyl ester [CAS 1099-45-2] (0.0006 mol in THF (5 ml) was stirred at 80° C. for 48 hours, poured out into H$_2$O and extracted with CH$_2$Cl$_2$. The organic layer was separated, dried (MgSO$_4$), filtered and the solvent was evaporated. The residue (0.4 g) was crystallized from DIPE. The precipitate was filtered off and dried. Yield: 0.08 g (33%). This fraction was crystallized from DIPE/CH₃CN. The precipitate was filtered off and dried. Yield: intermediate 24 (33%).

b) The Preparation of Intermediate 25

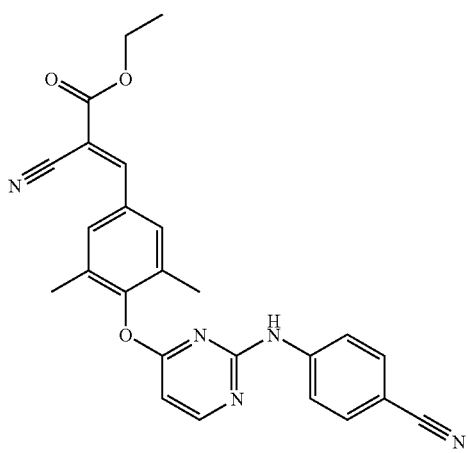 [SMILES: CCOC(=O)/C(C#N)=C/c1cc(C)c(Oc2ccnc(Nc3ccc(C#N)cc3)n2)c(C)c1]

Piperidine (0.0011 mol) was added at room temperature for 30 minutes. Intermediate 31 (prepared according to A4.a) (0.0005 mol) was added. The mixture was stirred at room temperature for 1 hour, poured out into H₂O and extracted with CH₂Cl₂. The precipitate was filtered off and dried. The residue (0.2 g) was crystallized from CH₃CN/DIPE. The precipitate was filtered off and dried. Yield: 0.048 g of intermediate 25 (19%) (mp. 222° C.).

Example A9

The Preparation of Intermediate 26

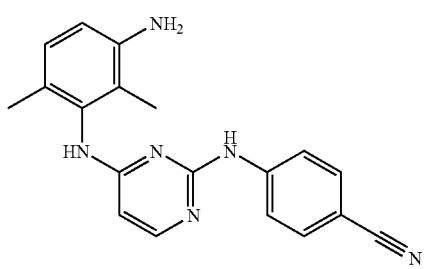 [SMILES: Cc1ccc(N)c(C)c1Nc1ccnc(Nc2ccc(C#N)cc2)n1]

A mixture of

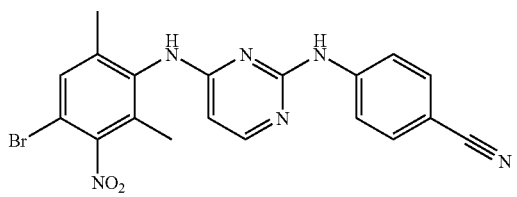 [SMILES: Cc1cc(Br)c([N+](=O)[O-])c(C)c1Nc1ccnc(Nc2ccc(C#N)cc2)n1]

(prepared according to A3.d-1) (0.0011 mol) and Pd/C (0.2 g) in methanol (30 ml) was hydrogenated at room temperature for 2 hours under one bar pressure, then filtered over celite. Celite was washed with CH₃OH. The filtrate was evaporated till dryness. The residue (0.3 g) was crystallized from 2-propanone/CH₃OH/diethyl ether. The precipitate was filtered off and dried. Yield: 0.07 g of fraction 1. Fraction 1 was purified by column chromatography over kromasyl (eluent: CH₂Cl₂/CH₃OH 99.5/0.5; 5 μm). Three fractions (F1, F2, F3) were collected and the solvent was evaporated. Yield: 0.0516 g F1, 0.1 g F2 and 0.15 g F3. F1 was taken up in diethyl ether. The precipitate was filtered off and dried. Yield: 0.028 g of intermediate 26 (8%) (mp. 272° C.).

Example A10

The Preparation of Intermediate 27

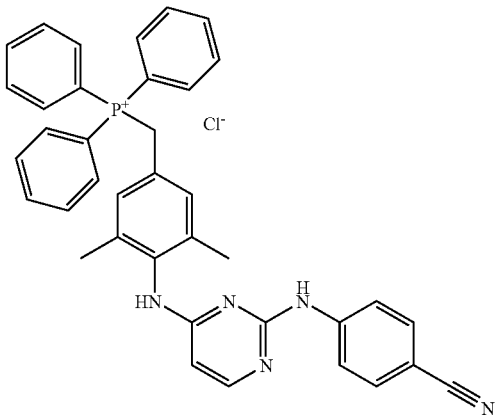 [SMILES: Cc1cc(C[P+](c2ccccc2)(c2ccccc2)c2ccccc2)cc(C)c1Nc1ccnc(Nc2ccc(C#N)cc2)n1 ; [Cl-]]

A mixture of

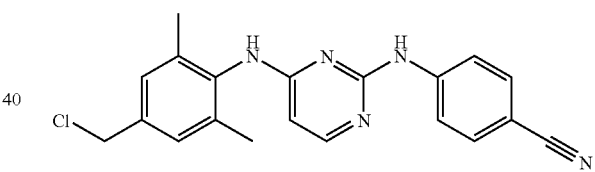

(prepared according to A4.c) (0.0005 mol) and triphenylphosphine (0.0005 mol) in CH₃CN (10 ml) was stirred and refluxed for a week end. The solvent was evaporated till dryness. The residue was taken up in diethyl ether. The precipitate was filtered off and dried. Yield: 0.34 g of intermediate 27 (94%).

Example A11

The Preparation of Intermediate 58

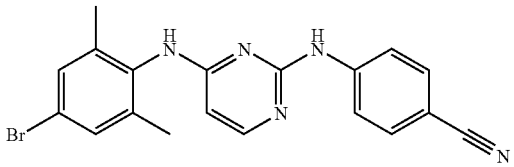 [SMILES: Cc1cc(Br)cc(C)c1Nc1ccnc(Nc2ccc(C#N)cc2)n1]

A mixture of 4-bromo-2,6-dimethylbenzenamine (0.013 mol) and intermediate 5 (0.013 mol) was stirred at 150° C. for 1 hour. The mixture was poured into K₂CO₃ 10% aqueous solution and extracted with CH₂Cl₂/MeOH (95/5). The organic layer was separated, dried (MgSO₄), filtered and the solvent was evaporated. The residue was crystallized from diisopropyl ether. The precipitate was filtered off and dried. Yield: 2.3 g (45%). The mother layer was purified by column chromatography over silica gel (eluent: $CH_2Cl_2/CH_3OH$—$NH_4OH$ 98.5/1.5; 15-40 μm). The pure fractions were collected and the solvent was evaporated. Yield: 0.90 g (17%). The global yield of intermediate 5 was: 3.2 g (62%).

Intermediate 59 was prepared analogously.

Intermediate 59

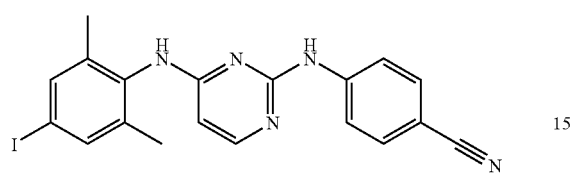

Table 1 and 2 list intermediates which intervene in the preparation of compounds of formula (I).

TABLE 2

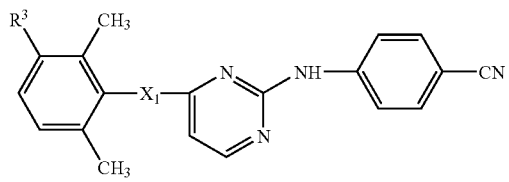

| Interm. No. | Ex. No. | $X_1$ | $R^3$ | Physical data |
|---|---|---|---|---|
| 20 | A3e | NH | —CHOH—$CH_3$ | |

TABLE 1

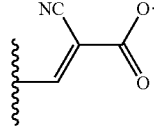

| Interm. No. | Ex. No. | $X_1$ | $R^3$ | $R^{4a}$ | $R^{4b}$ | Physical data |
|---|---|---|---|---|---|---|
| 11 | A4b-1 | O | —$CH_2$—OH | $CH_3$ | $CH_3$ | |
| 12 | A4c | O | —$CH_2$—Cl— | $CH_3$ | $CH_3$ | |
| 16 | A3e | NH | —CH(OH)—$CH_3$ | $CH_3$ | $CH_3$ | |
| 17 | A3e | NH | —CH(OH)—CH($CH_3$)$_2$ | $CH_3$ | $CH_3$ | |
| 18 | A3e | NH | —(CH—OH)—$CH_2$—$CH_3$ | $CH_3$ | $CH_3$ | |
| 19 | A4b-1 | NH | —$CH_2$—OH | $CH_3$ | $CH_3$ | |
| 15 | A4c | NH | —$CH_2$—Cl | $CH_3$ | $CH_3$ | |
| 24 | A8a | O | —CH=CH—C(=O)—O—$C_2H_5$ | $CH_3$ | $CH_3$ | mp. 180° C.; (E) |
| 25 | A8b | O | NC / O—$C_2H_5$ (see structure) | $CH_3$ | $CH_3$ | mp. 222° C.; (A) |
| 35 | A3d-1 | NH | —CH=CH—C(=O)—O—$C_2H_5$ | $CH_3$ | $CH_3$ | mp. 200° C.; (E) |
| 23 | A7a | NH | —CH=CH—COOH | $CH_3$ | $CH_3$ | |
| 34 | A3e-3 | NH | —CH(OH)—$CH_3$ | $CH_3$ | H | mp. 182° C. |
| 36 | A4b-1 | NH | —$CH_2$—OH | $CH_3$ | H | mp. 210° C. |
| 37 | A4b-2 | NH | —$CH_2$—OH | Cl | $CH_3$ | |
| 38 | A4b-1 | NH | —$CH_2$—OH | Cl | H | mp. 226° C. |
| 39 | A3e-1 | O | —CH(OH)—$CH_3$ | $CH_3$ | H | mp. 160° C. |
| 40 | A4b-1 | S | —$CH_2$—OH | $CH_3$ | $CH_3$ | mp. 173° C. |
| 41 | A4b-1 | NH | —$CH_2$—OH | Br | H | mp. 234° C. |
| 32 | A3e-2 | O | —CH(OH)—$CH_3$ | $CH_3$ | $CH_3$ | mp. 193° C. |
| 42 | A4b-1 | NH | —$CH_2$—OH | Br | $CH_3$ | mp. 250° C. |
| 43 | A4b-1 | NH | —$CH_2$—OH | OH | H | mp. 124° C. |
| 44 | A4b-1 | NH | —$CH_2$—OH | H | H | mp. 215° C. |
| 45 | A4b-1 | NH | —$CH_2$—OH | O—$CH_3$ | H | |
| 46 | A4b-1 | NH | —$CH_2$—OH | $CF_3$ | H | mp. 194° C. |
| 47 | A4c | NH | —$CH_2$—Cl | Cl | $CH_3$ | |
| 48 | A4c | NH | —$CH_2$—Cl | Cl | H | |
| 49 | A3e-1 | O | —$CH_2$—OH | $CH_3$ | H | |
| 50 | A4c | O | —$CH_2$—Cl | $CH_3$ | H | |
| 51 | A4b-1 | NH | —$CH_2$—OH | C($CH_3$)$_3$ | H | |
| 52 | A4c | NH | —$CH_2$—Cl | $CH_3$ | H | |
| 53 | A4b-1 | NH | —$CH_2$—OH | 2-furanyl | $CH_3$ | |
| 54 | A4c | NH | —$CH_2$—Cl | Br | $CH_3$ | |
| 57 | A7b | O | —CH=CH—COOH | $CH_3$ | $CH_3$ | |

B. Preparation of the Final Compounds

Example B1

The Preparation of Compound 1

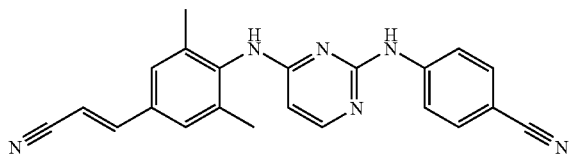 [SMILES: Cc1cc(/C=C/C#N)cc(C)c1Nc1ccnc(Nc2ccc(C#N)cc2)n1]

A mixture of intermediate 3 (0.034 mol) and intermediate 5 (0.0174 mol) was stirred at 150° C. for 1 hour and taken up in $K_2CO_3$ 10%/$CH_2Cl_2$/$CH_3OH$. The organic layer was separated, dried ($MgSO_4$), filtered, and the solvent was evaporated. The residue (10 g) was purified by column chromatography over silica gel (eluent: $CH_2Cl_2$/ethyl acetate 80/20; 15-40 μm). Fraction 1 was crystallized from iPrOH. The precipitate was filtered off and dried. Yield: 1.3 g of 4-[[4-[[4-(2-cyanoethenyl)-2,6-dimethylphenyl]amino]-2-pyrimidinyl]amino]benzonitrile (E) (compound 1) (20%).

Example B1A

Compound 1 was also prepared as follows:
A mixture of 93.9 g (0.45 mol) of the hydrochloric acid salt of intermediate 3, prepared according to Example A1c), and 109 g (0.4725 mol) of intermediate 5 in 1.8 l of acetonitrile was prepared under nitrogen atmosphere. The mixture was stirred and refluxed for 69 hours, then allowed to cool to 55° C. The mixture was filtered and the residue was washed with 200 ml of acetonitrile, followed by drying under reduced pressure at 50° C. overnight. 144.6 g (0.3666 mol) of the obtained solid was brought in 1 l of $K_2CO_3$ 10% aqueous solution. The mixture was stirred at room temperature followed by filtration. The obtained residue was washed twice with water followed by drying at 50° C. under reduced pressure. The residue was brought in 6.55 l isopropanol and the mixture was refluxed, then stirred overnight and filtered at room temperature. The residue was was dried at 50° C. under reduced pressure. Yield: 113.2 g (68.6%) of 4-[[4-[[4-(2-cyanoethenyl)-2,6-dimethylphenyl]amino]-2-pyrimidinyl]amino]benzonitrile (E) (compound 1).

Example B1B

Alternatively, compound 1 was also prepared as follows:
a) A mixture of intermediate 58 (0.00021 mol), prepared according to Example A11, acrylonitrile ($CH_2$=CH—CN) (0.00213 mol), Pd(OAc)$_2$ (0.000043 mol), N,N-diethylethanamine (0.000043 mol) and tris(2-methylphenyl)phosphine (0.00021 mol) in $CH_3CN$ (7 ml) was stirred in a sealed vessel at 150° C. overnight $H_2O$ was added. The mixture was extracted with $CH_2Cl_2$. The organic layer was separated, dried ($MgSO_4$), filtered and the solvent was evaporated. The residue (0.15 g) was purified by column chromatography over silica gel (eluent: $CH_2Cl_2$/ethyl acetate 80/20; 15-40 μm). Fraction 1 was collected and the solvent was evaporated, yielding 0.045 g of 4-[[4-[[4-(2-cyanoethenyl)-2,6-dimethylphenyl]amino]-2-pyrimidinyl]amino]benzonitrile (E/Z=80/20). The solid was crystallized from diethylether. Yield: 0.035 g of 4-[[4-[[4-(2-cyanoethenyl)-2,6-dimethylphenyl]amino]-2-pyrimidinyl]amino]benzonitrile (E) (compound 1) (55%).

b) 4.41 g (10 mmol) of intermediate 59 and 15 ml of N,N-dimethylacetamide were brought in a 100 ml flask under nitrogen. To this mixture were added 0.98 g of sodium acetate (12 mmol), 107 mg (0.1 mmol Pd) of Pd/C 10% (wet) and 1 ml (15 mmol) of acrylonitrile. The mixture was heated at 140° C. and the evolution of the reaction was followed by liquid chromatography. The reaction yielded 4-[[4-[[4-(2-cyanoethenyl)-2,6-dimethylphenyl]amino]-2-pyrimidinyl]amino]benzonitrile (E/Z=80/20) which can be converted to 4-[[4-[[4-(2-cyanoethenyl)-2,6-dimethylphenyl]amino]-2-pyrimidinyl]amino]benzonitrile (E) as described above in Example B1Ba).

Example B2 a) The Preparation of Compound 2

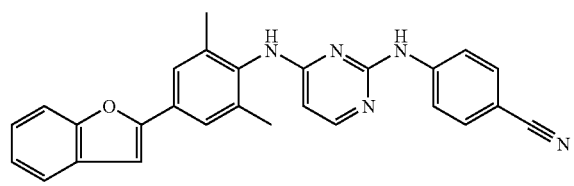 [SMILES: Cc1cc(-c2cc3ccccc3o2)cc(C)c1Nc1ccnc(Nc2ccc(C#N)cc2)n1]

A mixture of

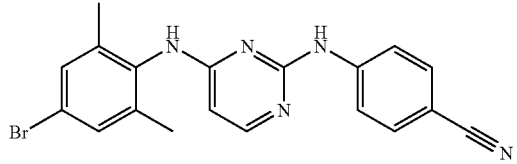 [SMILES: Cc1cc(Br)cc(C)c1Nc1ccnc(Nc2ccc(C#N)cc2)n1]

(prepared according to A3.d-1) (0.0002 mol), 2-benzofuranylboronic acid (0.0005 mol), Pd(PPh$_3$)$_4$ (0.00002 mol) and Na$_2$CO$_3$ (0.0007 mol) in DME (3 ml) was stirred and refluxed in a scelled tube for 3 hours. H$_2$O was added. The mixture was extracted with ethyl acetate. The organic layer was separated, dried (MgSO$_4$), filtered and the solvent was evaporated. The residue (0.126 g) was purified by column chromatography over silica gel (eluent: CH$_2$Cl$_2$/CH$_3$OH 98/2; 15-40 μm). The pure fractions were collected and the solvent was evaporated. Yield: 0.011 g of compound 2 (10%).

b) The Preparation of Compound 3

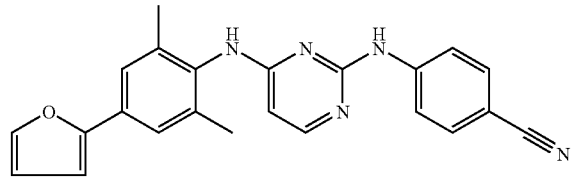 [SMILES: Cc1cc(-c2ccco2)cc(C)c1Nc1ccnc(Nc2ccc(C#N)cc2)n1]

A mixture of

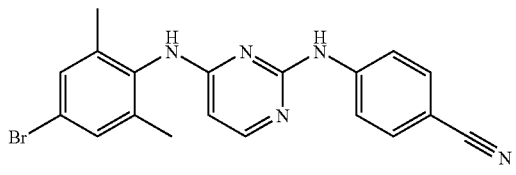 [SMILES: Cc1cc(Br)cc(C)c1Nc1ccnc(Nc2ccc(C#N)cc2)n1]

(prepared according to A3.d-1) (0.0002 mol), tributyl-2-furanylstannane (0.0005 mol) and Pd(PPh$_3$)$_4$ (0.00001 mol) in dioxane (5 ml) was stirred at 80° C. The solvent was evaporated. The residue was purified by column chromatography over silica gel (eluent: CH$_2$Cl$_2$/CH$_3$OH 98/2; 15-40 μm). The pure fractions were collected and the solvent was evaporated. The residue (0.025 g) was crystallieed from DIPE. The precipitate was filtered off and dried. Yield: 0.021 g of compound 3 (22%).

c) The Preparation of Compound 104

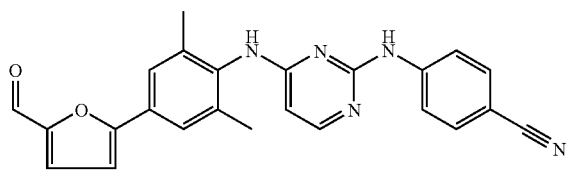 [SMILES: Cc1cc(-c2ccc(C=O)o2)cc(C)c1Nc1ccnc(Nc2ccc(C#N)cc2)n1]

A mixture of

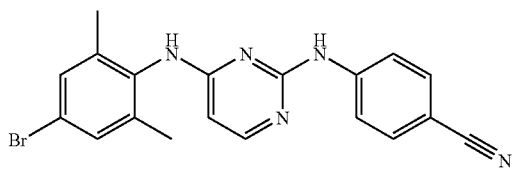 [SMILES: Cc1cc(Br)cc(C)c1Nc1ccnc(Nc2ccc(C#N)cc2)n1]

(prepared according to A3.d) (0.005 mol),

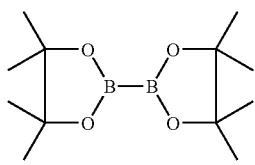

[CAS 73183-34-3] (0.0055 mol), Pd(PPh$_3$)$_4$ (0.29 g) and K$_2$CO$_3$ (2.8 g, 0.02 mol) in toluene (100 ml) and ethanol/water (5 to 10 ml) was stirred and refluxed for a weekend. 5-Bromo-furan-2-carbaldehyde (0.0055 mol) and K$_2$CO$_3$ (1.4 g, 0.01 mol) were added. The mixture was stirred and refluxed overnight. The mixture (2.25 g) was purified by column chromatography over silica gel (eluent: CH$_2$Cl$_2$/CH$_3$OH 100/0 to 99/1; 15-40 mm). The pure fractions were collected and the solvent was evaporated. Yield: 0.135 g of compound 104 (6%).

Example B3

The Preparation of Compound 4

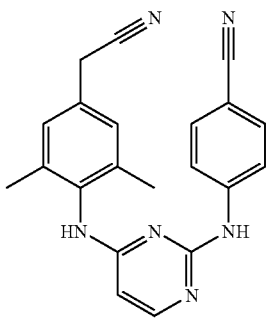 [SMILES: Cc1cc(CC#N)cc(C)c1Nc1ccnc(Nc2ccc(C#N)cc2)n1]

A mixture of intermediate 15 (see Table 1) (prepared according to A4.c) (0.0005 mol) and NaCN (0.0011 mol) in DMF (5 ml) was stirred at 80° C. overnight, poured out into H$_2$O and extracted with ethyl acetate. The organic layer was separated, dried MgSO$_4$), filtered, and the solvent was evaporated. The residue (0.15 g) was purified by column chromatography over kromasil (eluent: CH$_2$Cl$_2$/CH$_3$OH 99/1; 10 μm). The pure fractions were collected and the solvent was evaporated. The residue (0.024 g) was purified by column chromatography over hypersil (eluent: acetonitrile/H$_2$O 52/48; 8 μm). The pure fractions were collected and the solvent was evaporated. Yield: 0.02 g of compound 4 (10%).

Example B4 a) The Preparation of Compound 5

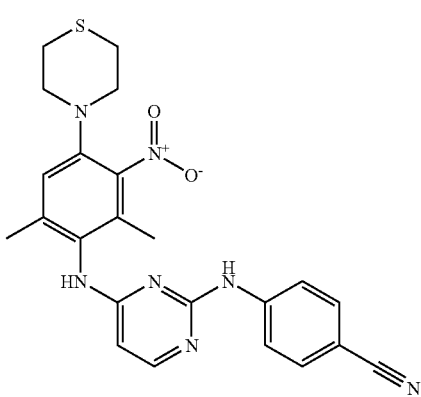 [SMILES: Cc1cc(N2CCSCC2)c([N+](=O)[O-])c(C)c1Nc1ccnc(Nc2ccc(C#N)cc2)n1]

A mixture of

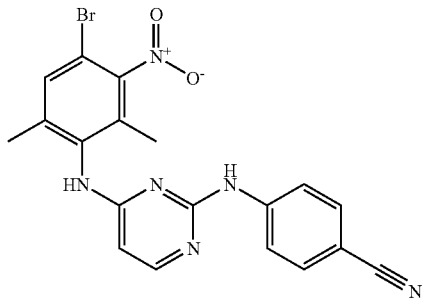 [SMILES: Cc1cc(Br)c([N+](=O)[O-])c(C)c1Nc1ccnc(Nc2ccc(C#N)cc2)n1]

(prepared according to A3.d) (0.0006 mol) and thiomorpholine (0.5 g) was stirred at 120° C. for 48 hours, taken up in CH$_2$Cl$_2$ and the solvent was evaporated. The residue (0.44 g) was purified by column chromatography over kromasyl (eluent: CH$_2$Cl$_2$/CH$_3$OH 99/1; 10 μm). The pure fractions were collected and the solvent was evaporated. Yield: 0.06 g (20%). This fraction was crystallized from diethyl ether/2-propanone. The precipitate was filtered off and dried. Yield: 0.035 g of compound 5.

b) The Preparation of Compound 6

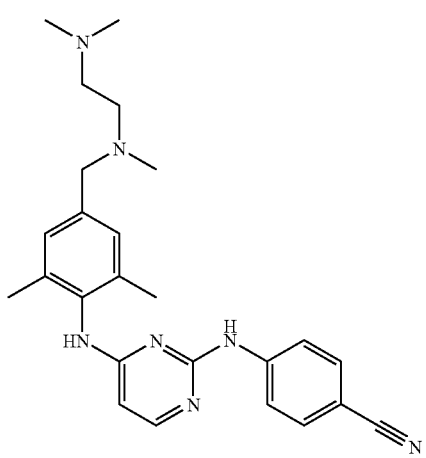 [SMILES: Cc1cc(CN(C)CCN(C)C)cc(C)c1Nc1ccnc(Nc2ccc(C#N)cc2)n1]

A mixture of intermediate 15 (see Table 1) (prepared according to A4.c) (0.000137 mol), N,N,N'-trimethyl-1,2-ethanediamine (2 equiv, 0.000275 mol) and K$_2$CO$_3$ (2 equiv, 0.000275 mol) in CH$_3$CN (q.s.) was stirred at 80° C. for 12 hours. H$_2$O was added. The mixture was extracted with CH$_2$Cl$_2$. The extracts solvent was evaporated. The residue was purified by chromatography. The product fractions were collected and the solvent was evaporated. Yield: 0.006 g of compound 6 (10.16%).

c) The Preparation of Compound 7

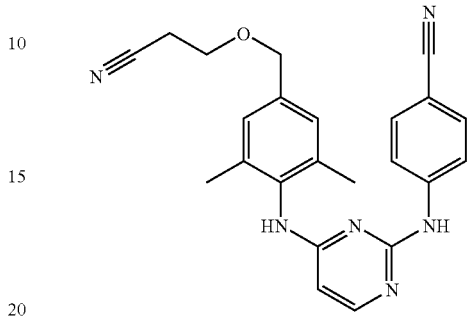

A mixture of intermediate 15 (see Table 1) (prepared according to A4.c) (0.0005 mol) in 3-hydroxy-propanenitrile (2 ml) was stirred overnight, poured out into H$_2$O and extracted with CH$_2$Cl$_2$. The organic layer was separated, dried (MgSO$_4$), filtered, and the solvent was evaporated. The residue was purified by column chromatography over silica gel (eluent: CH$_2$Cl$_2$/CH$_3$OH/NH$_4$OH 99/1/0.1; 15-40 μm). Two fractions (F1, F2) were collected and the solvent was evaporated. Yield: 0.034 g F1 and 0.514 g F2. F2 was washed with HCl 3N and extracted with CH$_2$Cl$_2$. The organic layer was separated, dried (MgSO$_4$), filtered, and the solvent was evaporated. The residue was crystallized from DIPE. The precipitate was filtered off and dried. Yield: 0.039 g of compound 7 (18%)

d) The Preparation of Compound 105

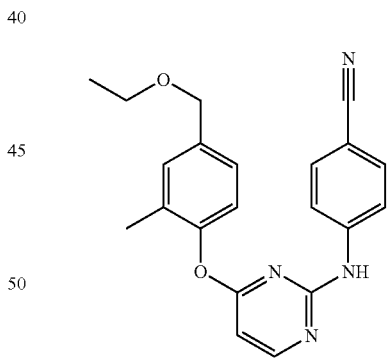

A mixture of intermediate 50 (prepared according to A4c) (0.001 mol), KCN (0.0011 mol) and KI (0.00005 mol) in EtOH (15 ml) was stirred and refluxed for 4 hours. The solvent was evaporated till dryness. The residue was taken up in CH$_2$Cl$_2$/H$_2$O. The mixture was extracted with CH$_2$Cl$_2$. The organic layer was separated, dried MgSO$_4$), filtered, and the solvent was evaporated. The residue (0.31 g) was purified by column chromatography over kromasil (eluent: cyclohexane/EtOAc 70/30; 10 μm). Three fractions were collected and the solvent was evaporated. Yield: 0.044 g of fraction 1, 0.11 g of fraction 2 and 0.055 g of fraction 3. Fraction 3 was crystallized from DIPE. The precipitate was filtered off and dried. Yield: 0.046 g of compound 105 (12%) (mp. 140° C.).

Example B5 a) The Preparation of Compound 8

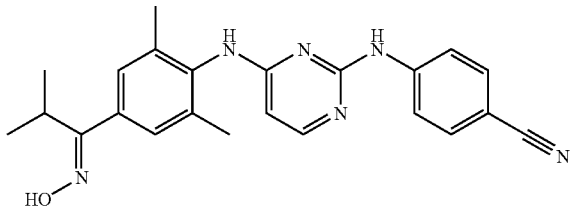 [SMILES: Cc1cc(/C(=N/O)C(C)C)cc(C)c1Nc1ccnc(Nc2ccc(C#N)cc2)n1]

A mixture of intermediate 9 (0.0001 mol) and hydroxylamine (0.0002 mol) in EtOH (7 ml) was stirred at room temperature for 3 hours, poured out into $K_2CO_3$ 10% and extracted with $CH_2Cl_2$. The organic layer was separated, dried ($MgSO_4$), filtered and the solvent was evaporated. The residue (0.1 g) was crystallized from $DIPE/CH_3CN$. The precipitate was filtered off and dried. Yield: 0.026 g of compound 8.

b) The Preparation of Compound 9

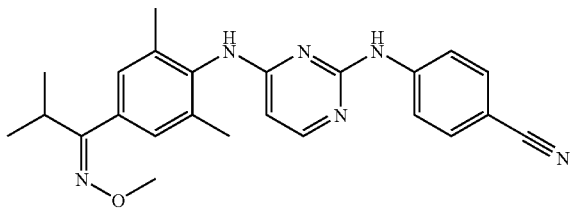 [SMILES: CO/N=C(\c1cc(C)c(Nc2ccnc(Nc3ccc(C#N)cc3)n2)c(C)c1)C(C)C]

A mixture of intermediate 9 (0.0002 mol) and O-methylhydroxylamine (0.0003 mol) in EtOH (10 ml) was stirred at room temperature overnight, poured out into $H_2O$ and extracted with $CH_2Cl_2$. The organic layer was separated, dried ($MgSO_4$), filtered and the solvent was evaporated. The residue (0.13 g) was purified by column chromatography over kromasyl (eluent: cyclohexane/iPrOH/$NH_4OH$; 5 μm). The pure fractions were collected and the solvent was evaporated. The residue (0.06 g) was crystallized from DIPE. The precipitate was filtered off and dried. Yield: 0.036 g of compound 9 (34%).

Example B6 a) The Preparation of Compound 1 and 10

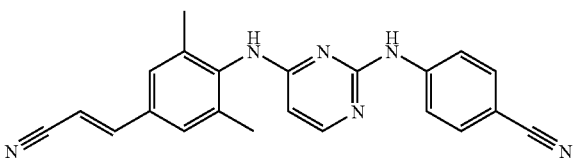

Compound 1 = (E); compound 10 = (Z)

A mixture of (cyanomethyl)triphenylphosphonium chloride (0.0022 mol) and potassium tert.-butoxide (0.0022 mol) in THF (7 ml) was stirred at 5° C. for 30 minutes under $N_2$ flow, then stirred at 5° C. for 30 minutes. A mixture of intermediate 13 (0.0015 mol) in THF (7 ml) was added. The mixture was stirred for 8 hours in darkness, poured out into $H_2O$ and extracted with $CH_2Cl_2$. The organic layer was separated, dried ($MgSO_4$), filtered and the solvent was evaporated. The residue (1.4 g) was purified by column chromatography over silica gel (eluent: toluene/iPrOH/$NH_4OH$ 96/4/0.1; 15-40 μm). Two fractions (F1, F2) were collected and the solvent was evaporated. Yield: 0.165 g of F1 (E/Z=32/68) (30%) and 0.225 g of F2 (E/Z=0/10) (41%). F2 was crystallized from $CH_3CN$/diethyl ether. Yield: 0.036 g of compound 1 (7%). F1 was purified by column chromatography over kromasyl (eluent: toluene/iPrOH 98/2; 5 μm). The pure fractions were collected and the solvent was evaporated. Yield: 0.029 g of compound 10 (5%).

b) The Preparation of Compound 11 (Z) and Compound 103 (E)

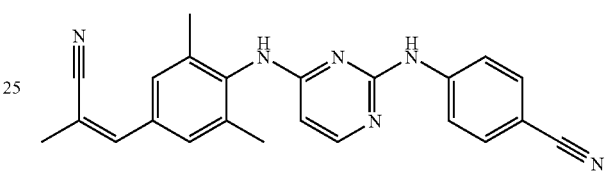

Potassium tert-terbutoxide (0.0196 mol) was added portionwise at 5° C. to a mixture of (1-cyanoethyl)-phosphonic acid diethyl ester (0.0196 mol) in THF (25 ml) under $N_2$ flow. The mixture was stirred at 5° C. for 30 minutes, then at room temperature for 30 minutes. A solution of intermediate 13 (0.0130 mol) in THF (25 ml) was added. The mixture was stirred at room temperature overnight, poured out into $H_2O$ and extracted with $CH_2Cl_2$. The organic layer was separated, dried ($MgSO_4$), filtered, and the solvent was evaporated. The residue (5.8 g) was purified by column chromatography over silica gel (eluent: toluene/iPrOH/NH4OH 92/8/0.5; 15-40 μm). Four fractions (F1, F2, F3, F4) were collected and the solvent was evaporated. Yield: 0.21 g of F1 (mixture Z/E=70/10), 0.836 g of F2 (mixture Z/E=57/43), 0.9 g of F3 and 0.87 g of F4. F3 was crystallized from DIPE/iPrOH to give 0.7 g of compound 11 (14%). F4 was crystallized from DIPE/iPrOH to give 0.67 g of compound 103 (13%).

c) The Preparation of Compound 12 and 13

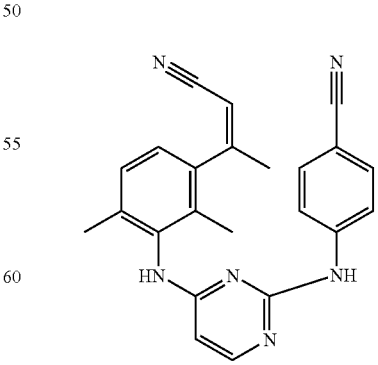

compound 12 = (E)
compound 13 = (Z)

Potassium tert.-butoxide (0.0008 mol) was added portionwise at 5° C. to a mixture of (cyanomethyl)phosphonic acid diethyl ester (0.0005 mol) in THF (20 ml) under N₂ flow. The mixture was stirred at room temperature for 30 minutes. A solution of

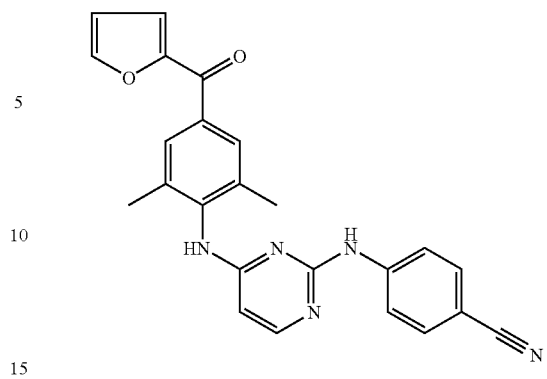

(prepared according to A3.d-1) (0.0009 mol) in THF (10 ml) was added. The mixture was stirred at room temperature for 4 hours, poured out into H₂O and extracted with ethyl acetate. The organic layer was separated, dried (MgSO₄), filtered, and the solvent was evaporated. The residue (0.17 g) was purified by column chromatography over kromasil (eluent: CH₂Cl₂ 100 to CH₂Cl₂/CH₃OH 99/1; 5 μm). Two fractions (F1, F2) were collected and the solvent was evaporated. Yield: 0.054 g F1 and 0.05 g F2. F1 was crystallized from DIPE/CH₃CN. The precipitate was filtered off and dried. Yield: 0.046 g of compound 14 (12%).

e) The Preparation of Compound 15

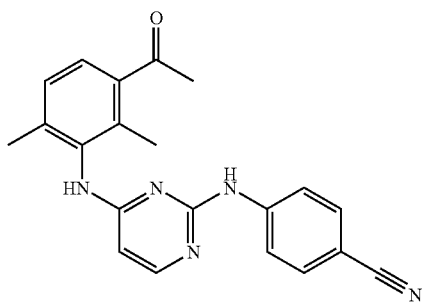 [SMILES: CC(=O)c1ccc(C)c(Nc2ccnc(Nc3ccc(C#N)cc3)n2)c1C]

(prepared according to A3.d-1) (0.0005 mol) in THF (4 ml) was added dropwise. The mixture was stirred at room temperature for 4 hours, poured out into H₂O and extracted with CH₂Cl₂. The organic layer was separated, dried (MgSO₄), filtered and the solvent was evaporated. Yield: 0.3 g. This fraction was purified by column chromatography over kromasil (eluent: CH₂Cl₂/CH₃OH 99/1; 5 μm). The pure fractions were collected and the solvent was evaporated. Yield: 0.21 g. This fraction was purified by column chromatography over kromasil (eluent: cyclohexane/ethyl acetate 50/50; 10 μm). Two fractions (F1, F2) were collected and the solvent was evaporated. Yield: 0.04 g of F1 and 0.047 g F2. F1 was dried at 70° C. for 2 hours. Yield: 0.038 g of compound 13 (18%). F2 was dried at 70° C. for 2 hours. Yield: 0.041 g of compound 12 (20%).

d) The Preparation of Compound 14

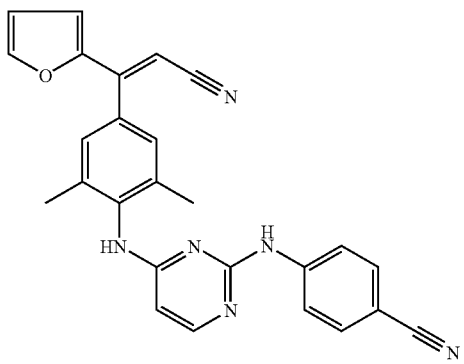 [SMILES: Cc1cc(/C(=C\C#N)c2ccco2)cc(C)c1Nc1ccnc(Nc2ccc(C#N)cc2)n1]

Potassium tert.-butoxide (0.0013 mol) was added at 5° C. to a mixture of (cyanomethyl)phoshonic acid diethyl ester (0.0013 mol) in THF (10 ml) under N₂ flow. The mixture was stirred at 5° C. for 30 minutes. A mixture of

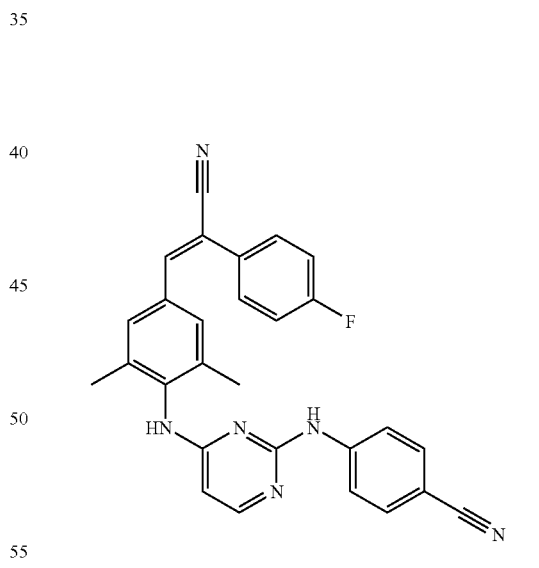

4-Fluorobenzeneacetonitrile (1.2 equiv, 0.000175 ml) was added to a mixture of intermediate 13 (0.000146 mol) in CH₃OH (1 ml). NaOCH₃/CH₃OH (1.2 equiv, 0.000175 mol) was added at room temperature. The mixture was stirred at 60° C. for 2 hours, then poured out into ice-water and extracted with CH₂Cl₂. The solvent was evaporated. The residue was purified by chromatography. The product frac-

77 tions were collected and the solvent was evaporated. Yield: 0.009 g of compound 15 (13.42%).

f) The Preparation of Compound 106

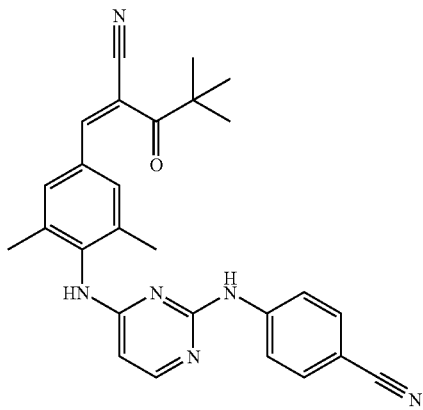 [SMILES: Cc1cc(/C=C(/C#N)C(=O)C(C)(C)C)cc(C)c1Nc1ccnc(Nc2ccc(C#N)cc2)n1]

A mixture of intermediate 13 (prepared according to A5.a) (0.0005 mol) and piperidine (0.0005 mol) in ethanol (5 ml) was stirred at room temperature for 30 minutes. 4,4-dimethyl-3-oxo-pentanenitrile (0.0011 mol) was added. The mixture was stirred at room temperature overnight, poured out into $H_2O$ and extracted with $CH_2Cl_2$. The organic layer was separated, dried ($MgSO_4$), filtered, and the solvent was evaporated. The residue (0.3 g) was purified by column chromatography over kromasil (eluent: $CH_2Cl_2/CH_3OH$ 99/1; 10 μm). The pure fractions were collected and the solvent was evaporated. The residue (0.2 g) was crystallized from DIPE. The precipitate was filtered off and dried. Yield: 0.141 g of compound 106 (54%) (mp. 193° C.).

Example B7

The Preparation of Compound 16

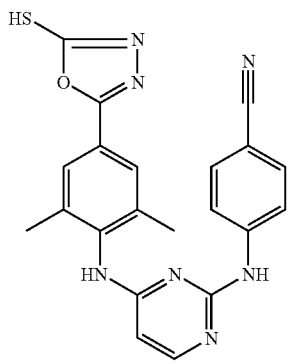 [SMILES: Cc1cc(-c2nnc(S)o2)cc(C)c1Nc1ccnc(Nc2ccc(C#N)cc2)n1]

A mixture of intermediate 14 (0.00005 mol) and carbonothioic dichloride (0.001 mol) in dioxane (10 ml) was stirred at room temperature. $H_2O$ was added. The mixture was extracted with $CH_2Cl_2$. This fraction was purified by column chromatography over silica gel (eluent: $CH_2Cl_2/CH_3OH/$

78

$NH_4OH$ 90/10/0.1; 15-40 μm). The pure fractions were collected and the solvent was evaporated. Yield: 0.027 g of compound 16 (95.6%).

Example 8

The Preparation of Compound 17

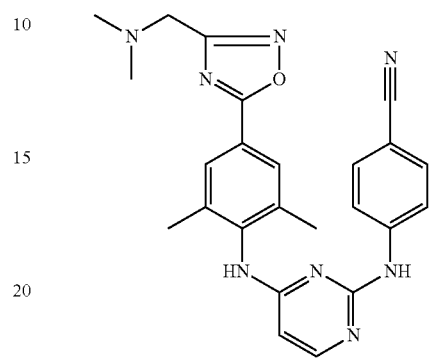

The mixture of $NaOCH_3$ (0.001 mol) and 2-(dimethylamino)-N-hydroxy-ethanimidamide (0.001 mol) in EtOH (10 ml) was stirred at room temperature for 30 minutes.

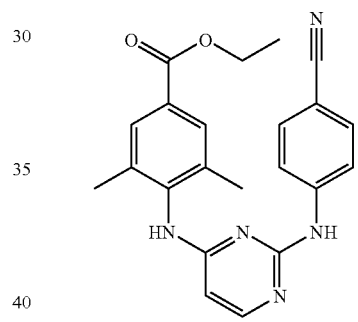

(prepared according to A3.d-1) (0.0005 mol) was added. The mixture was stirred and refluxed overnight. $H_2O$ was added. The mixture was extracted with $CH_2Cl_2$. The residue was purified by column chromatography over silica gel (eluent: $CH_2Cl_2/CH_3OH/NH_4OH$ 95/5/0.1; 15-40 μm). The pure fractions were collected and the solvent was evaporated. Yield: 0.07 g of compound 17 (31%).

Example B9

The Preparation of Compound 18

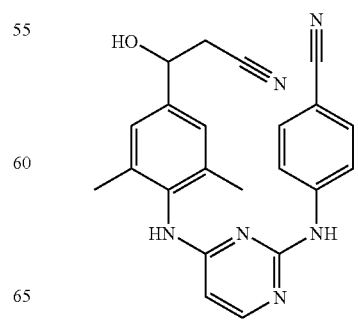

nBuLi (0.0038 mol) was added dropwise at −70° C. to a mixture of iPr$_2$NH (0.0038 mol) in THF (5 ml) under N$_2$ flow. The mixture was brought to −20° C., stirred for 30 minutes and cooled again to −70° C. A solution of CH$_3$CN (0.0038 mol) in THF (6 ml) was added dropwise. The mixture was brought to −20° C., stirred for 1 hour, cooled again to −70° C. A mixture of intermediate 13 (0.0009 mol) in THF (1 ml) was added. The mixture was stirred for 2 hours, poured out on ice at −30° C. and extracted with ethyl acetate. The organic layer was separated, dried (MgSO$_4$), filtered, and the solvent was evaporated. The residue (0.433 g) was purified by column chromatography over silica gel (eluent: CH$_2$Cl$_2$/CH$_3$OH 98/2; 35-70 µm). Two fractions were collected and the solvent was evaporated. Yield: 0.056 g F1 and 0.23 g F2 (78%). F1 was crystallized from DIPE/CH$_3$CN. The precipitate was filtered off and dried. Yield: 0.036 g of compound 18.

Example B9A a) The Preparation of Compound 107

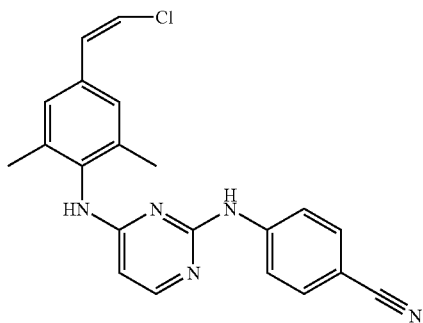 [SMILES: Cc1cc(/C=C\Cl)cc(C)c1Nc1ccnc(Nc2ccc(C#N)cc2)n1]

nBuLi[1.6] (0.0026 mol) was added dropwise at −70° C. to a mixture of intermediate 13 (prepared according to A5.a) (0.0008 mol) in THF (10 ml) under N$_2$ flow. The mixture was stirred at −70° C. for 30 minutes. A solution of (chloromethyl)triphenylphosphonium chloride (0.0026 mol) in THF (5 ml) was added dropwise. The mixture was stirred at room temperature overnight, poured out into H$_2$O and extracted with EtOAc. The organic layer was separated, dried (MgSO$_4$), filtered and the solvent was evaporated. The residue (0.7 g) was purified by column chromatography over kromasil (eluent: CH$_2$Cl$_2$/CH$_3$OH 99/1; 10 µm). The pure fractions were collected and the solvent was evaporated. The residue (0.155 g) was purified by column chromatography over C18 (eluent: CH$_3$CN/NH$_4$Ac 0.5% 60/40). The pure fractions were collected and the solvent was evaporated. The residue (0.051 g) was crystallized from DIPE. The precipitate was filtered off and dried. Yield: 0.029 g of compound 107 (9%). (mp. 250° C.)

b) The Preparation of Compound 108 and 109 compound 108

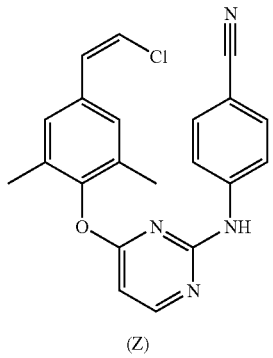

(Z)

compound 109

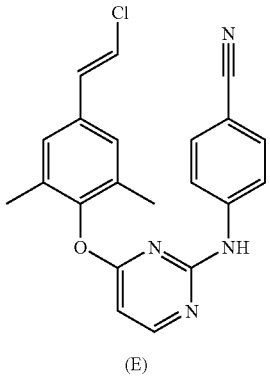

(E)

nBuLi[1.6] (0.00261 mol) was added dropwise at −70° C. to a mixture of (chloromethyl)triphenylphosphonium chloride (0.00261 mol) in THF (10 ml) under N$_2$ flow. The mixture was stirred for 30 minutes. A solution of intermediate 31 (prepared according to A4.a) (0.00087 mol) in THF (5 ml) was added dropwise. The mixture was stirred at room temperature overnight, then poured out into H$_2$O and extracted with EtOAc. The organic layer was separated, dried (MgSO$_4$), filtered, and the solvent was evaporated. The residue (1.1 g) was purified by column chromatography over silica gel (eluent: CH$_2$Cl$_2$/CH$_3$OH/NH$_4$OH 98/2/0.1; 15-40 µm). The pure fractions were collected and the solvent was evaporated. The residue (0.3 g) was purified by column chromatography over hypersil C18 (eluent: CH$_3$OH/NH$_4$Ac 0.5% 70/30). Two fractions (F1, F2) were collected and the solvent was evaporated. Yield: 0.097 g F1 and 0.085 g F2. F1 was crystallized from DIPE. The precipitate was filtered off and dried. Yield: 0.045 g of compound 108 (14%) (mp. 165° C.). F2 was crystallized from DIPE. The precipitate was filtered off and dried. Yield: 0.049 g of compound 109 (15%) (mp. 200° C.).

c) The Preparation of Compound 110

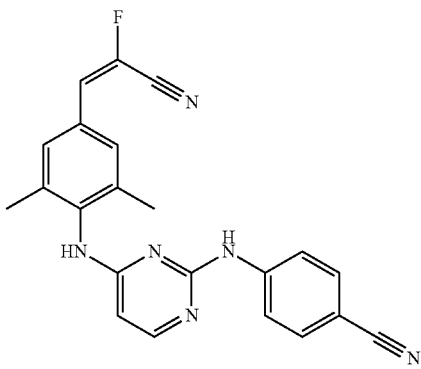

(E)

nBuLi[1.6] (1.1 ml, 0.0017 mol) was added dropwise at −70° C. to a mixture of 1,1,1,3,3,3-hexamethyldisilazane (HN(TMS)$_2$)(0.0017 mol) in THF (6 ml). The mixture was stirred at −70° C. for 30 minutes. Cyanofluoromethyl (0.0017 mol) was added. The mixture was stirred for 30 minutes. Phosphorochloridic acid diethyl ester (0.0017 mol) was added. The mixture was stirred at −70° C. for 15 minutes. nBuLi[1.6] (1.1 ml, 0.0017 mol) was added dropwise. The mixture was stirred for 30 minutes. A solution of intermediate 31 (prepared according to A4.a) (0.0008 mol) in THF (4 ml) was added. The mixture was stirred at room temperature overnight, poured out into H$_2$O and extracted with CH$_2$Cl$_2$. The organic layer was separated, dried (MgSO$_4$), filtered, and the solvent was evaporated. The residue (0.5 g) was purified by column chromatography over silica gel (eluent: CH$_2$Cl$_2$/EtOAc 95/5; 15-40 μm). Four fractions (F1, F2, F3, F4) were collected and the solvent was evaporated. Yield: 0.026 g of compound 110 (8%) (mp. 254° C.).

d) The Preparation of Compound 111

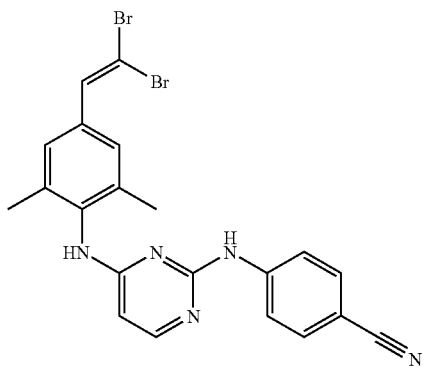 [SMILES: Cc1cc(C=C(Br)Br)cc(C)c1Nc1ccnc(Nc2ccc(C#N)cc2)n1]

A solution of (CuCl)$_2$ (0.00015 mol) in NH$_3$ aqueous (500 μl) was added to a mixture of intermediate 21 (prepared according to A5.b) (0.0014 mol) in DMSO (1 ml). A solution of CBr$_4$ (0.0044 mol) in DMSO (1.5 ml) was added at 0° C. The mixture was stirred at room temperature overnight, poured out on ice and filtered. The organic layer was washed with CH$_2$Cl$_2$, dried (MgSO$_4$), filtered and the solvent was evaporated. The residue (2.73 g) was purified by column chromatography over silica gel (eluent: CH$_2$Cl$_2$/CH$_3$OH 100/0 to 99/1; 15-40 μm). Two fractions were collected and the solvent was evaporated. Yield: 0.007 g of fraction 1 and 0.11 g of fraction 2. Fraction 2 was crystallized from DIPE. The precipitate was filtered off and dried. Yield: 0.075 g of compound 111 (mp. 223° C.).

Example B9B a) The Preparation of Compound 112

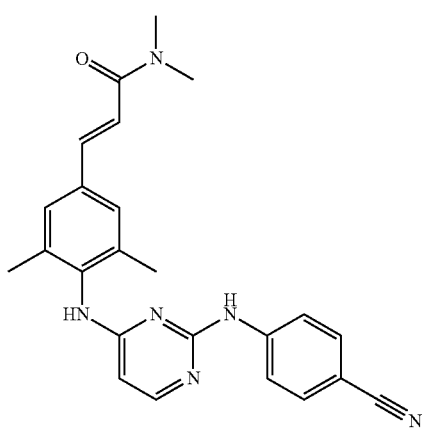

A mixture of intermediate 23 (0.0005 mol), 1-hydroxybenzotriazole (0.0007 mol) and EDCI (0.0007 mol) in CH$_2$Cl$_2$ (10 ml) and THF (2 ml) was stirred. A solution of NH(CH$_3$)$_2$.HCl (0.0006 mol) and Et$_3$N (0.0005 mol) was added. The mixture was stirred at room temperature for 12 hours. H$_2$O was added. The mixture was extracted with CH$_2$Cl$_2$. The organic layer was separated, dried (MgSO$_4$), filtered, and the solvent was evaporated. The residue was purified by column chromatography over kromasil (eluent: CH$_2$Cl$_2$/CH$_3$OH 100/0 to 90/10; 5 μm). The pure fractions were collected and the solvent was evaporated. Yield: 0.124 g (58%). This fraction was purified by column chromatography over kromasil (eluent: CH$_2$Cl$_2$/CH$_3$OH 99/1; 5 μm). The pure fractions were collected and the solvent was evaporated. Yield: 0.045 g of compound 112 (21%) (mp.>264° C.).

b) The Preparation of Compound 113

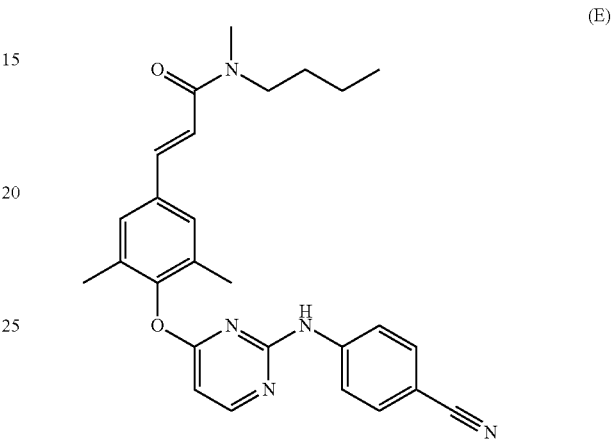

A mixture of intermediate 57 (prepared according to A7.b) (0.0002 mol), 1-hydroxybenzotriazole (0.0003 mol) and EDCI (0.0003 mol) in CH$_2$Cl$_2$ (10 ml) was stirred. N-methyl-1-butanamine [CAS 110-68-9] (0.0002 mol) was added. The mixture was stirred at room temperature for 12 hours. H$_2$O was added. The mixture was extracted with CH$_2$Cl$_2$. The organic layer was separated, dried (MgSO$_4$), filtered, and the solvent was evaporated. Yield: 0.149 g. This fraction was purified by column chromatography over kromasil (eluent: CH$_2$Cl$_2$/CH$_3$OH 100/0 to 90/10; 5 μm). The pure fractions were collected and the solvent was evaporated. Yield: 0.065 g. This fraction was taken up in DIPE. The precipitate was filtered off and dried. Yield: 0.035 g of compound 113 (30%) (mp. 212° C.).

c) The Preparation of Compound 114

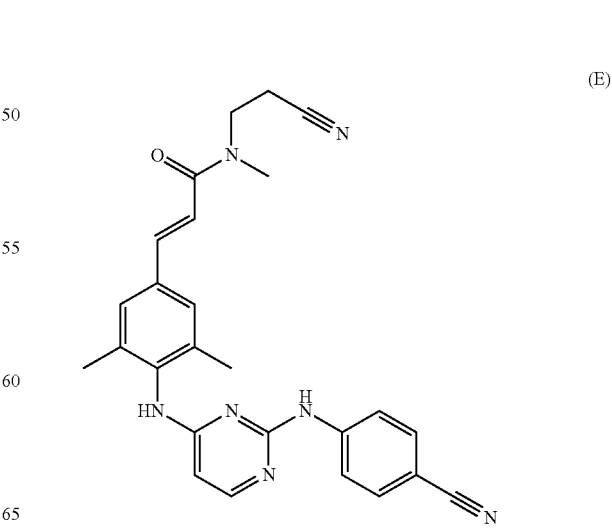

A mixture of intermediate 23 (prepared according A7.a) (0.0005 mol), 1-hydroxybenzotriazole (0.0007 mol) and EDCI (0.0007 mol) in CH$_2$Cl$_2$ (10 ml) and THF (2 ml) was stirred. 3-(methylamino)propanenitrile (0.0006 mol) was added. The mixture was stirred at room temperature for 12 hours. H$_2$O was added. The mixture was extracted with CH$_2$Cl$_2$. The organic layer was separated, dried (MgSO$_4$), filtered, and the solvent was evaporated. The residue was purified by column chromatography over kromasil (eluent: CH$_2$Cl$_2$/CH$_3$OH 100/0 to 90/10; 5 μm). The pure fractions were collected and the solvent was evaporated. Yield: 0.068 g. This fraction was crystallized from DIPE. The precipitate was filtered off and dried. Yield: 0.032 g of compound 114 (14%) (mp. 168° C.).

d) The Preparation of Compound 115

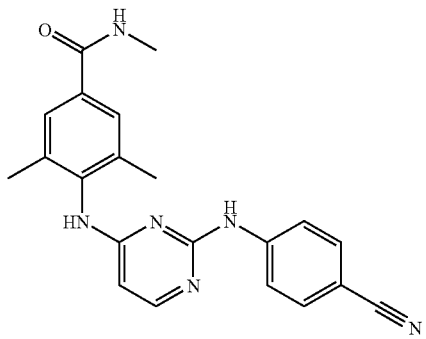 [SMILES: CNC(=O)c1cc(C)c(Nc2ccnc(Nc3ccc(C#N)cc3)n2)c(C)c1]

A mixture of

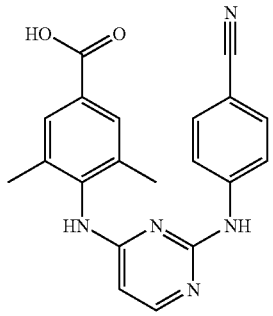 [SMILES: Cc1cc(C(=O)O)cc(C)c1Nc1ccnc(Nc2ccc(C#N)cc2)n1]

(0.000195 mol) and methylamine (2 equiv, 0.000390 mol) in THF (5 ml) and Et$_3$N (0.054 ml) was stirred at room temperature. EDCI (2 equiv, 0.000390 mol) and 1-hydroxy-benzotriazole (2 equiv, 0.000390 mol) were added. The reaction mixture was stirred at room temperature for 12 hours and taken up into H$_2$O. The organic layer was separated, dried, filtered and the solvent evaporated. The product was isolated and purified by column chromatography. Yield: 0.026 g of compound 115 (17.92%).

Example B9C

The Preparation of Compound 116

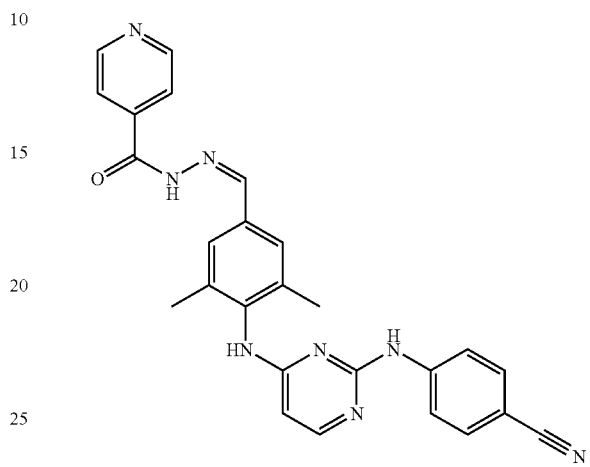

A mixture of intermediate 13 (prepared according to A5.a) (0.000291 mol) and isonicotinic acid hydrazide (2.5 equiv., 0.000728 mol) in ethanol (1 ml) and CH$_2$Cl$_2$ (2 ml) was stirred and refluxed for 12 hours. The solvent was evaporated till dryness. The residue was purified by chromatography. Yield: 0.033 g of compound 116 (24.50%).

Example B9D a) The Preparation of Compound 117

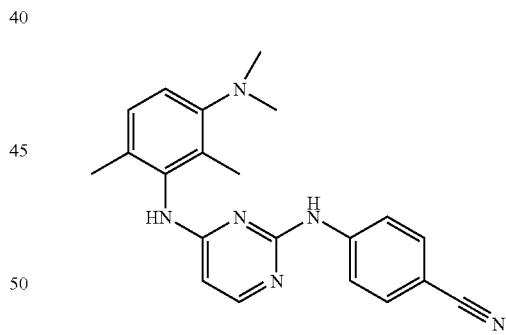

Sodium cyanoborohydride (0.0024 mol) was added at room temperature to a solution of intermediate 26 (prepared according to A9) (0.0008 mol) in formaldehyde (0.5 ml) and CH$_3$CN (20 ml) under N$_2$ flow. Acetic acid (0.5 ml) was added. The mixture was stirred at room temperature for 2 hours, poured out into H$_2$O/K$_2$CO$_3$ 10% and extracted with CH$_2$Cl$_2$. The organic layer was separated, dried (MgSO$_4$), filtered, and the solvent was evaporated. The residue (0.3 g) was purified by column chromatography over hypersol (eluent: CH$_2$Cl$_2$/CH$_3$OH 97/3; 5 μm). The pure fractions were collected and the solvent was evaporated. Yield: 0.08 g (28%). This fraction was crystallized from 2-propanone/diethyl ether. The precipitate was filtered off and dried. Yield: 0.012 g of compound 117 (5%) (mp. 132° C.).

85 b) The Preparation of Compound 118

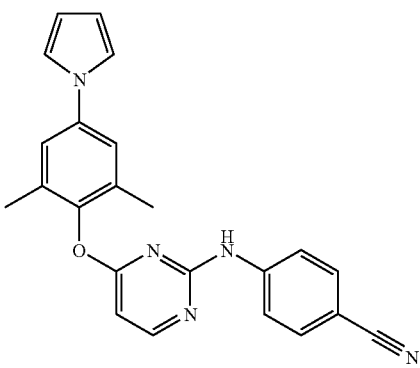 [SMILES: Cc1cc(-n2cccc2)cc(C)c1Oc1ccnc(Nc2ccc(C#N)cc2)n1]

A mixture of

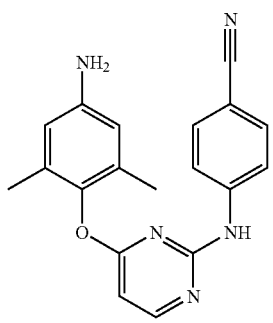 [SMILES: Cc1cc(N)cc(C)c1Oc1ccnc(Nc2ccc(C#N)cc2)n1]

(prepared according to A9) (0.0015 mol) and tetrahydro-2,5-dimethoxyfuran (0.0077 mol) in acetic acid (10 ml) was stirred and refluxed for 1 hour, then poured out into ice water and $K_2CO_3$ and extracted with $CH_2Cl_2$. The organic layer was separated, dried ($MgSO_4$), filtered, and the solvent was evaporated. The residue (1 g) was purified by column chromatography over silica gel (eluent: cyclohexane/EtOAc 95/5; 15-40 μm). The pure fractions were collected and the solvent was evaporated. Yield: 0.23 g. This fraction was crystallized from DIPE/diethyl ether. The precipitate was filtered off and dried. Yield: 0.075 g. This fraction was crystallized again from DIPE/diethyl ether. The precipitate was filtered off and dried. Yield: 0.027 g of compound 118 (5%).

Example B9E a) The Preparation of Compound 119

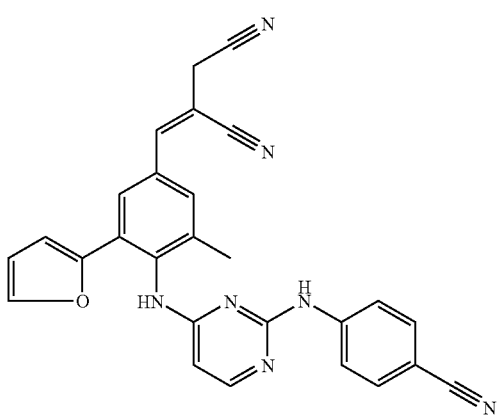 [SMILES: Cc1cc(/C=C(\C#N)CC#N)cc(-c2ccco2)c1Nc1ccnc(Nc2ccc(C#N)cc2)n1]

86

Tributylphosphine (0.0015 mol) was added to a mixture of but-2-enedinitrile (0.0015 mol) in THF (8 ml). The mixture was stirred and refluxed for 2 hours.

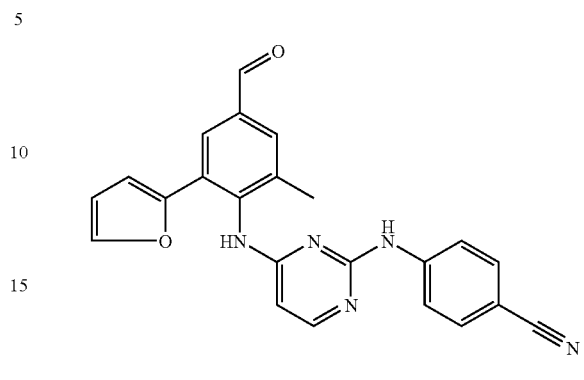

prepared according to A5.a) (0.0005 mol) was added. The mixture was stirred and refluxed overnight. $H_2O$ was added. The mixture was extracted with $CH_2Cl_2$. The organic layer was separated, dried ($MgSO_4$), filtered and the solvent was evaporated. The residue (0.618 g) was purified by column chromatography over kromasil (eluent: $CH_2Cl_2$ 100; 10 □m). Two fractions were collected and the solvent was evaporated. Yield: 0.03 g of compound 119 (13%).

b) The Preparation of Compound 120

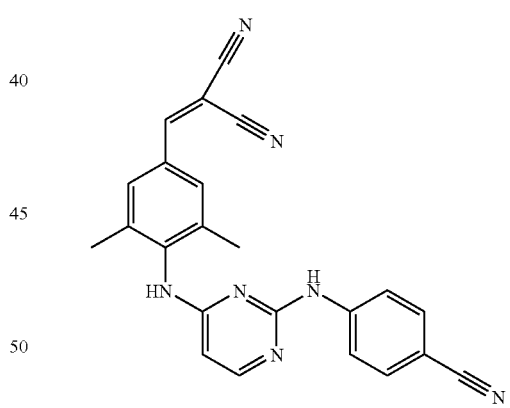

Intermediate 13 (prepared according to A5.a) (0.002 mol) was added to a mixture of propanedinitrile (0.004 mol) and piperidine (0.004 mol) in ethanol (10 ml). The mixture was stirred at room temperature for 5 minutes. The solvent was evaporated. The residue was taken up in $CH_2Cl_2$ and purified by column chromatography over silica-gel (eluent: $CH_2Cl_2$/$CH_3OH$ 98/2; 15-40 μm). The pure fractions were collected and the solvent was evaporated. Yield: 0.6 g of compound 120.

Example B9F

The Preparation of Compound 122

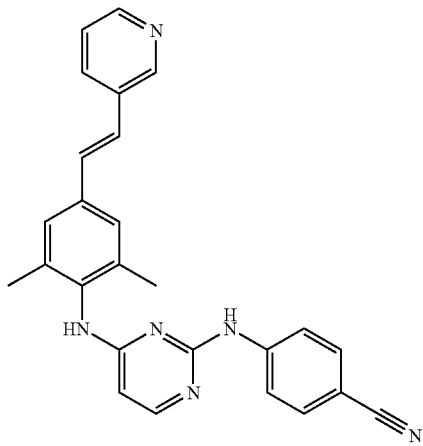 [SMILES: Cc1cc(/C=C/c2cccnc2)cc(C)c1Nc1ccnc(Nc2ccc(C#N)cc2)n1]

nBuLi [1.6 M] (0.0016 mol) was added dropwise at −78° C. to a mixture of intermediate 27 (prepared according to A10) (0.0004 mol) in THF (10 ml) under N₂ flow. The mixture was stirred at −78° C. for 1 hour, then brought to room temperature, stirred for 30 minutes and cooled to −78° C. A solution of 2-pyridinecarboxaldehyde (0.0004 mol) in THF (10 ml) was added. The mixture was stirred at room temperature for 2 hours, poured out on ice and extracted with EtOAc. The organic layer was separated, dried (MgSO₄), filtered, and the solvent was evaporated. The residue (0.32 g) was purified by column chromatography over silica gel (eluent: CH₂Cl₂/CH₃OH/NH₄OH 98/2/0.1; 10 μm). Two fractions were collected and the solvent was evaporated. Yield: 0.021 g of compound 122 (10.4%) (mp. 120° C.).

Example B10

The Preparation of Compound 20

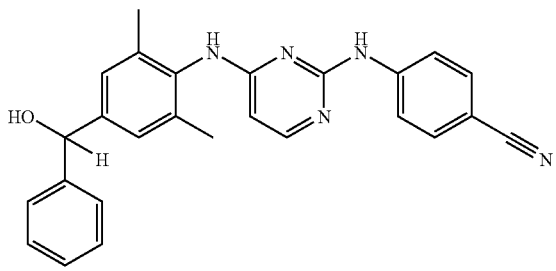 [SMILES: Cc1cc(C(O)c2ccccc2)cc(C)c1Nc1ccnc(Nc2ccc(C#N)cc2)n1]

NaBH₄ (0.0015 mol) was added portionwise at 5° C. to a mixture of compound 19 (see table 3) (prepared according to B1) (0.0014 mol) in CH₃OH (15 ml) under N₂ flow. The mixture was stirred at 5° C. for 1 hour, poured out into H₂O and extracted with CH₂Cl₂. The organic layer was separated, dried (MgSO₄), filtered, and the solvent was evaporated. The residue (0.15 g) was purified by column chromatography over silica gel (eluent: CH₂Cl₂/CH₃OH 99/1; 10 μm). The pure fractions were collected and the solvent was evaporated. The residue (0.068 g, 12%) was crystallized from DIPE. The precipitate was filtered off and dried. Yield: 0.032 g of compound 20.

Example B11

The Preparation of Compound 21

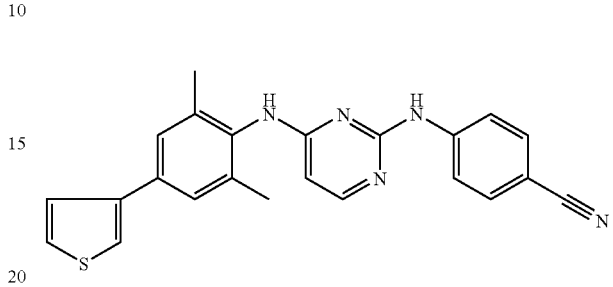

A mixture of compound 2 (see table 3) (0.0002 mol), 3-thienylboronic acid (0.0005 mol), Pd(PPh₃)₄ (0.00002 mol) and Na₂CO₃ (0.0007 mol) in DME (3 ml) was stirred and refluxed in a scelled tube for 3 hours. H₂O was added. The mixture was extracted with ethyl acetate. The organic layer was separated, dried (MgSO₄), filtered, and the solvent was evaporated. The residue was purified by column chromatography over silica gel (eluent: CH₂Cl₂/CH₃OH 98/2; 15-40 μm). The pure fractions were collected and the solvent was evaporated. Yield: 0.04 g of compound 21 (40%).

Example B12

The Preparation of Compound 23

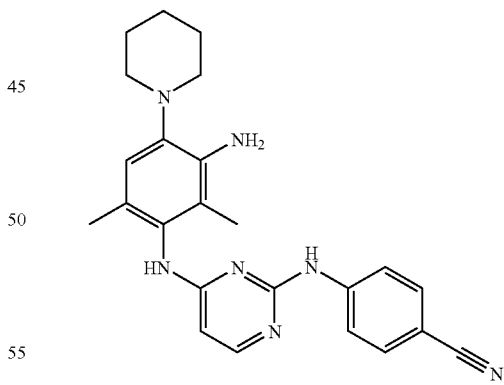

A mixture of compound 22 (see table 3) (prepared according to B4.a) (0.0002 mol) and Raney Nickel (0.1 g) in CH₃OH (10 ml) was stirred at room temperature for 15 minutes under a 2 bar pression of H₂, then filtered over celite. Celite was washed with CH₃OH. The filtrate was evaporated. Yield: 0.48 g. This fraction was purified by column chromatography over kromasyl (eluent: CH₂Cl₂/CH₃OH 99/1; 15-40 μm). Two fractions (F1, F2) were collected and the solvent was evaporated. Yield: 0.13 g F1 and 0.13 g F2. F2 was crystallized from diethyl ether. The precipitate was filtered off and dried. Yield: 0.09 g of compound 23 (20%).

Example B13

The Preparation of Compound 24

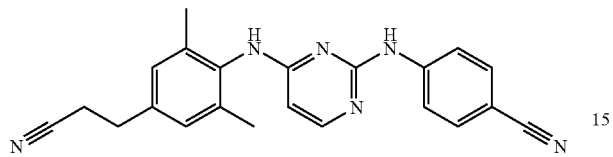

A mixture of compound 1 (0.0004 mol) and Pd/C (0.07 g) in CH$_3$OH (10 ml) was hydrogenated at room temperature for 5 hours under a 3 bar pressure of H$_2$, then filtered over celite, washed with CH$_2$Cl$_2$ and the solvent was evaporated till dryness. The residue was crystallized from DIPE. The precipitate was filtered off and dried. The residue (0.7 g) was purified by column chromatography over kromasyl (eluent: CH$_2$Cl$_2$/CH$_3$OH 100/0 to 99/1; 5 μm). The pure fractions were collected and the solvent was evaporated. The residue (0.06 g) was crystallized from DIPE. The precipitate was filtered off and dried. Yield: 0.04 g of compound 24 (27%).

Example B14

The Preparation of Compound 26

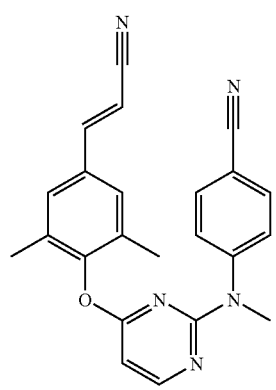 [SMILES: Cc1cc(/C=C/C#N)cc(C)c1Oc1ccnc(N(C)c2ccc(C#N)cc2)n1]

NaH 60% (0.0004 mol) was added at room temperature to a mixture of compound 25 (see Table 4) (prepared according to B6.c) (0.0004 mol) in THF (30 ml). The mixture was stirred at room temperature for 1 hour. A solution of ICH$_3$ (0.0004 mol) in THF (30 ml) was added. The mixture was stirred at 60° C. for 2 hours, then cooled, poured out into H$_2$O and extracted with CH$_2$Cl$_2$. The organic layer was separated, dried (MgSO$_4$), and the solvent was evaporated. The residue (0.12 g) was purified by column chromatography over kromasil (eluent: CH$_2$Cl$_2$/CH$_3$OH 99/1; 10 μm). The pure fractions were collected and the solvent was evaporated. Yield: 0.049 g of compound 26 (32%).

Example B15 a) The Preparation of Compound 123

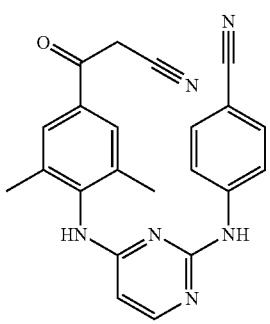 [SMILES: Cc1cc(C(=O)CC#N)cc(C)c1Nc1ccnc(Nc2ccc(C#N)cc2)n1]

Jones's reagent (0.0056 mol) was added at 5° C. to a mixture of compound 18 (prepared according to B9) (0.0029 mol) in 2-propanone (20 ml) under N$_2$ flow. The mixture was stirred at 5° C. for 2 hours, then poured out into H$_2$O, basified with NaHCO$_3$ and extracted with CH$_2$Cl$_2$. The organic layer was separated, dried (MgSO$_4$), filtered, and the solvent was evaporated. The residue (1.5 g) was purified by column chromatography over silica gel (eluent: CH$_2$Cl$_2$/CH$_3$OH/NH$_4$OH 98/2/0.1; 15-40 μm).

Two fractions (F1, F2) were collected and the solvent was evaporated. Yield: 0.122 g F1 (11%) and 0.19 g F2 (17%). F2 was crystallized from DIPE. The precipitate was filtered off and dried. Yield: 0.034 g of compound 123 (mp. 150° C.).

b) The Preparation of Compound 124

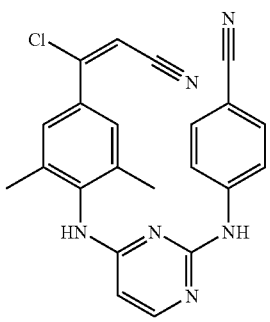 [SMILES: Cc1cc(/C(Cl)=C\C#N)cc(C)c1Nc1ccnc(Nc2ccc(C#N)cc2)n1]

A mixture of compound 123 (0.0005 mol) in POCl$_3$ (1.5 ml) was stirred at 80° C. for 24 hours, poured out into ice and K$_2$CO$_3$ 10% and extracted with CH$_2$Cl$_2$/CH$_3$OH. The organic layer was separated, dried (MgSO$_4$), filtered and the solvent was evaporated. The residue (0.14 g) was purified by column chromatography over kromasil (eluent: CH$_2$Cl$_2$/CH$_3$OH 99/1; 10 μm). The pure fractions were collected and the solvent was evaporated. Yield: 0.026 g of compound 124.

Example B16 a) The Preparation of Compound 125

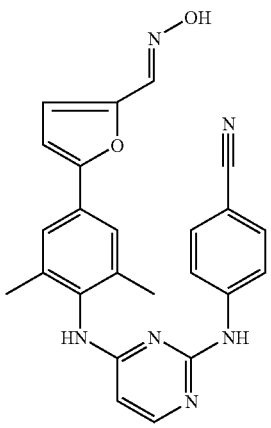 [SMILES: Cc1cc(-c2ccc(/C=N/O)o2)cc(C)c1Nc1ccnc(Nc2ccc(C#N)cc2)n1]

NaOH 5N (2 ml) was added dropwise at 50° C. to a mixture of compound 104 (see Table 3) (prepared according to B2.c) (0.0003 mol) and NH$_2$OH, HCl (0.0004 mol) in ethanol (10 ml). The mixture was stirred at 50° C. for 2 hours. Two-third of the mixture was evaporated. The mixture was poured out into H$_2$O and extracted with CH$_2$Cl$_2$. The organic layer was washed with K$_2$CO$_3$ 10%, dried (MgSO$_4$), filtered, and the solvent was evaporated. Yield: 0.21 g of compound 125.

b) The Preparation of Compound 126

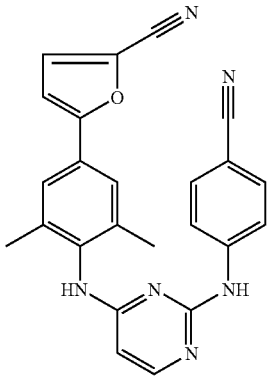 [SMILES: Cc1cc(-c2ccc(C#N)o2)cc(C)c1Nc1ccnc(Nc2ccc(C#N)cc2)n1]

1,1'-carbonyldiimidazole (0.0012 mol) was added to a mixture of compound 125 (0.0003 mol) in THF (20 ml). The mixture was stirred and refluxed overnight, poured out into H$_2$O and extracted with CH$_2$Cl$_2$. The organic layer was separated, dried (MgSO$_4$), filtered, and the solvent was evaporated. The residue (0.17 g) was purified by column chromatography over kromasil (eluent: CH$_2$Cl$_2$/CH$_3$OH 98/2; 10 μm). Two fractions were collected and the solvent was evaporated. Yield: 0.035 g of fraction 1 and 0.05 g of fraction 2. Both fractions were mixed and crystallized from diethyl ether. The precipitate was filtered off and dried. Yield: 0.05 g of compound 126 (38%) (mp.>260° C.).

Example B17

Preparation of Compound 253

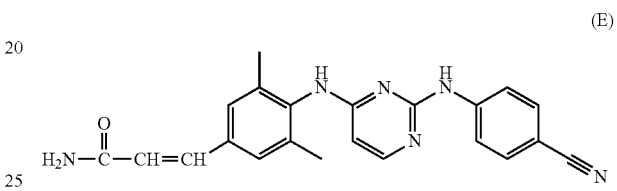

(E)

a) 2.53 ml of acetonitrile, 0.056 g (0.253 mmol) of Pd(OAc)$_2$ and 0.154 g (0.506 mmol) of tris(2-methylphenyl) phosphine were brought in a 100 ml flask under nitrogen and the mixture was stirred for 10 minutes. To the mixture was added 1 g (2.53 mmol) of intermediate 58, 0.51 ml (3.8 mmol) of N,N-diethylethanamine and 0.36 g (5.06 mmol) of acrylamide. The mixture was heated at reflux (80° C.) for 5 days yielding 28% of compound 253.

b) In a 100 ml flask under N$_2$ were introduced 0.8 g (4.33 mmol; 1 eq.) of intermediate 3a (E), 1 g (4.33 mmom; 1 eq.) of intermediate 5 and 16 ml of 2-propanol. To this mixture 0.72 ml of HCl 6N in 2-propanol were added. The mixture was stirred under refluxed for 72 hours and then cooled yielding the hydrochloric acid salt of compound 253, i.e. compound 254.

Compound 254 can be converted into the free base according to art-known methodologies (see also Example B1A).

Compound 253 can be converted into compound 1 according to the method described above in Example A1c)y).

The following Tables 3, 4 and 5 list compounds of formula (I) as prepared according to one of the above examples (Ex. No.).

TABLE 3

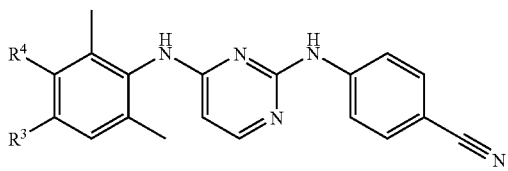

| Comp No. | Ex. No. | R$^3$ | R$^4$ | Physical data m.p. ° C. (MH+)* |
|---|---|---|---|---|
| 2 | B2a | 2-benzofuranyl | H | mp. > 240 |
| 21 | B11 | 3-thienyl | H | mp. 220 |
| 3 | B2b | 2-furanyl | H | mp. 228 |

TABLE 3-continued

| Comp No. | Ex. No. | R³ | R⁴ | Physical data m.p. °C. (MH+)* |
|---|---|---|---|---|
| 28 | B2a | 2-thienyl | H | mp. 235 |
| 29 | B2a | phenyl | H | mp. 230 |
| 1 | B1/B6a | —CH=CH—CN | H | mp. 245, (E) |
| 30 | B2a | 2,4-dichlorophenyl | H | (460) |
| 31 | B2a | 2-benzo[b]thienyl | H | (448) |
| 32 | B2a | 1-naphthalenyl | H | (442) |
| 33 | B2a | 3-chlorophenyl | H | (426) |
| 34 | B2a | 3-acetylphenyl | H | (434) |
| 35 | B2a | 3-methylphenyl | H | (406) |
| 36 | B2a | 2-naphthalenyl | H | (442) |
| 37 | B2a | 4-chlorophenyl | H | (426) |
| 38 | B2a | 4-methoxyphenyl | H | (422) |
| 39 | B2a | 4-methylthiophenyl | H | (438) |
| 40 | B2a | 4-(CH₂OH)phenyl | H | |
| 19 | B1 | benzoyl (PhC(=O)—) | H | mp. 220 |
| 8 | B5a | —C(=N—OH)—CH(CH₃)₂ | H | mp. 156 |
| 20 | B10 | α-hydroxybenzyl (PhCH(OH)—) | H | mp. 205 |
| 27 | B1 | phenylacetyl (PhCH₂C(=O)—) | H | mp. 193 |
| 41 | B10 | PhCH₂CH(OH)— | H | mp. 200 |
| 42 | B5a | PhCH₂C(=N—OH)— | H | mp. 155 |
| 43 | B4b | piperidinylmethyl | H | mp. 110 |
| 44 | B5b | PhCH₂C(=N—OCH₃)— | H | mp. 110 |
| 45 | B5a | —C(=N—OH)—CH₃ | H | mp. 135 |
| 9 | B5b | —C(=N—O—CH₃)—CH(CH₃)₂ | H | mp. 185 |

TABLE 3-continued
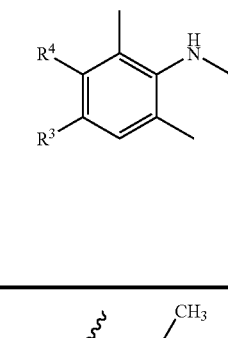
| Comp No. | Ex. No. | R³ | R⁴ | Physical data m.p. ° C. (MH+)* |
|---|---|---|---|---|
| 46 | B5b | 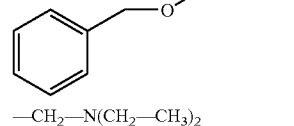 | H | mp. 164 |
| 47 | B4b | —CH₂—N(CH₂—CH₃)₂ | H | mp. 150 |
| 48 | B4b | 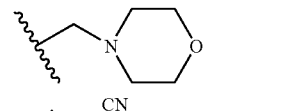 | H | mp. 85 |
| 15 | B6e | 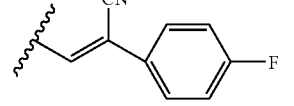 | H | (461) |
| 49 | B6e | 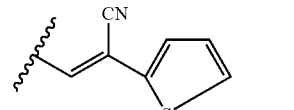 | H | (449) |
| 50 | B6e | 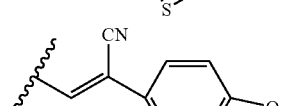 | H | (487) |
| 51 | B6e | 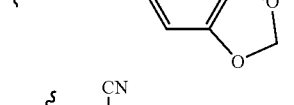 | H | (493) |
| 52 | B6e | 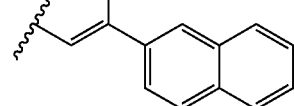 | H | (473) |
| 53 | B6e | 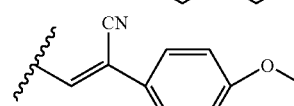 | H | (443) |
| 54 | B6e | 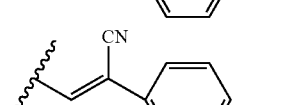 | H | (446) |
| 55 | B6e | 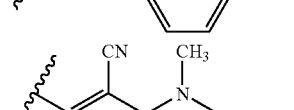 | H | (449) |

TABLE 3-continued

| Comp No. | Ex. No. | R³ | R⁴ | Physical data m.p. °C. (MH+)* |
|---|---|---|---|---|
| 56 | B6e | (1-cyano-2-(4-bromophenyl)vinyl) | H | (521) |
| 57 | B6e | (1-cyano-2-(3-methylphenyl)vinyl) | H | (457) |
| 6 | B4b | —CH₂—N(CH₃)—CH₂—CH₂—N(CH₃)₂ | H | (430) |
| 58 | B4b | —CH₂—N(benzyl)—CH₂—CH₂—N(CH₃)₂ | H | (506) |
| 59 | B4b | —CH₂-(4-methylpiperazin-1-yl) | H | (428) |
| 60 | B4b | —CH₂-(4-(4-acetylphenyl)piperazin-1-yl) | H | (532) |
| 61 | B4b | —CH₂-(4-benzylpiperazin-1-yl) | H | (504) |
| 62 | B4b | —CH₂-(4-benzylpiperidin-1-yl) | H | (503) |
| 63 | B4b | —CH₂-(5-phenylimidazol-1-yl) | H | (472) |
| 64 | B4b | —CH₂-(4-(pyridin-2-yl)piperazin-1-yl) | H | (491) |
| 65 | B4b | —CH₂—N(CH₃)—CH₂—CH₂—CH₂—CH₃ | H | (415) |
| 66 | B4b | —CH₂-(4-methyl-1,4-diazepan-1-yl) | H | (442) |
| 67 | B4b | —CH₂-(5-methylimidazol-1-yl) | H | (410) |
| 68 | B4b | —CH₂—N(CH₃)—CH₂—CH₂—CH₃ | H | (401) |

TABLE 3-continued

| Comp No. | Ex. No. | R³ | R⁴ | Physical data m.p. ° C. (MH+)* |
|---|---|---|---|---|
| 69 | B4b | -CH₂-pyrrolidin-1-yl | H | (399) |
| 70 | B4b | -CH₂-imidazol-1-yl | H | (396) |
| 71 | B4b | —CH₂—N(CH₂—CH₂—O—CH₃)₂ | H | (461) |
| 72 | B4b | -CH₂-(3-ethoxycarbonyl-piperidin-1-yl) | H | (485) |
| 73 | B4b | -CH₂-N(CH₃)-(1-methyl-piperidin-4-yl) | H | (456) |
| 74 | B4b | -CH₂-(4-(pyrimidin-2-yl)-piperazin-1-yl) | H | (492) |
| 75 | B4b | —CH₂—N(CH₃)—CH₂—CH₂—CN | H | (412) |
| 76 | B4b | -CH₂-(2,6-dimethyl-morpholin-4-yl) | H | (443) |
| 77 | B4b | -CH₂-(2,5-dihydro-pyrrol-1-yl) | H | (397) |
| 78 | B4b | -CH₂-thiazolidin-3-yl | H | (417) |
| 79 | B4b | -CH₂-N(ethyl)(pyridin-4-ylmethyl) | H | (464) |
| 80 | B4b | —CH₂—NH—CH₂—CH₂—N(CH₂—CH₃)₂ | H | mp, 105 |
| 81 | B1 | -C(=O)-furan-2-yl | H | mp. 240 |
| 82 | B10 | -CH(OH)-furan-2-yl | H | mp. 170 |
| 24 | B13 | —CH₂—CH₂—CN | H | mp. 208 |

TABLE 3-continued

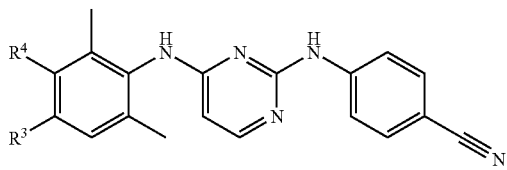

| Comp No. | Ex. No. | R³ | R⁴ | Physical data m.p. °C. (MH+)* |
|---|---|---|---|---|
| 83 | B8 | (5-phenyl-1,2,4-oxadiazol-3-yl)methyl | H | mp. > 250° C. |
| 14 | B6d | 2-(furan-2-yl)-2-cyanoethenyl | H | mp. 158 |
| 84 | B6c | —C(CH₃)=CH—CN | H | mp. 224° C. (E) |
| 18 | B9 | —CH(OH)—CH₂—CN | H | mp. 252° C. |
| 85 | B4b | (2-bromoimidazol-1-yl)methyl | H | (474) |
| 86 | B4b | (3-phenyl-1,2,4-triazol-1-yl)methyl | H | (473) |
| 87 | B4b | (5-hydroxymethylimidazol-1-yl)methyl | H | (426) |
| 88 | B4b | (2-methylimidazol-1-yl)methyl | H | (424) |
| 89 | B4b | (4,5-dicyanoimidazol-1-yl)methyl | H | (446) |
| 90 | B4b | (1,2,3-triazol-1-yl)methyl | H | (397) |
| 91 | B4b | (2-isopropylimidazol-1-yl)methyl | H | (438) |

TABLE 3-continued

[Structure: R⁴ and R³ on a 2,6-dimethylphenyl group linked via NH to a pyrimidine, which is linked via NH to a 4-cyanophenyl group]

| Comp No. | Ex. No. | R³ | R⁴ | Physical data m.p. °C. (MH+)* |
|---|---|---|---|---|
| 92 | B4b | [1-methylene-2-propyl-imidazol-1-yl] | H | (438) |
| 93 | B4b | [1-methylene-2-methyl-imidazol-1-yl] | H | (410) |
| 94 | B4b | [1-methylene-3-methyl-pyrazol-1-yl] | H | (410) |
| 95 | B4b | [1-methylene-2-methyl-4,5-dichloro-imidazol-1-yl] | H | (478) |
| 96 | B4b | [1-methylene-2-(pyridin-3-yl)-imidazol-1-yl] | H | (473) |
| 103 | B6b | —CH=C(CH₃)—CN | H | mp. 201° C. (E) |
| 11 | B6b | —CH=C(CH₃)—CN | H | mp. 246° C. (Z) |
| 10 | B6a | —CH=CH—CN | H | mp. 258° C. (Z) |
| 4 | B3 | —CH₂—CN | H | mp. 110° C. |
| 17 | B8 | [5-(1,2,4-oxadiazol-3-yl)methyl-N,N-dimethylamine] | H | mp. 110° C. |
| 97 | B8 | [5-(3-ethyl-1,2,4-oxadiazol-5-yl)] | H | mp. 240° C. |
| 16 | B7 | [5-(2-thiol-1,3,4-oxadiazol-5-yl)] | H | mp. > 250° C. |
| 7 | B4c | —CH₂—O—CH₂—CH₂—CN | H | mp > 260 |
| 5 | B4a | 4-thiomorpholinyl | —NO₂ | mp. 268 |
| 98 | B4a | 4-morpholinyl | —NO₂ | mp. 210 |
| 22 | B4a | 1-piperidinyl | —NO₂ | mp. 252 |
| 23 | B12 | 1-piperidinyl | —NH₂ | mp. 262 |
| 12 | B6c | H | —C(CH₃)=CH—CN | (E) (381) |
| 13 | B6c | H | —C(CH₃)=CH—CN | (Z) (381) |
| 127 | B1 | —N(CH₃)₂ | H | mp. 228° C. |
| 123 | B15a | —C(=O)—CH₂—CN | H | mp. 150° C. |

TABLE 3-continued

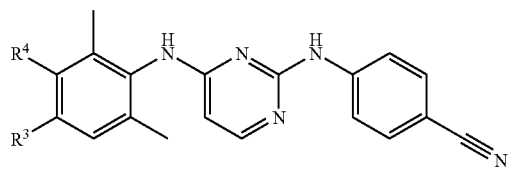

| Comp No. | Ex. No. | $R^3$ | $R^4$ | Physical data m.p. ° C. (MH+)* |
|---|---|---|---|---|
| 116 | B9C | [pyridine-4-carbohydrazone] | H | (463) |
| 128 | B9C | [3-fluorobenzohydrazone] | H | (480) |
| 129 | B9C | [furan-2-carbohydrazone] | H | (452) |
| 130 | B9C | —CH=N—NH—C(=O)—CH$_3$ | H | (400) |
| 131 | B9C | —CH=N—NH—C(=O)—CH$_2$—CN | H | |
| 132 | B9C | [thiophene-2-carbohydrazone] | H | (468) |
| 115 | B9Bd | —C(=O)—NH—CH$_3$ | H | (373) |
| 134 | B9Bd | —C(=O)—N(CH$_3$)$_2$ | H | (387) |
| 135 | B9Bd | —C(=O)—N(CH$_3$)—CH$_2$—CH$_3$ | H | (401) |
| 136 | B9Bd | —C(=O)—N(CH$_2$—CH$_3$)$_2$ | H | (415) |
| 137 | B9Bd | —C(=O)—NH—CH$_2$—CH$_3$ | H | (387) |
| 138 | B9Bd | —C(=O)—NH—CH$_2$—CN | H | (398) |
| 139 | B9Bd | —C(=O)—N(CH$_3$)—CH$_2$—CN | H | (412) |
| 140 | B9Bd | —C(=O)—NH—CH$_2$—C≡CH | H | (397) |
| 141 | B9Bd | —C(=O)—NH—CH$_2$—CH=CH$_2$ | H | (399) |
| 142 | B9Bd | —C(=O)—NH—CH(CH$_3$)$_2$ | H | (401) |
| 143 | B1 | —N[CH$_2$—CH(CH$_3$)$_2$]$_2$ | H | mp. 238° C. |
| 144 | B13 | —CH$_2$—CH(CN)$_2$ | H | mp. 160° C. |
| 106 | B6f | —CH=C(CN)—C(=O)—C(CH$_3$)$_3$ | H | (E), mp. 193° C. |
| 145 | B9F | [(E)-2-(pyridin-3-yl)vinyl] | H | (E), mp. 229° C. |
| 146 | B9F | [(Z)-2-(pyridin-3-yl)vinyl] | H | (Z), mp. 258° C. |
| 147 | B9Ea | —CH=C(CN)—CH$_2$—CN | H | (Z/E=88/12) (406) |
| 148 | B6c | —C(CH$_2$—CH$_3$)=CH—CN | H | (E), mp. 173° C. |
| 149 | B6c | —C(CH(CH$_3$)$_2$)=CH—CN | H | (E), mp. 132° C. |
| 150 | B6c | —(CH(CH$_3$)$_2$)=CH—CN | H | (Z), mp. 132° C. |
| 151 | B6b | —CH=C(CH$_3$)—CN | H | (Z), mp. 246° C. |
| 152 | B6b | —CH=C(CH$_3$)—CN | H | (E), mp. 201° C. |
| 153 | B13 | —CH$_2$—CH(CH$_3$)—CN | H | mp. 187° C. |
| 124 | B15b | —C(Cl)=CH—CN | H | |
| 154 | B9Ba | —CH=CH—C(=O)—N(CH$_3$)—CH$_2$—CN | H | (E) |
| 112 | B9Ba | —CH=CH—C(=O)—N(CH$_3$)$_2$ | H | (E), mp. > 264° C. |

TABLE 3-continued

| Comp No. | Ex. No. | R³ | R⁴ | Physical data m.p. ° C. (MH+)* |
|---|---|---|---|---|
| 155 | B9Bc | (E)-CH=CH-C(=O)-N(piperazine-N-CH₃) | H | (E), mp. 156° C. |
| 156 | B9Bc | (E)-CH=CH-C(=O)-N(morpholine) | H | (E), mp. 168° C. |
| 157 | B9Bc | (E)-CH=CH-C(=O)-N(piperidine) | H | (E), mp. > 265° C. |
| 158 | B9Bc | —CH=CH—C(=O)—N(CH₃)—CH₂—CH₃ | H | (E), mp. > 260° C. |
| 114 | B9Bc | —CH=CH—C(=O)—N(CH₃)—(CH₂)₂—CN | H | (E), mp. 168° C. |
| 159 | B9Bc | —CH=CH—C(=O)—N(CH₂—CH₃)₂ | H | (E), mp. 249° C. |
| 160 | B6b | —C(CH₃)=C(CH₃)—CN | H | (E) |
| 107 | B9Aa | —CH=CH—Cl | H | (Z), mp. 250° C. |
| 161 | B9Aa | —CH=CH—Br | H | (Z), mp. 248° C. |
| 111 | B9Ad | —CH=C(Br)₂ | H | mp. 223° C. |
| 122 | B9F | (E)-CH=CH-(2-pyridyl) | H | (E), mp. 120° C. |
| 162 | B9F | (E)-CH=CH-(4-pyridyl) | H | (E), mp. > 260° C. |
| 163 | B9F | -CH=CH-(4-pyridyl) | H | mp. 128° C. |
| 164 | B9FF | -CH=CH-(2-furyl) | H | mp. 104° C. |
| 125 | B16a | 5-(CH=N-OH)-2-furyl | H | |
| 104 | B2c | 5-(CHO)-2-furyl | H | |

TABLE 3-continued

Structure: R⁴ and R³ on dimethylphenyl-NH-pyrimidine-NH-phenyl-CN

| Comp No. | Ex. No. | R³ | R⁴ | Physical data m.p. °C. (MH+)* |
|---|---|---|---|---|
| 165 | B9F | -CH=CH-(2-thienyl) | H | mp. 112° C. |
| 166 | B9F | -CH=CH-(1-methyl-pyrrol-2-yl) | H | mp. 194° C. |
| 167 | B9F | -CH=CH-(4-cyanophenyl) | H | mp. 191° C. |
| 126 | B16b | -(5-cyano-furan-2-yl) | H | mp. > 260° C. |
| 168 | B4c | —CH₂—O—CH₂—CH₃ | H | mp. 201° C. |
| 117 | B9Da | H | —N(CH₃)₂ | mp. 132° C. |
| 120 | B9Eb | —CH=C(CN)₂ | H | |
| 253 | B17a/b | —CH=CH—C(=O)NH₂ | H | (E) |
| 254 | B17b | —CH=CH—C(=O)NH₂ | H | (E) HCl |

*(MH⁺) defines the mass of the protonated compound; it was determined with a MicroMass spectrometer equipped with an electrospray probe with a quadripolar analyser.

TABLE 4

Structure: dimethylphenyl-O-pyrimidine-NR¹-phenyl-CN with R³ on phenyl

| Comp No. | Ex. No. | R³ | R¹ | Physical data mp.° C./(MH+)* |
|---|---|---|---|---|
| 25 | B6c | —CH=CH—CN | H | mp. 256° C. |
| 99 | B3 | —CH₂—CN | H | mp. 184° .C |
| 100 | B4b | —CH₂—N(CH₂—CH₃)₂ | H | mp. 172° C. |
| 102 | B13 | —CH₂—CH₂—CN | H | mp. 224° C. |
| 101 | B4b | —CH₂—N(CH₃)—CH₂—CH₂ | H | mp. 196° C. |
| 26 | B14 | —CH=CH—CN | CH₃ | mp. 195° C. |
| 169 | B9Bd | —C('O)—N(CH₂—CH₃)₂ | H | mp. 172° C. |
| 170 | B4b | —CH₂—(CH₃)—CH₂—CN | H | |
| 171 | B4b | -CH₂-(2,5-dihydropyrrol-1-yl) | H | (398) |
| 172 | B2a | -(3-thienyl) | H | mp. 158° C. |

TABLE 4-continued

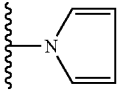

| Comp No. | Ex. No. | R³ | R¹ | Physical data mp.° C./(MH+)* |
|---|---|---|---|---|
| 173 | B4b | —CH₂—N(CH₃)—CH₂—CH₂—N(CH₃)₂ | H | mp.196° C. |
| 174 | B4b | —CH₂—N(CH₃)—CH=N—CN | H | mp. 254° C. |
| 175 | B14 | 2-furanyl | CH₃ | mp. 178° C. |
| 118 | B9Db | 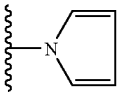 | H | 164° C. |
| 176 | B14 | 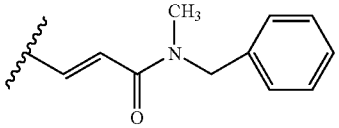 [SMILES: */C=C/C(=O)N(C)Cc1ccccc1] | CH₃ | mp. 188° C. |
| 177 | B9Aa | —CH=CH—Br | H | (Z), mp. 169° C. |
| 110 | B9Ac | —CH=C(F)—CN | H | (E), mp. 254° C. |
| 178 | B6b | —CH=C(CH₃)—CN | H | (Z) |
| 179 | B6b | —CH=C(CH₃)—CN | H | (E) |
| 180 | B9Bb | 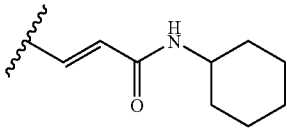 [SMILES: */C=C/C(=O)NC1CCCCC1] | H | (E) |
| 181 | B9Bc | —CH=CH—C(=O)—NH-cyclopropyl | H | (E) (426) |
| 182 | B9Bc | —CH=CH—C(=O)—NH—CH₂—CH₂—N(CH₃)₂ | H | (E) (427) |
| 183 | B9Bc | —CH=CH—C(=O)—NH—CH₂—CH₂—CH₂—O—CH₃ | H | (E) (458) |
| 184 | B9Bc | —CH=CH—C(=O)—NH—CH₂—CH(CH₃)₂ | H | (E) (442) |
| 185 | B9Bc | —CH=CH—C(=O)—NH—CH₂—CH₂—CN | H | (E) 439) |
| 186 | B9Bc | 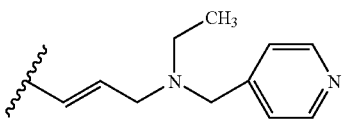 [SMILES: */C=C/CN(CC)Cc1ccncc1] | H | (E) (468) |
| 187 | B9Bc | —CH=CH—C(=O)—NH—CH₂—CH₂—CH₂—N(CH₃)₂ | H | (E) (471) |
| 188 | B9Bc | —CH=CH—C(=O)—NH—(CH₂)₃—O—CH₂—CH₃ | H | (E) (472) |
| 189 | B9Bc | —CH=CH—C(=O)—NH—CH₂—CH₃ | H | (E) (414) |
| 190 | B9Bc | —CH=CH—C(=O)—NH—CH₂—CH₂—O—CH₃ | H | (E) (444) |
| 191 | B9Bc | —CH=CH—C(=O)—NH—CH(CH₃)₂ | H | (E) (428) |
| 192 | B4b | 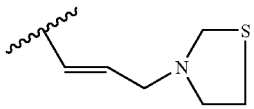 [SMILES: */C=C/CN1CCSC1] | H | (E) (491) |
| 193 | B4b |  | H | (E) (444) |
| 194 | B4b | —CH=CH—CH₂—N(CH₃)—CH₂—CH₂—CN | H | (E) (439) |

TABLE 4-continued

[Structure: 2,6-dimethylphenyl with R³ substituent, O-linked to pyrimidine-NR¹-phenyl-CN]

| Comp No. | Ex. No. | R³ | R¹ | Physical data mp.° C./(MH+)* |
|---|---|---|---|---|
| 195 | | [piperidine-4-carboxamide with CH=CH-CH₂- linker] | H | (E) (483) |
| 196 | B4b | —CH=CH—CH₂—N(CH₂—CH₂—O—CH₃)₂ | H | (E) (488) |
| 197 | B4b | [N-methyl-N-benzyl with CH=CH-CH₂- linker] | H | (E) (476) |
| 198 | B4b | —CH=CH—CH₂—N(CH₃)—CH₂—CH₂—CH₃ | H | (E) (428) |
| 199 | B4b | —CH=CH—CH₂—N(CH₃)—CH₂—CH₂—N(CH₂—CH₃)₂ | H | (E) (485) |
| 200 | B4b | —CH=CH—CH₂—N(CH₂—CH₃)—CH₃ | H | (E) (414) |
| 201 | B4b | —CH=CH—CH₂—N(CH₂—CH₂—CH₃)₂ | H | (E) (456) |
| 202 | B4b | —CH=CH—CH₂—N(CH₃)—CH₂—CH₂—CH₂—CH₃ | H | (E) (442) |
| 203 | B4b | [tetrahydropyridinyl with CH=CH-CH₂- linker] | H | (E) (438) |
| 204 | B4b | [morpholinyl with CH=CH-CH₂- linker] | H | (E) (442) |
| 205 | B4b | [4-methylpiperazinyl with CH=CH-CH₂- linker] | H | (E) (455) |
| 206 | B4b | —CH=CH—CH₂—N(benzyl)—CH₂—CH₂—N(CH₃)₂ | H | (E) (533) |
| 207 | B4b | —CH=CH—CH₂—N(CH₃)₂ | H | (E) (457) |
| 208 | B4b | —CH=CH—CH₂—N(isopropyl)₂ | H | (E) (456) |
| 121 | B9Bb | —CH=CH—C(=O)—NH₂ | H | (E) |
| 209 | B9Bb | [2,5-dihydropyrrol-1-yl carbonyl with CH=CH- linker] | H | (E), mp. 116° C. |
| 210 | B9Bb | [N-methyl-N-(1-methylpiperidin-4-yl)amide with CH=CH- linker] | H | (E), mp. 254° C. |
| 211 | B9Bb | —CH=CH—C(=O)—N(CH₃)—CH₂—CH₂—OH | H | (E), mp. 222° C. |
| 212 | B9Ba | —CH=CH—C(=O)—N(CH₃)—CH₂—CN | H | (E), mp. 198° C. |
| 213 | B6c | —C(CH₃)=CH—CN | H | (E) |
| 214 | B9Bc | —CH=CH—C(=O)—N(CH₃)—CH₂CH₂—CN | H | (E), mp. 204° C. |
| 215 | B9Bc | —CH=CH—C(=O)—N(CH₃)—CH₂—CH₃ | H | (E), mp. 211° C. |

TABLE 4-continued

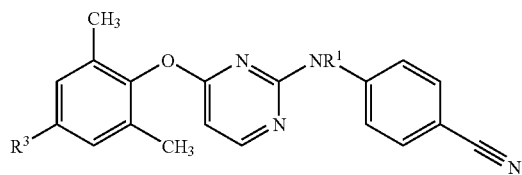

| Comp No. | Ex. No. | R³ | R¹ | Physical data mp.° C./(MH+)* |
|---|---|---|---|---|
| 216 | B9Bc | (morpholinyl acrylamide) | H | (E), mp. 246° C. |
| 217 | B9Bc | —CH=CH—C(=O)—N(CH₂—CH₃)₂ | H | (E) mp. 226° C. |
| 218 | B9Bc | (piperidinyl acrylamide) | H | (E), mp. 196° C. |
| 219 | B9Ba | —CH=CH—C(=O)—N(CH₃)₂ | H | (E), mp. 225° C. |
| 220 | B9E | —CH=C(CN)—CH₂—CN | H | (Z), mp. 195° C. |
| 109 | B9Ab | —CH=CH—Cl | H | (E), mp. 200° C. |
| 108 | B9Ab | —CH=CH—Cl | H | (Z), mp. 165° C. |
| 221 | B9Ba | —CH=CH—C(=O)—NH—CH₃ | H | (E), mp. 260° C. |
| 222 | B9Bb | —CH=CH—C(=O)—N(CH₂—CH₂—O—CH₃)₂ | H | (E), mp. 158° C. |
| 223 | B9Bb | (thiomorpholinyl acrylamide) | H | (E), mp. 208° C. |
| 224 | B9Bb | (N-methyl-N-phenethyl acrylamide) | H | (E), mp. 208° C. |
| 113 | B9Bb | —CH=CH—C(=O)—N(CH₃)—CH₂—CH₂—CH₂—CH₃ | H | (E), mp. 212° C. |
| 225 | B4b | —CH₂—N(CH₂—CH₂—CN)₂ | H | mp. 154° C. |
| 226 | B2a | 2-furanyl | H | mp. 162° C. |

*(MH⁺) defines the mass of the protonated compound; it was determined with a MicroMass spectrometer equipped with an electrospray probe with a quadripolar analyser.

TABLE 5

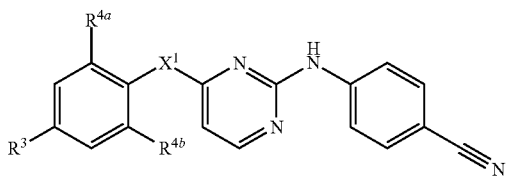

| Comp No. | Ex. No. | R³ | R⁴ᵃ | R⁴ᵇ | X¹ | Physical data mp. ° C. |
|---|---|---|---|---|---|---|
| 227 | B13 | —CH₂—CH₂CN | CH₃ | H | —NH | mp. 186° C. |
| 228 | B4b | —CH₂—N(CH₃)—CH₂—CN | CH₃ | H | —NH | mp. 138° C. |
| 229 | B6b | —CH=C(CH₃)—CN | CH₃ | H | —NH | mp. 190° C. |
| 230 | B6c | —CH=CH—CN | CH₃ | H | —O— | (E), mp. 254° C. |
| 231 | B6b | —CH=C(CH₃)=CN | CH₃ | H | —O— | mp. 150° C. |
| 232 | B6c | —C(CH₃)=CH—CN | CH₃ | H | —O— | (E), mp. 234° C. |
| 105 | B4d | —CH₂—O—CH₂—CH₃ | CH₃ | H | —O— | mp. 140° C. |

TABLE 5-continued

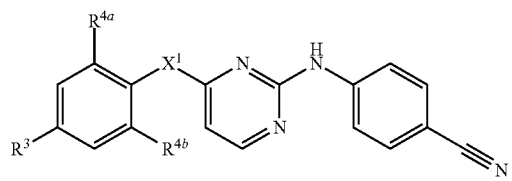

| Comp No. | Ex. No. | R³ | R⁴ᵃ | R⁴ᵇ | X¹ | Physical data mp. ° C. |
|---|---|---|---|---|---|---|
| 233 | B6b | —CH=C(CH₃)—CN | CH₃ | Cl | —NH | mp. 140° C. |
| 234 | B13 | —CH₂—CH₂—CN | CH₃ | H | —O— | mp. 199° C. |
| 235 | B13 | —CH(CH₃)—CH₂—CN | CH₃ | H | —O— | mp. 195° C. |
| 236 | B13 | —CH₂—CH(CH₃)—CN | CH₃ | H | —O— | mp. 161° C. |
| 237 | B6c | —CH=CH—CN | CH₃ | H | —NH | (E), mp. > 264° C. |
| 238 | B3 | —CH₂—CN | CH₃ | Cl | —NH | mp. 184° C. |
| 239 | B6c | —CH=CH—CN | CH₃ | 2-furanyl | —NH | (E) mp. 175° C. |
| 119 | B9E | —CH=C(CN)—CH₂—CN | CH₃ | 2-furanyl | —NH | |
| 240 | B9F | (pyridyl-vinyl group) | CH₃ | Cl | —NH | mp. 248° C. Z/E = 50/50 |
| 241 | B4b | —CH₂—N(CH₃)—CH₂—CH₂—CN | CH₃ | Br | —NH | mp. 148° C. |
| 242 | B1 | —CH=CH—CN | H | isopropyl | —NH | (E) 30%-(Z) 70% |
| 243 | B4b | —CH₂—N(CH₃)—CH₂—CH₂—CN | CH₃ | Cl | —NH | mp. 85° C. |
| 244 | B6c | —CH=CH—CN | H | Br | —NH | (E), mp. 270° C. |
| 245 | B6c | —CH=CH—CN | H | —OCH₃ | —NH | (E), mp. 258° C. |
| 246 | B6b | —C(CH₃)=C(CH₃)—CN | CH₃ | H | —O— | (E), mp. 214° C. |
| 247 | B6b | —CH=C(CH₃)—CN | CH₃ | Br | —NH | mp. 212° C. |
| 248 | B6c | —CH=CH—CN | CH₃ | Br | —NH | (E), mp. 250° C. |
| 249 | B6b | —CH=C(CH₃)—CN | H | —OCH₃ | —NH | mp. 166° C. |
| 250 | B6b | —CH=C(CH₃)—CN | H | Br | —NH | mp. 186° C. |
| 251 | B13 | —CH₂—CH₂—CN | H | —OCH₃ | —NH | mp. 228° C. |
| 252 | B4c | —CH₂—O—CH₂—CH₂—CN | H | Cl | —NH | mp. 168° C. |
| 133 | B6c | —CH=CH—CN | CH₃ | Cl | —NH | (E), mp, 258° C. |

C. Pharmacological Example

The pharmacological activity of the present compounds was examined using the following test.

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in M) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in M). The ratio of $CC_{50}$ to $IC_{50}$ was defined as the selectivity index (SI).

Table 6 lists the $pIC_{50}$ ($-\log IC_{50}$), $pCC_{50}$ ($-\log CC_{50}$) and $pSI$ ($pCC_{50}-pIC_{50}$) values for the compounds of formula (I). For example, a compound with a $IC_{50}$ value of $10^{-9}$M, i.e. $pIC_{50}$=9, and a $CC_{50}$ value of $10^{-5}$ M, i.e. $pCC_{50}$=5 has a SI of $10^{-5}$ M/$10^{-9}$M=10.000, i.e. a pSI of 5-9=-4.

TABLE 6

| Co. No. | $pIC_{50}$ (M) | $pCC_{50}$ (M) | pSI |
|---|---|---|---|
| 21 | 8.4 | 4.9 | -3.5 |
| 3 | 8.4 | 5.5 | -2.9 |
| 1 | 9.4 | 5.0 | -4.4 |
| 34 | 8.0 | 4.8 | -3.2 |
| 19 | 8.4 | 4.8 | -3.6 |
| 45 | 8.7 | 5.0 | -3.8 |
| 49 | 8.0 | 4.8 | -3.2 |
| 70 | 8.1 | 4.8 | -3.3 |
| 75 | 9.0 | 5.0 | -4.0 |
| 78 | 8.4 | 4.9 | -3.5 |
| 79 | 8.0 | 5.3 | -2.7 |
| 84 | 9.0 | 4.5 | -4.5 |
| 18 | 8.8 | 4.9 | -4.0 |
| 25 | 9 | 4 | -5 |
| 24 | 9.1 | 5.7 | -3.4 |
| 81 | 9.1 | 5.6 | -3.5 |
| 11 | 9.2 | 5.7 | -3.5 |
| 10 | 9.2 | 6.3 | -2.9 |
| 174 | 8.8 | 5.3 | -3.5 |

TABLE 6-continued

| Co. No. | pIC$_{50}$(M) | pCC$_{50}$(M) | pSI |
|---|---|---|---|
| 227 | 9.5 | <4.0 | <-5.5 |
| 144 | 8.6 | 6.4 | -2.2 |
| 229 | 8.8 | <4.0 | <-4.8 |
| 118 | 8.4 | 4.1 | <-4.1 |
| 177 | 8.3 | <4.0 | <-4.3 |
| 106 | 7.7 | 5.2 | -2.5 |
| 145 | 8.7 | 5.3 | -3.4 |
| 147 | 9.4 | 5.7 | -3.7 |
| 148 | 8.8 | 4.9 | -3.9 |
| 230 | 9.2 | <4.0 | <-5.2 |
| 231 | 9.2 | <4.0 | <-5.2 |
| 232 | 8.4 | <4.0 | <-4.4 |
| 105 | 7.2 | <4.0 | <-3.2 |
| 110 | 8.6 | 4.3 | -4.3 |
| 233 | 9.3 | 5.7 | -3.6 |
| 234 | 8.7 | <4.0 | <-4.7 |
| 235 | 9.3 | <4.0 | <-5.3 |
| 236 | 8.8 | <4.0 | <-4.8 |
| 149 | 9.1 | 5.3 | -3.8 |
| 150 | 8.8 | 4.8 | -4.0 |
| 237 | 8.9 | <4.0 | <-4.9 |
| 151 | 9.1 | 5.5 | -3.6 |
| 152 | 9.1 | 4.8 | -4.3 |
| 178 | 8.8 | 5.7 | -3.1 |
| 179 | 8.9 | <4.0 | <-4.9 |
| 153 | 9.2 | 6.3 | -2.9 |
| 124 | 8.5 | 4.7 | -3.8 |
| 238 | 9.5 | 5.6 | -3.9 |
| 112 | 9.1 | 4.9 | -4.2 |
| 244 | 9.2 | 4 | -5.2 |
| 209 | 8.6 | 4.9 | -3.7 |
| 210 | 8.3 | 4.8 | -3.5 |
| 155 | 8.8 | 6.3 | -2.5 |
| 156 | 7.7 | 5.1 | -2.6 |
| 158 | 8 | 5.5 | -2.5 |
| 212 | 9.1 | 5 | -4.1 |
| 114 | 8.6 | 5.1 | -3.5 |
| 213 | 9 | 4.8 | -4.2 |
| 214 | 8.6 | 5.1 | -3.5 |
| 215 | 9.1 | 5.5 | -3.6 |
| 216 | 8.2 | 5 | -3.6 |
| 219 | 9.1 | 5 | -4.1 |
| 245 | 8.8 | 4 | -4.8 |
| 146 | 8.4 | 5.4 | -3 |
| 247 | 9.2 | 6.2 | -3 |
| 248 | 9.3 | 5.7 | -3.5 |
| 249 | 8.5 | 4 | -4.5 |
| 42 | 9 | 6.3 | -2.7 |
| 251 | 8.9 | 5 | -3.9 |
| 133 | 9.2 | 4 | -5.2 |
| 9 | 8.8 | 4.8 | -4 |
| 239 | 8.9 | 5 | -3.9 |
| 241 | 9.4 | 5.3 | -4.1 |
| 126 | 8.4 | 4.9 | -3.5 |

The compositions of the present invention may further comprise an organic polymer.

The supersaturated solution of the drug compound created by the components of the composition upon exposure to water as indicated above, may be stabilized by the viscosity enhancing effects of an organic polymer. The presence of the organic polymer will hinder precipitation of the drug compound as the microenvironment becomes more dilute as more water enters.

The organic polymer used in the compositions of the invention may be any of the physiologically tolerable water soluble synthetic, semi-synthetic or non-synthetic organic polymers.

Thus for example the polymer may be a natural polymer such as a polysaccharide or polypeptide or a derivative thereof, or a synthetic polymer such as a polyalkylene oxide (e.g. PEG), polyacrylate, polyvinylpyrrolidone, etc. Mixed polymers, e.g. block copolymers and glycopeptides may of course be used.

Since it is believed that the effect of the organic polymer arises from an enhancement in viscosity which serves to stabilize supersaturated solutions of the drug compound on dissolution of the composition of the invention, the polymer conveniently has a molecular weight in the range 500D to 2 MD, and conveniently has an apparent viscosity of 1 to 100 mPa·s when in a 2% aqueous solution at 20° C. For example, the water-soluble polymer can be selected from the group comprising alkylcelluloses such as methylcellulose,
hydroxyakylcelluloses such as hydroxymethylcellulose, hydroxyethylcellulose, hydroxypropylcellulose and hydroxybutylcellulose,
hydroxyalkyl alkylcelluloses such as hydroxyethyl methylcellulose and hydroxypropyl methylceilulose,
carboxyalkylcelluloses such as carboxymethylcellulose,
alkali metal salts of carboxyalkylcelluloses such as sodium carboxymethylcellulose,
carboxyalkylalkylcelluloses such as carboxymethylethylcellulose,
carboxyalkylcellulose esters,
starches,
pectins such as sodium carboxymethylamylopectin,
chitin derivates such as chitosan,
heparin and heparinoids,
polysaccharides such as alginic acid, alkali metal and ammonium salts thereof, carrageenans, galactomannans, tragacanth, agar-agar, gum arabic, guargum and xanthan gum,
polyacrylic acids and the salts thereof,
polymethacrylic acids and the salts thereof, methacrylate copolymers,
polyvinylalcohol,
polyvinylpyrrolidone, copolymers of polyvinylpyrrolidone with vinyl acetate,
polyalkylene oxides such as polyethylene oxide and polypropylene oxide and copolymers of ethylene oxide and propylene oxide, e.g. poloxamers and poloxamines.

Non-enumerated polymers which are pharmaceutically acceptable and have appropriate physico-chemical properties as defined hereinbefore are equally suited for preparing compositions according to the present invention.

Preferably the organic polymer is a cellulose ether, e.g. methyl cellulose, hydroxyethylmethylceliulose, or hydroxypropylmethylcellulose (HPMC), for example a Methocel™ (available from Colorcon, England) such as Methocel™ A, Methocel™ E, Methocel™ F, Methocel™ K, Methocel™ J or Methocel™ HB or a Metolose™ such as Metolose™ SM, Metolose™ SH or Metolose™ SE. Especially preferably the organic polymer is a hydroxypropylmethylcellulose, e.g. from 5 cps Methocel™ E to 15000 cps Methocel™ K15M.

Even very small quantities of the organic polymer serve to achieve a beneficial effect in the compositions of the invention. Thus in the compositions of the invention the organic polymer may conveniently be present at 0.05 to 35% by weight, preferably 0.1 to 20%, more preferably 0.5 to 15%, and most preferably 2 to 11% by weight (relative to the total weight of drug compound, acid or base, surfactant and organic polymer). The content and viscosity grade of the organic polymer both affect the dissolution profile for the drug compound in the compositions of the invention, with increased organic polymer content and/or increased viscosity grade (e.g. 15000 mPa·s in place of 5 mPa·s (mPa·s values being at 2% aqueous solution at 20°)) both tending to decelerate drug compound dissolution). Accordingly the selection of the identity and quantity of the organic polymer will generally depend upon the dissolution profile that is desired. For example, a composition that provides sustained release of the drug, will comprise a water soluble polymer having an apparent viscosity of more than 1,000 mPa·s when dissolved in a 2% aqueous solution at 20° C.

Thus, the compositions according to the invention can be designed in such a way as to provide a particular favourable drug dissolution profile. For instance, dissolution may be sufficiently rapid to ensure substantially complete availability of the drug compound for biological uptake (e.g. from the mouth, nose, stomach or vagina) yet sufficiently slow to provide a more prolonged plasma uptake profile e.g. by avoidance of drug reprecipitation before the composition reaches the stomach.

As a preferred embodiment, the invention provides a pharmaceutical composition comprising a basic drug compound, a surfactant, a physiologically tolerable acid and optionally an organic polymer, characterised in that at 5, 15 and 45 minutes after addition of a quantity of said composition containing 100 mg of said drug compound to 600 mL of 0.1N hydrochloric acid at 37° C., from 7 to 25 (preferably 10 to 20, especially 12 to 18) %, 45 to 70 (preferably 50 to 65, especially 54 to 63) % and at least 96 (preferably at least 97, especially at least 98) % respectively of said drug compound is in solution in said hydrochloric acid. These figures relate to in vitro dissolution studies conducted in accordance with the monograph USP 23, <711> Dissolution, pp. 1791-1793.

For example, in determining the dissolution profiles set out above, the composition is placed without a coating or with a rapidly soluble coating (e.g. a gelatin capsule shell) in 0.1 N HCl (or an other appropriate medium) and the mixture is stirred using the USP-method with a paddle, apparatus 2, at a speed of 50 or 100 rpm.

The compositions of the invention may if desired be aqueous, but in general will preferably be substantially water-free, e.g. containing up to 3% by weight, preferably less than 1% by weight water, and most preferably less than 0.5% water, but may be mixed with water immediately before administration or may be coated and dispersed in an aqueous medium whereby the coating is only broken down after administration. Such aqueous compositions are deemed to fall within the scope of the invention.

Depending on the selection of components, the compositions of the invention may be liquid, solid or semi-solid—e.g. gel-like. Preferably the compositions are non-freeflowing at ambient temperature (e.g. 21° C.), other than as free flowing particulates. Thus the compositions at ambient temperature are preferably solids or semi-solids or, less preferably, highly viscous fluids.

In the compositions of the invention the drug compound, surfactant, acid respectively base and optionally the organic polymer are intimately admixed.

Thus where the composition is particulate, the acid (base), drug compound, surfactant and optionally the organic polymer are mixed together within the particles (e.g. at the molecular level; this may be achieved by solvent removal from a solution of these components resulting in the formation of a solid or semi-solid dispersion). Granulate mixtures where individual particles do not contain all three or optionally four components, or have cores of one or more components coated with other components are not preferred. This intimate admixture is important since the effects of the components are complimentary at the microscopic level during dissolution of the compositions of the invention as explained hereinabove.

Preferably, all components are dispersed so as to form a system that is chemically and physically uniform or homogenous throughout, or consists of one phase as defined in thermodynamics; such a dispersion will be called a thermoplastic phase or system hereinafter. The components of the thermoplastic system are readily bioavailable to the organisms to which they are administered. This advantage can probably be explained by the ease with which said thermoplastic system can form liquid solutions when contacted with a body liquid such as gastric juice. The ease of dissolution may be attributed at least in part to the fact that the energy required for dissolution of the components from a thermoplastic system is less than that required for the dissolution of components from a crystalline or microcrystalline solid phase.

The term "a solid dispersion" used hereinbefore or hereinafter defines a system in a solid state (as opposed to a liquid or gaseous state) comprising the components of the present compositions, wherein one component is dispersed more or less evenly throughout the other components (the components may include additional pharmaceutically acceptable formulating agents, generally known in the art, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline drug compound, and/or amorphous, microcrystalline or crystalline surfactant, and/or amorphous, microcrystalline or crystalline acid or optionally amorphous, microcrystalline or crystalline polymer, are dispersed more or less evenly in another phase comprising a solid solution comprising a drug compound, a surfactant, an acid (base) and optionally a polymer. Said domains are regions within the solid dispersion distinctively marked by some physical feature, small in size, and evenly and randomly distributed throughout the solid dispersion.

The compositions of the invention may be prepared by making an intimate admixture of the drug compound, surfactant, acid (base) and optionally the organic polymer. This may be effected most straightforwardly by dissolving these components in a liquid solvent therefor and subsequently removing the solvent. Thus viewed from a further aspect the invention provides a process for the preparation of a pharmaceutical composition, said process comprising: dissolving a drug compound, a surfactant, a physiologically tolerable water-soluble acid (base) and optionally a physiologically tolerable water-soluble organic polymer in a solvent; removing solvent from the resultant solution; optionally forming the resultant product into desired shapes; and optionally coating the resulting product with a physiologically tolerable coating material.

Alternatively, when the components of the composition are thermostable, then the intimate admixture of said components can also be prepared by co-melting them. Therefore, the present invention also provides for a process for preparing the present pharmaceutical composition, said process comprising co-melting a drug compound, a surfactant, a physiologically tolerable water-soluble acid (base) and optionally a physiologically tolerable water-soluble organic polymer; and optionally forming the resultant product into desired shapes; and optionally coating the resulting product with a physiologically tolerable coating material.

In particular, the above described processes can be performed by using one of the following technologies:

a) spray-drying:
   The components of the present compositions can be dissolved in a suitable solvent and the thus obtained solution can be spray-dried to obtain a powder. The powder can further be processed in for instance tablets or filled into capsules.

b) Freeze-drying:
   The components of the present compositions can be dissolved in a suitable solvent and the thus obtained solution can then be freeze-dried in order to obtain a powder which can further be processed in for instance tablets or filled into capsules. Alternatively, the solution can also be freeze dried directly into a suitable mold, said suitable mold comprising the final blister pack.

c) Super critical fluid (SCF) technology:
   The components of the present compositions may be dissolved in a compressible fluid, in particular a supercritical fluid (i.e. any substance above its critical temperature and critical pressure, said supercritical fluid possessing both gas- and liquid-like properties) (in this case the SCF is considered as a solvent; reference therefore is made to RESS (Rapid Expansion of Supercritical Solutions) or PGSS (particles from Gas Saturated Solutions)) followed by removing the SCF (e.g. by decompression) and thus obtaining a powder which can further be processed in for instance tablets or filled into capsules. The super critical fluid technology can also be applied when the SCF is considered as an anti-solvent (reference therefore is made to GAS (Gas Anti Solvent), SEDS (Solution Enhanced Dispersion by Supercritical fluids), ASES (Aerosol Solvent Extraction System), SAS (Supercritical Anti Solvent) or PCA (Precipitation with Compressed Antisolvent). In this case, the components of the composition are dissolved in an appropriate solvent and the SCF is used to enhance solvent evaporation thus obtaining a powder, which can further be processed as described above.

d) Carrier coating:
   The components of the present compositions can be dissolved in a suitable solvent and the resulting solution can be coated, sprayed, granulated onto a suitable carrier followed by evaporating the solvent. Appropriate carriers that can be used depend on the technology used, for instance microcristalline cellulose can be used when pelletization is envisaged and then the appropriate equipment is for instance a fluid bed equipment, or fumed $SiO_2$ can be used for the formation of granulates and this can be achieved in for instance a high shear granulator or the carrier can be an inert core, e.g. a sugar bead, on which the solution of the components of the present composition can be sprayed. Evaporation of the solvent can be achieved by for instance drying at elevated temperatures and/or under vacuum or by applying microwaves.

e) Co-melting:
   When the components of the composition are thermostable, they can be physically mixed, melted and mixed again. The melted mix can then directly be shaped into desired shapes (calendaring; injection molding) e.g. the melt can be directly filled or injected in the final blister pack or can be filled or injected in desired molds or can be directly filled or injected into a capsule, followed by cooling. The melted mix can also first be allowed to cool and then further processed, e.g. by mining to powder and compressing into tablets or filling into capsules. The co-melting of the components of the present composition may be performed by simply heating the physical mixture or by meltextrusion. In the latter case, the components are physically mixed and fed into a hot stage extruder in which the mix is heated, melted and compounded followed by shaping the resulting meltextrudate as described above, e.g. by injection molding or the meltextrudate can cooled followed by milling into a powder which can further be processed into a tablet or which can be filled into a capsule.
   Alternatively, the melt can also be granulated (melt granulation; high shear granulator), sprayed or coated onto a suitable carrier (reference therefore is made to item d)). In the case of melt granulation, the melting can be performed in a melt-extruder where the carrier is added during the extrusion process and the resulting extrudate can be shaped as described above. In case the carrier is a suitable excipiens which allows spheronization, the obtained extrudate can be spheronized, for instance by using a marumarizer.

f) Extrusion
   The components of the composition can be mixed and fed into an extruder, for instance via the dry powder feeder, and the solvent optionally containing the surfactant can be added to the extruder, for instance via an inlet port. The solvent is evaporated while the mixture is still in the extruder. After extrusion, the extrudate is shaped (calendaring).
   Alternatively, a solution containing the components of the invention can be fed into the extruder, the solvent is evaporated while the product is still in the extruder and finally the extrudate is shaped.
   Alternatively, a solution of the components of the composition can be granulated onto a suitable carrier, e.g. microcrystalline cellulose, and the wetted powder is extruded. The resulting extrudate is then spheronized for instance by using a marumarizer after which the resulting pellets are dried to remove the solvent. The pellets can be filled directly into capsules or they can further be processed into tablets.

Preferably, the present compositions are prepared by extrusion as described under point f) above. A skilled man is able to recognize the appropriate steps and process parameters to perform extrusion of a composition comprising a solvent, wherein the solvent is evaporated in the extruder. Reference therefore is made to e.g. WO98/10752.

The solvent used in the processes described above is preferably a physiologically tolerable material, suitably an organic solvent such as a $C_{1-6}$ alkanol (e.g. ethanol), acetone, N,N-dimethylformamide, a linear or cyclic ether (e.g. diethyl ether, dimethyl ether, or tetrahydrofuran), cyclohexane, dimethylsulfoxide, etc. or a solvent mixture that also may comprise water. For an acid with a high melting point, solvents or solvent mixtures which have high boiling points may conveniently be used; generally however the boiling point of the solvent or solvent system will be no more than about 100° C. Such solvents may be used efficiently in the production of the compositions of the invention and the level of residual solvent will be minimal. The solvent may conveniently be removed by evaporation, e.g. under reduced pressure, and as this may leave some solvent residue (e.g. up to 3% by weight) it is particularly desirable to use a solvent such as ethanol (or an ethanol-water mixture) which is a permitted pharmaceutical excipient.

As described above, super critical fluids can also be used. Suitable SCF are for instance $CO_2$, $N_2O$, $N_2$, short chain alkanes, such as for instance methane, ethane and the like.

If the drug compound is insoluble or poorly soluble in the solvent of choice, the process of the invention may involve dispersion of microparticles (e.g. nanoparticles having a particle size of 1 to 100 nm) of the drug compound in the solvent rather than full dissolution of the drug compound. If this is done, it is desirable that the drug compound particles be as small as possible. Nanoparticles of insoluble compounds may be prepared for example by various precipitation techniques or by milling with physiologically tolerable inorganic beads, e.g. of zirconia (EP-0.499.299).

The solvent removal may be essentially complete or it may be incomplete, in the former case to produce a solid or a gel-like solid or semi-solid, and in the latter case to produce a viscous fluid which can for example be filled into capsules.

In general, essentially complete solvent removal will be preferred as the resultant product can then readily be shaped. As already indicated above, shaping may be effected by spray-drying the solution (to provide the product in particulate form), by evaporation of solvent from solution disposed in molds, by molding (e.g. injection molding), by extrusion and the like. As already indicated, the product can be formed when hot and allowed to solidify on cooling. The shaped product may likewise be produced in film or sheet form by evaporation or by pouring a heated mass onto a plate and evaporating off the solvent.

In one preferred embodiment the product is shaped by filling into (e.g. by pouring or by extrusion or by injecting) capsule shells, e.g. of gelatin.

An alternative process to prepare the compositions of the invention is to prepare the dispersion of the drug compound, surfactant and acid (base) as described above and to mix the thus obtained product physically with the organic polymer.

Yet a further alternative process to prepare the present compositions is to prepare a dispersion of the drug compound, the acid (base) and optionally the organic polymer by dissolving them in a solvent followed by removing the solvent, and subsequently mixing the thus obtained product with the surfactant optionally at elevated temperature.

It will be recognized that for the above described processes a skilled person is able to recognize the most favourable parameters and the most appropriate equipment. It is also well-known to the skilled person that particle size, particle size distribution, crystallinity and morphology of the obtained powders according to the processes described above can be adapted to specific requirements by appropriately adjusting process parameters, such as for instance the temperature, nozzle size and shape, gas addition in case of spray processes.

The compositions of the present invention may be formulated into a suitable dosage form.

Thus the present invention also provides pharmaceutical dosage forms comprising a therapeutically effective amount of a composition as described hereinbefore.

For example if the drug is to be delivered in a standard capsule (e.g. with a 900 mg capacity for a glass thermoplastic system as described in the present invention, and the desired drug dose is 100 mg/capsule) then the quantities and natures of the other composition components may be selected to give the desired drug dissolution profile—in general only a small quantity of organic polymer, e.g. 20 to 50 mg, may be necessary, and the balance may be made up from acid (base) and surfactant with the ratio of acid to surfactant being set according to the required dissolution profile, e.g. with 200 to 400 mg surfactant and 450 to 650 mg acid (base).

Besides the drug compound, the organic polymer, the acid (base) and the surfactant, the compositions of the invention may contain other conventional pharmaceutical excipients, e.g. flavours, colouring agents, antioxidants, bulking agents, glidants, lubricants, fats, waxes, coating agents, dispersants, suspension fluids (e.g. where the composition coated with a gastric juice resistant coating and dispersed as particles in a suspension fluid such as water or a syrup), etc. Preferably such components when in intimate admixture with the drug compound will make up only a minor proportion of the composition, e.g. 0.01 to 10% by weight (relative to the total weight of acid (base), surfactant, drug compound and optionally the organic polymer). However where the composition of the invention is encapsulated or disposed in a carrier (e.g. a fluid or a solid or semi-solid matrix), the further components not in intimate admixture with the drug compound (e.g. coating or encapsulating materials, dispersion media, etc.) may of course make up a minor or major proportion, e.g. 5 to 95% by weight, of the overall composition.

The product may be hygroscopic, and thus may be "tacky" if touched by hand due to its absorption of moisture from the skin. Accordingly it is particularly preferred for the product to be provided with a protective coating to prevent moisture uptake during handling. Such coatings may for example take the form of capsule casings (as described above), tablet coatings, protective film or web coatings, and moisture-proof removable wrappings. Tablet coatings may be applied in conventional manner and may be such as to dissolve in the mouth or stomach (e.g. sugar or sugar/beeswax coatings), or alternatively may be gastric juice resistant polymers (such as the gastric juice resistant Eudragit™ coatings produced by Röhm GmbH) where it is desired that drug uptake should occur in the intestines. Protective films or webs may for example be used where the product is to be applied topically, e.g. for uptake across the skin or a toe or finger nail. In this event a pad of the composition will generally be disposed between an adhesive upper protective layer and a lower removable layer. An example of a topical application form for application on nails and adjoining tissue, e.g. for the treatment of fungal infection, is shown in U.S. Pat. No. 5,181,914.

The present compositions may also comprise suitable lubricants such as for example sodium stearyl fumarate, to avoid sticking.

Where the product is produced in particulate form, e.g. by spray-drying, the particles can be loaded into water-tight administration devices (e.g. spray devices or powder dosing devices such as inhalers) for oral, nasal or topical administration of the particulate. Alternatively particulates may be loaded into capsules or mixed with bulking agents such as lactose, starch, microcrystalline cellulose and mixtures thereof, and compressed to form tablets. In any event, the particles may additionally be provided with one or more coatings, e.g. to provide a delayed or prolonged release administration forms.

Generally however it will be preferred to shape the product into individual doses and to provide these with a protective coat, e.g. to produce a capsule, coated tablet or film covered pad single dosage unit.

The compositions according to the invention may be in any form convenient for topical administration or administration into an externally voiding body cavity (e.g. nose, lungs, mouth, ear, stomach, rectum or vagina). Typical administration forms include patches, tablets, buccal tablets, lozenges, ear-plugs, nose plugs, coated tablets, capsules, suppositories, chewing gum, gels, powders, granules, syrups and dispersions, although patches and powders and more especially capsules and coated tablets are preferred. The drug dosage will depend upon the drug compound as well as on the condition being treated and on the species and size of the subject being treated.

Further, this invention comprises a pharmaceutical composition or a pharmaceutical dosage form as described hereinbefore for use in a method of prophylaxis, therapy or diagnosis of the human or non-human animal body.

This invention also relates to a pharmaceutical composition for use in the manufacture of a pharmaceutical dosage form for oral administration to a mammal in need of treatment, characterized in that said dosage form can be administered at any time of the day independently of the food taken in by said mammal.

Or, in other words, the present invention also concerns the use of a pharmaceutical composition as described hereinbefore for the manufacture of a pharmaceutical dosage form for oral administration to a mammal in need of treatment, characterized in that said dosage form can be administered at any time of the day independently of the food taken in by said mammal.

This invention also relates to a method of prophylaxis, therapy or diagnosis of the human or non-human animal body which comprises administering to said body a therapeutically or diagnostically effective dose of a pharmaceutical composition according to the present invention.

This invention also relates to a pharmaceutical package suitable for commercial sale comprising a container, an oral dosage form as claimed in any one of claims 16 to 18, and associated with said package written matter non-limited as to whether the dosage form can be administered with or without food.

The invention will now be described further with reference to the following non-limiting Examples.

Example 1

The following compositions according to the present invention were prepared:

| Composition 1 | |
|---|---|
| Cisapride | 114 mg |
| Tartaric acid | 35.6 mg |
| Lutrol ™ F68 | 457 mg |
| Composition 2 | |
| Cisapride | 114 mg |
| Tartaric acid | 10 g |
| Lutrol ™ F68 | 457 mg |

Preparation of Composition 1

114 mg of cisapride and 457 Lutrol™ F68 were dissolved in 1.14 g of aceton. Tartaric acid 35.6 mg was dissolved in 1.90 ml of EtOH and this solution was added to the aceton solution. The resulting mixture was evaporated under vacuum (rotavapor) at a temperature of 85° C. The residue was grounded and further dried under vacuum at 80° C., followed by grounding.

Preparation of Composition 2

Composition 2 was prepared analogously to composition 1 except that the 10 g of tartaric acid were dissolved in 53.3 ml of EtOH.

The in vitro dissolution profiles of compositions 1 and 2 were determined by placing that amount of composition 1 or 2 containing 5.7 mg of cisapride in 10 ml of USP buffer pH 6.8 (USP buffer pH 6.8 was prepared by bringing 6.805 g of $KH_2PO_4$, 109.5 ml of a 0.2 N NaOH solution and 700 ml of distilled water in a 1 liter beaker. After complete dissolution while stirring, the resulting mixture was brought to a volume of 1 liter with distilled water in an appropriate recipient) at 37° C. and by measuring the percentage of dissolved cisapride as a function of time (stirring was effected by a magnetic stirrer and the concentration of dissolved cisapride was measured by UV absorption).

The results are set out in Table 7.

TABLE 7

| Percentage of cisapride in solution | | |
|---|---|---|
| Time | Composition 1 | Composition 2 |
| 0 | 0 | 0 |
| 5 | 1.68 | 98.15 |
| 30 | 1.51 | 98.33 |
| 60 | 1.47 | 98.15 |
| 120 | 1.45 | 98.24 |

Composition 2 clearly shows a much faster in vitro dissolution compared to composition 1. Thus, incorporating a significant amount of acid in the composition results in an enhanced solubility and hence the drug compound is made much more readily bioavailable.

Example 2

Gelatine capsules were prepared containing the following composition:

| Composition 3 | |
|---|---|
| R103757* | 100 mg |
| Citric acid monohydrate | 500 mg |
| Cremophor RH 40 | 250 mg |
| Methocel ™ E 5 | 50 mg |

*R103757 corresponds to (−)-[2S-[2α,4α(S*)]]-4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one The above composition was prepared by dissolving 500 mg of R103757, 2.5 g of citric acid monohydrate, 250 mg of Methocel™ E5 and 1,250 mg of Cremophor RH 40 in 2.5 ml of EtOH. After complete dissolution, the solution was poured onto a teflon plate which was then placed in a drying oven for 2 hours at 80° C. under vacuum. The resulting residue was scrapped off and the amount corresponding to 100 mg of R103757 was filled into gelatin capsules (size No 0).

The in vitro dissolution profile of composition 3 was determined by placing one capsule containing composition 3 in 600 mL of stirred 0.1 N HCl at 37° C. and observing (UV absorption) the percentage of dissolved drug compound at times 0, 5, 15, 30, 45 and 60 minutes (stirring was effected using the USP-method with paddle, apparatus 2, 100 rpm).

The results are set out in Table 8.

TABLE 8

Composition 3
Percentage of R103757 in solution

| Time | Sample 1 | Sample 2 |
|---|---|---|
| 0 | 0 | 0 |
| 5 | 14.94 | 14.34 |
| 15 | 62.70 | 59.10 |
| 30 | 94.32 | 93.12 |
| 45 | 101.64 | 102.06 |
| 60 | 102.84 | 103.14 |

Example 3

Gelatine capsules were prepared containing the following composition:

| Composition 4 | |
|---|---|
| R112625* | 100 mg |
| Citric acid monohydrate | 325 mg |
| Laureth 23 | 325 mg |
| Methocel ™ E 5 | 25 mg |

*R112625 corresponds to (+)-(trans)-4-[1-[3,5-bis(trifluoromethyl)benzoyl]-2-(phenylmethyl)-4-piperidinyl]-N-(2,6-dimethylphenyl)-1-piperazine acetamide The above composition was prepared by dissolving 1 g of R112625, 3.25 g of citric acid monohydrate and 250 mg of Methocel™ E5 in 6 ml of EtOH at 70° C. Adding 3.25 g of Laureth 23 to said solution while further stirring. After complete dissolution, the solution was poured onto a teflon plate which was then placed in a drying oven for 2 hours at 80° C. under vacuum. The resulting residue was scrapped off and the amount corresponding to 100 mg of R112625 was filled into gelatin capsules (size No 0).

The in vitro dissolution profile of composition 4 was determined according to the procedure described for composition 3.

The results are set out in Table 9.

TABLE 9

Composition 4
Percentage of R112625 in solution

| Time | Sample 1 |
|---|---|
| 0 | 0 |
| 5 | 10.98 |
| 15 | 51.87 |
| 30 | 80.82 |
| 45 | 97.08 |
| 60 | 101.91 |

Example 4

Stability Testing

Gelatine capsules were prepared containing the following composition:

| Composition 5 | |
|---|---|
| R112625 | 100 mg |
| Citric acid monohydrate | 325 mg |
| Cremophor RH40 | 325 mg |
| Methocel ™ E 5 | 25 mg |

The composition was prepared analogously according to the procedure described in Example 3.

Capsules containing composition 5 were stored for 1 month at room temperature. Dissolution measurements were made according to the method described above for composition 3.

The results are set out in Table 10.

TABLE 10

Composition 5
Percentage of R112625 in solution

| Time | Testing at time 0 | Testing after 1 month at room temperature |
|---|---|---|
| 0 | 0 | 0 |
| 5 | 9.26 | 9.75 |
| 15 | 43.74 | 44.16 |
| 30 | 78.13 | 80.22 |
| 45 | 92.64 | 99.09 |
| 60 | 101.64 | 102.39 |

The above results support the stability of the compositions of the invention.

Example 5

Immediate Release-Extended Release Formulations

The following compositions according to the present invention were prepared:

Composition 6

| Composition 6 | |
|---|---|
| R165335* | 50 mg |
| Citric acid monohydrate | 500 mg |
| Cremophor RH 40 | 250 mg |

Composition 7

| Composition 7 | |
|---|---|
| R165335* | 50 mg |
| Citric acid monohydrate | 500 mg |
| Cremophor RH 40 | 250 mg |
| Polyox ™ WSR 303 | 30 mg |

Composition 8

| Composition 8 | |
|---|---|
| R165335* | 50 mg |
| Citric acid monohydrate | 500 mg |
| Cremophor RH 40 | 250 mg |
| Polyox ™ WSR 303 | 50 mg |

*R165335 corresponds to 4-[[6-amino-5-bromo-2-[(4-cyanophenyl)amino]-4-pyrimidinyl] oxy]-3,5-dimethylbenzonitrile.

Composition 6 was prepared by dissolving 5000 mg of R165335 in 150 ml of aceton at 60° C. followed by adding 50 g of citric acid monohydrate while stirring until complete dissolution. Consequently 25 g of Cremophor RH 40 was added to the solution. After complete dissolution, the solution was poured onto teflon plates which were then placed in a drying oven for 2 hours at 80° C. under vacuum. The resulting residue was scrapped off. Compositions 7 and 8 were prepared starting from composition 6 by mixing the appropriate amount of Polyox™ WSR 303 with the corresponding amount of composition 6.

The in vitro dissolution profile of compositions 6, 7 and 8 were determined by placing that amount of compositions 6, 7 or 8 that contains 50 mg of R165335 in a basket in 900 mL of stirred 0.01 N HCl containing 2.5% of sodium lauryl sulfate at 37° C. and observing (UV absorption) the percentage of dissolved drug compound at times 0, 5, 15, 30, 45, 60 up to 360 minutes (stirring was effected using the USP-method with basket, apparatus 1,100 rpm).

The results are set out in Table 11.

TABLE 11

Composition 5
Percentage of R165335 in solution

| Time | Composition 6 | Composition 7 | Composition 8 |
|---|---|---|---|
| 0 | 0 | 0 | 0 |
| 5 | 22.86 | 8.42 | 4.12 |
| 15 | 65.88 | 20.03 | 7.45 |
| 30 | 95.82 | 35.96 | 12.17 |
| 45 | 100.18 | 47.89 | 16.67 |
| 60 | 100.70 | 58.24 | 24.07 |
| 75 | | 69.65 | 29.52 |
| 90 | | 78.24 | 35.25 |
| 105 | | 84.73 | 40.61 |
| 120 | | 90.35 | 47.00 |
| 150 | | 101.01 | 56.28 |
| 180 | | 101.90 | 65.30 |
| 240 | | | 79.29 |
| 300 | | | 93.45 |
| 360 | | | 100.70 |

From the results gathered in Table 11 it can be concluded that the dissolution rate of the compositions of the invention can be extended by adding an organic polymer to the compositions.

Composition 6 was also subjected to a stability test. The composition was stored for 8 months at room temperature and then the percentage of R165335 in the composition was determined by High Performance Liquid Chromatography. After the 8 months storage period, the composition still contained 98.5% of R165335, supporting the stability of the drug compound in the composition.

Example 6

In vivo Study

The following compositions were prepared
Composition 9

| Composition 9 | |
|---|---|
| R165335 | 125 mg |
| Citric acid monohydrate | 492 mg |
| Cremophor RH 40 | 242 mg |
| Methocel ™ E5 | 42 mg |

Composition 10

| Composition 10 | |
|---|---|
| R278474* | 50 mg |
| Citric acid monohydrate | 500 mg |
| VitE TPGS | 250 mg |
| Methocel ™ E5 | 25 mg |

R278474* corresponds to 4-[[4-[[4-(2-cyanoethenyl)-2,6-dimethylphenyl]amino]-2-pyrimidinyl]amino]benzonitrile.

Composition 9 was prepared by dissolving 500 mg of R165335 in 5 ml of tetrahydrofuran at boiling temperature (solution A). 1966.6 mg of citric acid monohydrate, 966 mg of Cremophor RH 40 and 166.66 mg of Methocel™ E5 were dissolved in 4 ml of EtOH at 80° C. (solution B). Solution A was added to solution B while stirring. The thus obtained solution was poured onto a teflon plate which was then placed in a drying oven for 2 hours at 80° C. under vacuum. The resulting residue was scrapped off and filled into gelatine capsules (size Nr 0) for use in the in vivo study.

Composition 10 was prepared by dissolving 300 mg of R278474, 3 g of citric acid monohydrate and 150 mg of Methocel™ E5 in 5 ml of EtOH at 70° C. The solution was evaporated at 85° C. under vacuum for 1 hour. 3 g of the thus obtained residue was mixed with 1.304 g of VitE TPGS at 80° C.

R165335 was orally administered to male beagle dogs as a capsule containing composition 9 and as a PEG400 solution (10 mg of R165335/ml PEG 400) at a dose of 10 mg/kg. Each formulation was tested in 2 dogs. Plasma levels of R165335 were measured (HPLC) for 32 hours after oral administration. The results are set out in Table 12.

R278474 was orally administered to male beagle dogs as a capsule containing composition 10 and as a PEG400 solution (40 mg of R278474/ml PEG 400) at a dose of 5 mg/kg. Each formulation was tested in 2 dogs. Plasma levels of R278474 were measured (LC-MS) for 72 hours after oral administration. The results are set out in Table 13. Table 14 reports the mean values for $C_{max}$, $T_{max}$ and $AUC_{0-72h}$ for the PEG-400 solution study and the composition 10 study.

TABLE 12

| Formulation | Day | Time | Plasma levels (ng/ml) of R165335 | |
|---|---|---|---|---|
| | | | Dog 1 | Dog 2 |
| PEG-400 solution | 0 | 0 h | NQ | NQ |
| | | 0.5 h | 160 | 93.9 |
| | | 1 h | 251 | 183 |
| | | 2 h | 420 | 301 |

TABLE 12-continued

| Formulation | Day | Time | Plasma levels (ng/ml) of R165335 | |
|---|---|---|---|---|
| | | | Dog 1 | Dog 2 |
| | | 4 h | 498 | 351 |
| | | 8 h | 283 | 384 |
| | 1 | 24 h | 105 | 167 |
| | | 32 h | 92.2 | 120 |
| Capsule with composition 9 | 0 | 0 h | NQ | NQ |
| | | 0.5 h | 53.3 | NQ |
| | | 1 h | 898 | 97.2 |
| | | 2 h | 2930 | 1011 |
| | | 4 h | 1868 | 548 |
| | | 8 h | 873 | 243 |
| | 1 | 24 h | 301 | 113 |
| | | 32 h | 227 | 82.5 |

NQ = Not quantifiable

TABLE 13

| Formulation | Day | Time | Plasma levels (ng/ml) of R278474 | |
|---|---|---|---|---|
| | | | Dog 1 | Dog 2 |
| PEG-400 solution | 0 | 0 h | 0 | 0 |
| | | 0.5 h | 1.8 | 203 |
| | | 1 h | 8.4 | 404 |
| | | 2 h | 35.8 | 520 |
| | | 4 h | 115 | 460 |
| | | 6 h | 162 | 367 |
| | | 8 h | 148 | 365 |
| | 1 | 24 h | 74.0 | 187 |
| | | 32 h | 38.4 | 147 |
| | 2 | 48 h | 31.9 | 94.6 |
| | 3 | 72 h | 19.3 | 70.1 |
| Capsule with composition 10 | 0 | 0 h | 0 | 0 |
| | | 0.5 h | NQ | 80.2 |
| | | 1 h | 13 | 694 |
| | | 2 h | 260 | 1178 |
| | | 4 h | 899 | 1040 |
| | | 6 h | 1056 | 1052 |
| | | 8 h | 1111 | 850 |
| | 1 | 24 h | 427 | 497 |
| | | 32 h | 316 | 490 |
| | 2 | 48 h | 236 | 232 |
| | 3 | 72 h | 181 | 226 |

NQ = Not quantifiable

TABLE 14

| Mean values | PEG-400 solution | Composition 10 |
|---|---|---|
| $C_{max}$ (ng/ml) | 341 | 1144.50 |
| $T_{max}$ (h) | 4 | 5 |
| $AUC_{0-72 h}$ (ng·h/ml) | 8359 | 31008 |

The above results clearly demonstrate the outstanding performance of composition 10 compared to PEG 400 solution. Composition 10 clearly has an improved pharmacokinetic profile compared to the PEG 400 solution.

Example 7

Effect of surfactant on solubility and on stability of the supersaturated condition.

Aqueous solutions of 2.5% (w/v) of hydroxypropyl-β-cyclodextrin (HPβCD) [1], 2.5% (w/v) of Vit E TPGS [2], 2.5% (w/v) Cremophor RH 40 [3], 2.5% (w/v) of sodium lauryl sulfate [4] or 2.5% (w/v) of PEG 4000 [5] in 0.01 N HCl at 37° C. were prepared.

To 10 ml of these solutions, with stirring, a concentrated solution of R278474 or R165335 in N,N-dimethylformamide (100 mg/ml) was added dropwise until precipitation of the drug compound was observed. After 5, 30, 60 and 120 minutes, the concentration of dissolved R278474 or R165335 expressed in mg % (i.e. the number of mg dissolved in 100 ml) was determined. The results are set out in Table 15.

TABLE 15

| | Time (minutes) | concentration | | | | | |
|---|---|---|---|---|---|---|---|
| | | 0.01N HCl mg % | [1] mg % | [2] mg % | [3] mg % | [4] mg % | [5] mg % |
| R278474 | 5 | 18.02 | 27.68 | 91.75 | | | 23.60 |
| | 30 | 16.30 | 24.80 | 83.50 | | | 21.60 |
| | 60 | 15.90 | 24.40 | 76.25 | | | 20.60 |
| | 120 | 15.95 | 24.10 | 75.25 | | | 20.10 |
| R165335 | 5 | NM* | 0.04 | | 54.20 | 35.09 | 0.02 |
| | 30 | NM | 0.12 | | 24.88 | 37.85 | 0.04 |
| | 60 | NM | 0.17 | | 20.06 | 38.80 | 0.07 |
| | 120 | NM | 0.07 | | 18.44 | 38.35 | 0.04 |

*NM stands for not measurable

The results set out in Table 15 clearly demonstrate the higher solubilizing effect (creating a supersaturation condition) of the surfactant compared to that of a cyclodextrin, such as HPβCD, or a cosolvent, such as PEG 4000. The results also indicate that the surfactants are able to maintain the supersaturated condition for some time.

We claim:

1. A semi-solid or solid pharmaceutical solid dispersion composition comprising a basic drug compound selected from 4-[[4-[[4-(2-cyanoethenyl)-2,6-dimethylphenyl]amino]-2-pyrimidinyl]amino]-benzonitrile; 4-[[24(cyanophenyl)amino]-4-pyrimidinyl]amino]-3,5-dimethylbenzonitrile; 4-[[4-[(2,4,6-trimethylphenyl)amino]-2-pyrimidinyl]amino]benzonitrile; 4-[[4-amino-5-bromo-6-(4-cyano-2,6-dimethylphenyloxy)-2-pyrimidinyl]amino-]-benzonitrile; or a pharmaceutical acceptable salt or stereochemically isomeric form thereof, Vitamin E TPGS, a physiologically tolerable water-soluble acid selected from citric or tartaric acid, wherein the acid:drug compound ratio ranges from 1:1 to 100:1 by weight, and wherein the basic drug compound is present in 10% by weight relative to the total weight of acid, Vitamin E TPGS and drug compound, and an organic polymer, wherein said polymer is not polyalkylene oxide.

2. The composition according to claim 1 wherein the basic drug compound, Vitamin E TPGS and the acid are intimately admixed.

3. The composition according to claim 1 wherein the acid is citric acid.

4. The composition according to claim 1 wherein the polymer is selected from alkylcelluloses, hydroxyakylcelluloses, hydroxyalkyl alkylcelluloses, carboxyalkylcelluloses, alkali metal salts of carboxyalkylcelluloses, carboxyalkylcellulose esters, starches, pectins, chitosan, heparin, heparinoids, polysaccharides, polyacrylic acids and salts thereof, polymethacrylic acids and salts thereof, methacrylate copolymers, polyvinylalcohol, polyvinylpyrrolidone, and copolymers of polyvinylpyrrolidone with vinyl acetate.

5. The composition according to claim 4 wherein the polymer is selected from methylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, sodium carboxymethylcellulose, carboxymethylethylcellulose, sodium carboxymethylamylopectin, chitosan, alginic acid, alkali metal and ammonium salts thereof, carrageenans, galactomannans, tragacanth, agar-agar, gum arabic, guar-gum, xanthan gum, poloxamers, and poloxamines.

6. The composition according to claim 1 wherein the polymer has an apparent viscosity of 1-100 mPa·s when dissolved in a 2% aqueous solution at 20° C.

7. The composition according to claim 1 wherein the polymer is hydroxypropylmethylcellulose.

8. The composition according to claim 1 wherein the polymer is a water soluble polymer having an apparent viscosity of more than 1,000 mPa·s when dissolved in a 2% aqueous solution at 20° C. and wherein the composition provides sustained release of the drug.

9. The composition according to claim 1 wherein the basic drug compound is no more than sparingly soluble in water.

10. The composition according to claim 1 wherein Vitamin E TPGS is present in a concentration of 1 to 70% by weight relative to the total weight of Vitamin E TPGS, acid, and basic drug compound.

11. The composition according to claim 1 wherein Vitamin E TPGS is present in a concentration of 5 to 55% by weight relative to the total weight of Vitamin E TPGS, acid, and basic drug compound.

12. The composition according to claim 1 wherein Vitamin E TPGS is present in a concentration of 10 to 50% by weight relative to the total weight of Vitamin E TPGS, acid, and basic drug compound.

13. The composition according to claim 1 wherein the weight by weight ratio of Vitamin E TPGS to basic drug compound is in the range of from 100:1 to 1:5.

14. The composition according to claim 1 wherein the weight by weight ratio of Vitamin E TPGS to basic drug compound is in the range of from 50:1 to 1:2.

15. The composition according to claim 1 wherein the weight by weight ratio of Vitamin E TPGS to basic drug compound is in the range of from 10:1 to 1:1.

16. A pharmaceutical dosage form comprising a therapeutically effective amount of a pharmaceutical composition as defined in claim 1.

17. The dosage form of claim 16 wherein the dosage form is adapted for topical administration or administration into the nose, lungs, mouth, ear, stomach, rectum, or vagina.

18. The dosage form of claim 16 wherein said composition is filled into a standard capsule, or is mixed with at least one bulking agent and compressed into a tablet.

19. A method of treating a mammal with an oral pharmaceutical composition, comprising administering the pharmaceutical composition as a pharmaceutical composition according to claim 1 at any time of the day independent of any food taken in by said mammal.

20. A pharmaceutical package suitable for commercial sale comprising a container, an oral dosage form as claimed in claim 1, and associated with said package, written matter non-limited as to whether the dosage form can be administered with or without food.

21. A process for preparing a composition according to claim 1 comprising: dissolving a basic drug compound, Vitamin E TPGS, a physiologically tolerable water-soluble acid, and a physiologically tolerable water-soluble organic polymer, in a solvent; removing the solvent from the resultant solution to form the resultant product; optionally forming the resultant product into desired shapes; and optionally coating the resulting product with a physiologically tolerable coating material.

22. The process according to claim 21 wherein the solvent is removed by spray-drying.

23. The process according to claim 21 wherein the solvent is removed by freeze-drying.

24. The process according to claim 21 wherein the solvent is a supercritical fluid.

25. A process according to claim 24 wherein the supercritical fluid is removed by decompression.

26. The process according to claim 24 wherein the supercritical fluid technology is Rapid Expansion of Supercritical Solutions or particles from Gas Saturated Solutions.

27. The process according to claim 21 further comprising adding a supercritical fluid, in addition to the solvent.

28. The process according to claim 27 wherein the supercritical fluid technology is Gas Anti Solvent, Solution Enhanced Dispersion by Supercritical fluids, Aerosol Solvent Extraction System, Supercritical Anti Solvent, or Precipitation with Compressed Antisolvent.

29. The process according to claim 21 wherein the solution is coated, sprayed or granulated onto a suitable carrier followed by evaporating the solvent.

30. The process according to claim 29 wherein the solution is granulated onto a suitable carrier followed by evaporating the solvent.

31. The process according to claim 29 wherein the solvent is evaporated by drying at elevated temperatures and/or under vacuum or by applying microwaves.

32. The process according to claim 29 wherein the carrier is microcrystalline cellulose, fumed $SiO_2$, or an inert core.

33. The process according to claim 32 wherein the carrier is fumed $SiO_2$.

34. The process according to claim 29 wherein the process is carried out in a high shear granulator.

35. The process according to claim 21 wherein the process is performed in an extruder.

36. The process according to claim 35 wherein the solution of the components of the composition is granulated onto a suitable carrier and the resultant wetted powder is extruded.

37. A process of preparing a composition according to claim 1 comprising: co-melting a basic drug compound, Vitamin E TPGS, a physiologically tolerable water-soluble acid and a physiologically tolerable water-soluble organic polymer; and optionally forming the resultant product into desired shapes; and optionally coating the resulting product with a physiologically tolerable coating material.

38. The process according to claim 37 wherein the co-melting is performed by meltextrusion.

39. The process according to claim 37 wherein the resultant product is granulated, sprayed or coated onto a suitable carrier.

40. The process according to claim 37 wherein the resultant product is granulated onto a suitable carrier.

41. The process according to claim 40 wherein the carrier is microcrystalline cellulose, fumed $SiO_2$, or an inert core.

42. The process according to claim 40 wherein the carrier is fumed $SiO_2$.

43. The process according claim 37 wherein the process is carried out in a high shear granulator.

* * * * *